(12) United States Patent
Parham et al.

(10) Patent No.: US 8,785,636 B2
(45) Date of Patent: Jul. 22, 2014

(54) SUBSTITUTED INDOLOACRIDINES FOR ORGANIC ELECTROLUMINESCENT DEVICES

(75) Inventors: Amir Hossain Parham, Frankfurt am Main (DE); Christof Pflumm, Frankfurt am Main (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 13/500,377

(22) PCT Filed: Sep. 9, 2010

(86) PCT No.: PCT/EP2010/005555
§ 371 (c)(1),
(2), (4) Date: Apr. 5, 2012

(87) PCT Pub. No.: WO2011/042107
PCT Pub. Date: Apr. 14, 2011

(65) Prior Publication Data
US 2012/0202997 A1    Aug. 9, 2012

(30) Foreign Application Priority Data
Oct. 8, 2009   (DE) .................. 10 2009 048 791

(51) Int. Cl.
*C07D 471/00*    (2006.01)
(52) U.S. Cl.
USPC .......................................................... 546/43
(58) Field of Classification Search
CPC ..................................................... C07D 471/00
USPC .......................................................... 546/43
See application file for complete search history.

(56) References Cited

U.S. PATENT DOCUMENTS

2009/0136779 A1   5/2009  Cheng et al.
2009/0295275 A1   12/2009  Parham et al.

FOREIGN PATENT DOCUMENTS

| EP | 2182040 A2 | 5/2010 |
| JP | H11339868 A | 12/1999 |
| JP | 2003022893 A | 1/2003 |
| WO | WO-2006033563 A1 | 3/2006 |
| WO | WO-2006080640 A1 | 8/2006 |
| WO | WO-2007031165 A2 | 3/2007 |
| WO | WO 2010/050778 | * 3/2010 |

OTHER PUBLICATIONS

Wharton, et al., "The Production and Characterisation of Novel Conducting Redox-Active Oligomeric Thin Films from Electrooxidised Indolo[3,2,1-*jk*]Carbazole", Chem. Eur. J., vol. 15, (2009), pp. 5482-5490.
International Search Report for PCT/EP2010/ mailed Apr. 21, 2011.

\* cited by examiner

*Primary Examiner* — Douglas M Willis
(74) *Attorney, Agent, or Firm* — Drinker Biddle & Reath LLP

(57) ABSTRACT

The present invention relates to compounds of the formula (1) and formula (2) which are suitable for use in electronic devices, in particular organic electroluminescent devices.

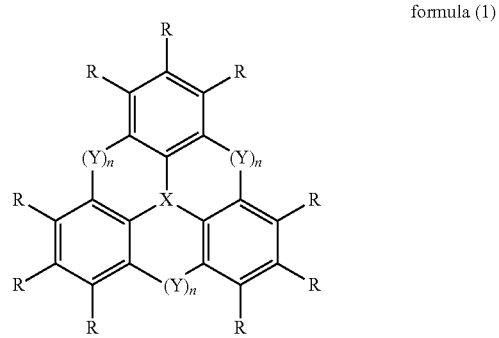

formula (1)

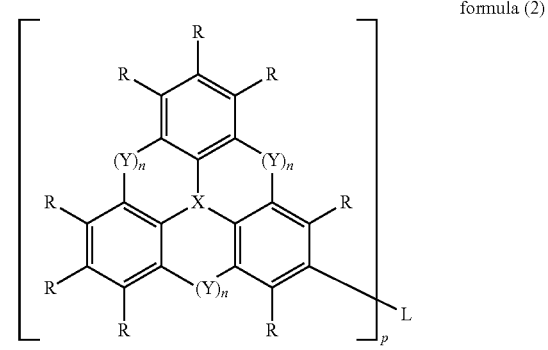

formula (2)

12 Claims, No Drawings

SUBSTITUTED INDOLOACRIDINES FOR ORGANIC ELECTROLUMINESCENT DEVICES

CROSS-REFERENCE TO RELATED APPLICATIONS

This application is a national stage application (under 35 U.S.C. §371) of PCT/EP2010/005555, filed Sep. 9, 2010, which claims benefit of German application 10 2009 048 791.3, filed Oct. 8, 2009.

BACKGROUND OF THE INVENTION (1) Field of the Invention

The present invention relates to materials for use in electronic devices, in particular in organic electroluminescent devices.

(2) Description of Related Art

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence (M. A. Baldo et al., *Appl. Phys. Lett.* 1999, 75, 4-6). For quantum-mechanical reasons, an up to four-fold increase in energy and power efficiency is possible using organometallic compounds as phosphorescence emitters. In general, however, there is still a need for improvement, for example with respect to efficiency, operating voltage and in particular lifetime, in OLEDs, in particular also in OLEDs which exhibit triplet emission (phosphorescence). This applies, in particular, to OLEDs which emit in the relatively short-wavelength range, for example green.

The properties of phosphorescent OLEDs are determined not only by the triplet emitters employed. In particular, the other materials used, such as matrix materials, hole-blocking materials, electron-transport materials, hole-transport materials and electron- or exciton-blocking materials, are also of particular importance here. Improvements in these materials can thus also result in significant improvements in the OLED properties. There is also still a need for improvement in these materials for fluorescent OLEDs.

In accordance with the prior art, ketones (for example in accordance with WO 04/093207 or WO 10/006680) or phosphine oxides (for example in accordance with WO 05/003253), inter alia, are used as matrix materials for phosphorescent emitters. However, there is still a need for improvement, in particular with respect to the efficiency and lifetime of the device, on use of these matrix materials as in the case of other matrix materials. The object of the present invention is the provision of compounds which are suitable for use in a fluorescent or phosphorescent OLED, in particular a phosphorescent OLED, for example as matrix material or as hole-transport/electron-blocking material or exciton-blocking material or as electron-transport or hole-blocking material. In particular, the object of the present invention is to provide matrix materials which are suitable for green- and red-phosphorescent OLEDs.

Surprisingly, it has been found that certain compounds described in greater detail below achieve this object and result in significant improvements in the organic electroluminescent device, in particular with respect to the lifetime, efficiency and operating voltage. This applies, in particular, to red- and green-phosphorescent electroluminescent devices, especially on use of the compounds according to the invention as matrix material. The present invention therefore relates to these materials and to organic electroluminescent devices which comprise compounds of this type.

WO 07/031165 discloses bridged triarylamine structures having a similar basic structure to the compounds according to the invention. However, compounds which are substituted by the substituents according to the invention mentioned below are not disclosed therein. Furthermore, these compounds are only described as emitters or hole-transport materials, but not as matrix materials for phosphorescent emitters or as electron-transport materials.

US 2009/0136779 discloses compounds having a similar basic structure as matrix for phosphorescent emitters. However, compounds which are substituted by the substituents according to the invention mentioned below are not disclosed therein.

BRIEF SUMMARY OF THE INVENTION

The present invention relates to a compound of the following formula (1) or formula (2):

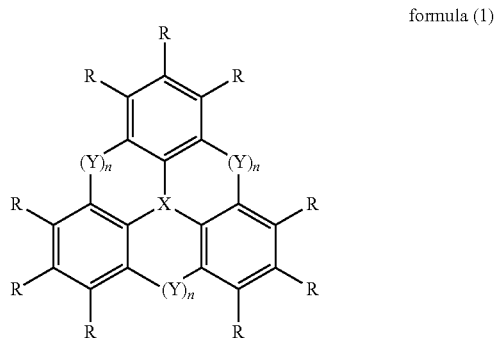

formula (1)

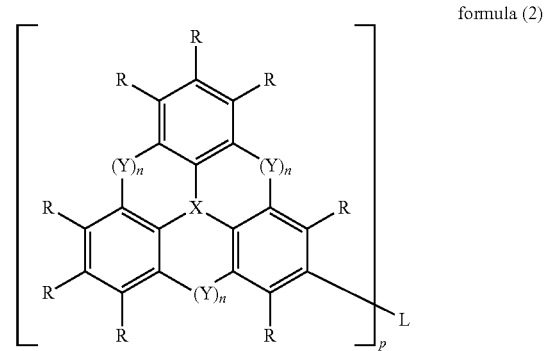

formula (2)

where the following applies to the symbols and indices used:

X is on each occurrence, identically or differently, N, P or P=O;

Y is, identically or differently on each occurrence, $C(R)_2$, NR, O, S, C=O, C=S, C=NR, $C=C(R)_2$, $Si(R)_2$, BR, PR, AsR, SbR, BiR, P(=O)R, As(=O)R, Bi(=O)R, SO, SeO, TeO, $SO_2$, $SeO_2$, $TeO_2$ or a chemical bond, with the proviso that all three groups Y in one unit do not simultaneously stand for a single bond;

R is selected on each occurrence, identically or differently, from the group consisting of H, D, F, Cl, Br, I, CN, $NO_2$, $N(Ar)_2$, $N(R^1)_2$, C(=O)Ar, $C(=O)R^1$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^1$, where one or more non-adjacent $CH_2$ groups may be replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms may be replaced by D, F, Cl, Br, I, CN or $NO_2$, an aromatic or heteroaromatic ring system having 5 to 80, preferably 5 to 60, aromatic ring atoms, which may in each case be substituted by one or more radicals $R^1$, an aryloxy or heteroaryloxy group having 5 to 60 aromatic ring atoms, which may be substituted by one or more radicals $R^1$, or a combination of these systems, where two or more adjacent substituents R may optionally form a monocyclic or polycyclic, aliphatic, aromatic or heteroaromatic ring system, which may be substituted by one or more radicals $R^1$;

$R^1$ is selected on each occurrence, identically or differently, from the group consisting of H, D, F, Cl, Br, I, CN, $NO_2$, $N(Ar)_2$, $N(R^2)_2$, $C(=O)Ar$, $C(=O)R^2$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^2$, where one or more non-adjacent $CH_2$ groups may be replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms may be replaced by D, F, Cl, Br, I, CN or $NO_2$, an aromatic or heteroaromatic ring system having 5 to 60 aromatic ring atoms, which may in each case be substituted by one or more radicals $R^2$, an aryloxy or heteroaryloxy group having 5 to 60 aromatic ring atoms, which may be substituted by one or more radicals $R^2$, or a combination of these systems, where two or more adjacent substituents R may optionally form a monocyclic or polycyclic, aliphatic, aromatic or heteroaromatic ring system, which may be substituted by one or more radicals $R^2$;

$R^2$ is selected from the group consisting of H, D, F, CN, an aliphatic hydrocarbon radical having 1 to 20 C atoms, an aromatic or heteroaromatic ring system having 5 to 30 aromatic ring atoms, in which one or more H atoms may be replaced by D, F, Cl, Br, I or CN, where two or more adjacent substituents $R^2$ may form a mono- or polycyclic, aliphatic, aromatic or heteroaromatic ring system with one another;

Ar is on each occurrence, identically or differently, an aromatic or heteroaromatic ring system having 5-30 aromatic ring atoms, which may be substituted by one or more non-aromatic radicals $R^2$; two radicals Ar which are bonded to the same N atom or P atom here may also be bridged to one another by a single bond or a bridge selected from $N(R^2)$, $C(R^2)_2$ or O;

L is a divalent or polyvalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, which may be substituted by in each case one or more radicals $R^1$, where one or more non-adjacent $CH_2$ groups may be replaced by $-R^1C=CR^1-$, $-C\equiv C-$, $Si(R^1)_2$, $Ge(R^1)_2$, $Sn(R^1)_2$, $C=O$, $C=S$, $C=Se$, $C=NR^1$, $P(=O)R^1$, $S=O$, $SO_2$, $-O-$, $-S-$ or $-CONR^1-$ and where one or more H atoms may be replaced by D, F, Cl, Br, I, CN or $NO_2$, or an at least divalent aromatic or heteroaromatic ring system having 5 to 80, preferably 5 to 40, aromatic ring atoms, which may be substituted by one or more radicals $R^1$, or $P(R^1)_{3-p}$, $P(=O)(R^1)_{3-p}$, $C(R^1)_{4-p}$, $Si(R^1)_{4-p}$, $N(Ar)_{3-p}$ or a combination of two, three, four or five of these systems; or L is a chemical bond;

n is on each occurrence, identically or differently, 0, 1 or 2, where, for n=0, a hydrogen or radical $R^1$ is present instead of Y, with the proviso that at least two indices n per unit are not equal to 0;

p is 2, 3, 4, 5 or 6, with the proviso that p is not greater than the maximum valence of L;

characterised in that at least one radical R stands for one of the groups of the following formulae (3) to (6):

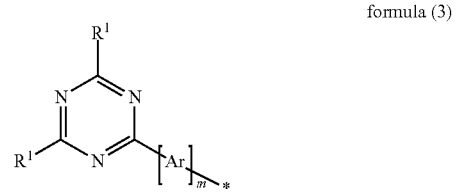

formula (3)

formula (4)

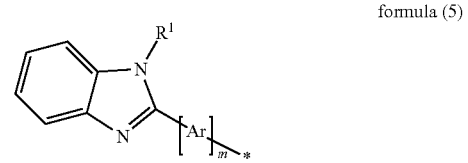

formula (5)

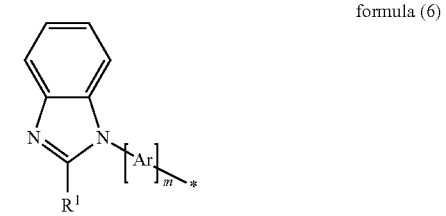

formula (6)

and/or in that at least one group Y stands for N—R and the R bonded to the nitrogen stands for a group of the following formulae (7) to (9):

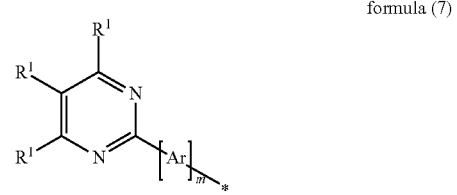

formula (7)

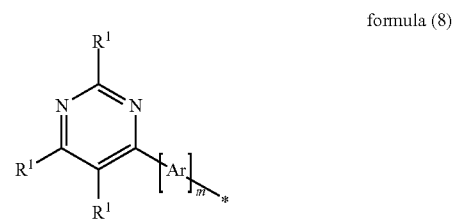

formula (8)

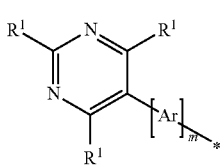
formula (9)

and/or in that at least one group L stands for a group of the following formulae (10) to (15):

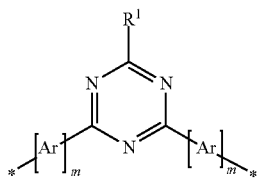
formula (10)

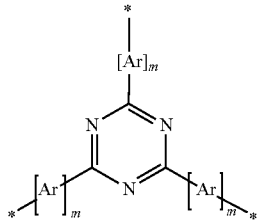
formula (11)

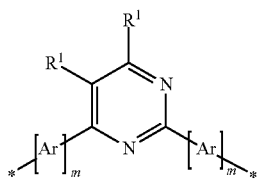
formula (12)

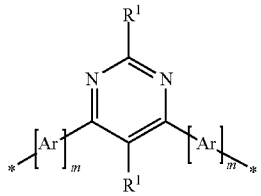
formula (13)

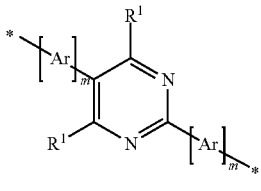
formula (14)

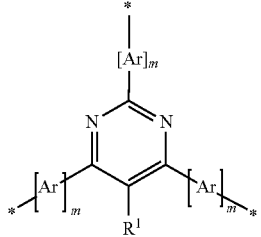
formula (15)

where the symbols used have the meanings given above, and the index m stands for 0 or 1; * here indicates the position of the bonding of the group of the formulae (3) to (15).

DETAILED DESCRIPTION OF THE INVENTION

The group of the formulae (3) to (6) here may either be bonded to one of the phenyl rings of the compound of the formula (1), (2) or to the group Y.

An aryl group in the sense of this invention contains 6 to 60 C atoms; a heteroaryl group in the sense of this invention contains 2 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, etc. Aromatic rings linked to one another by a single bond, such as, for example, biphenyl, are, by contrast, not referred to as an aryl or heteroaryl group, but instead as an aromatic ring system.

An aromatic ring system in the sense of this invention contains 6 to 80 C atoms in the ring system. A heteroaromatic ring system in the sense of this invention contains 2 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, a C, N or O atom. Thus, for example, systems such as fluorene, 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a short alkyl group.

For the purposes of the present invention, an aliphatic hydrocarbon radical or an alkyl group or an alkenyl or alkynyl group, which may typically contain 1 to 40 or also 1 to 20 C atoms and in which, in addition, individual H atoms or $CH_2$ groups may be substituted by the above-mentioned groups, is preferably taken to mean the radicals methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl and octynyl. An alkoxy group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 C atoms is taken to mean, in particular, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio. In general, alkyl, alkoxy or thioalkyl groups in accordance with the present invention may be straight-chain, branched or cyclic, where one or more non-adjacent $CH_2$ groups may be replaced by the above-mentioned groups; furthermore, one or more H atoms may also be replaced by D, F, Cl, Br, I, CN or $NO_2$, preferably F, Cl or CN, furthermore preferably F or CN, particularly preferably CN.

An aromatic or heteroaromatic ring system having 5-80 aromatic ring atoms, which may also in each case be substituted by the above-mentioned radicals $R^2$ or a hydrocarbon radical and which may be linked via any desired positions on the aromatic or heteroaromatic ring system, is taken to mean, in particular, groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole or groups derived from combinations of these systems.

In a preferred embodiment of the invention, a group Y stands for a single bond. Preferred compounds are thus the compounds of the formulae (16), (17) and (18):

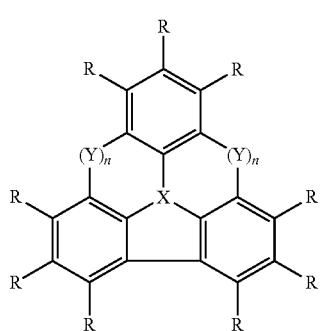

formula (16)

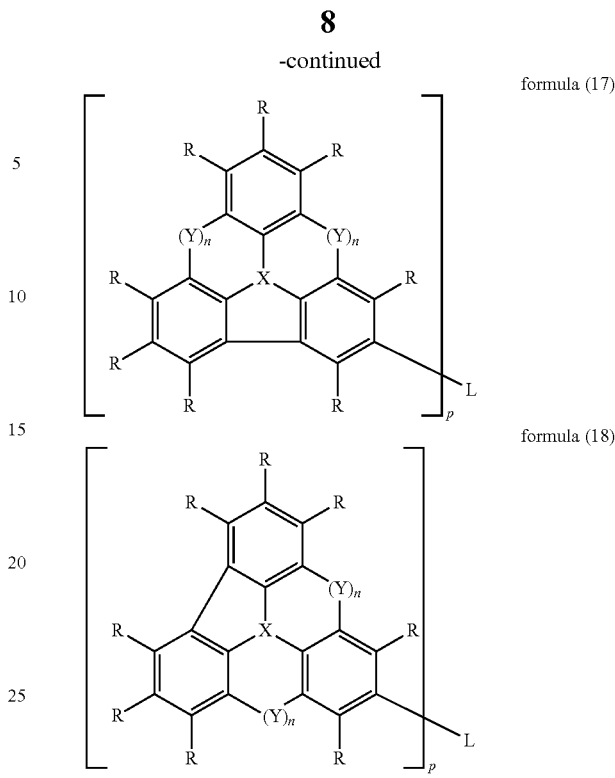

formula (17)

formula (18)

where the symbols and indices used have the meanings given above.

In a preferred embodiment of the compounds of the formulae (1), (2) and (16) to (18), X stands on each occurrence, identically or differently, for N or P. X particularly preferably stands for N.

In a further preferred embodiment of the compounds of the formulae (1), (2) and (16) to (18), Y stands on each occurrence, identically or differently, for $C(R)_2$, NR, O, S, C=O or a chemical bond. In compounds of the formulae (1) and (2), one group Y preferably stands for a chemical bond and the other groups Y preferably stand on each occurrence, identically or differently, for $C(R)_2$, NR, O, S, C=O or a chemical bond. In compounds of the formulae (16) to (18), the groups Y stand on each occurrence, identically or differently, for $C(R)_2$, NR, O, S, C=O or a chemical bond. In compounds of the formulae (1) and (2), all three groups Y do not simultaneously stand for a chemical bond, and in compounds of the formulae (16) to (18), both groups Y do not simultaneously stand for a chemical bond. The groups Y which are other than a chemical bond particularly preferably stand, identically or differently on each occurrence, for $C(R)_2$, NR, O or S, very particularly preferably for $C(R)_2$ or NR, in particular for $C(R)_2$.

Groups R which are bonded in Y are preferably selected, identically or differently on each occurrence, from the group consisting of alkyl groups having 1 to 10 C atoms or aromatic or heteroaromatic ring systems having 5 to 20 aromatic ring atoms, each of which may be substituted by one or more radicals $R^1$. In a particularly preferred embodiment of the invention, the groups R which are bonded in Y are selected, identically or differently on each occurrence, from aromatic or heteroaromatic ring systems having 5 to 20 aromatic ring atoms, which may in each case be substituted by one or more radicals $R^1$. In a further particularly preferred embodiment, one radical R, if Y stands for $C(R)_2$, is an alkyl group having 1 to 10 C atoms and the other radical R bonded to this carbon atom is an aromatic or heteroaromatic ring system having 5 to 20 aromatic ring atoms, which may be substituted by one or more radicals $R^1$.

Particular preference is given to the compounds of the following formulae (19) to (24):

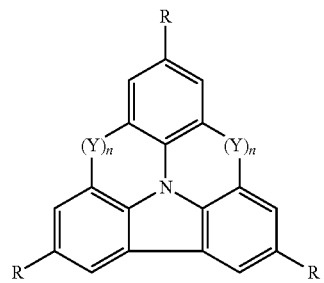

formula (19)

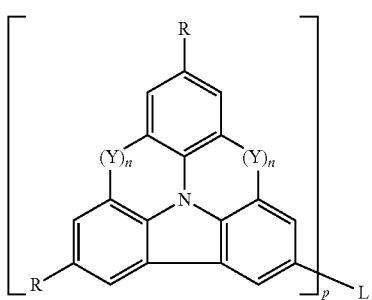

formula (20)

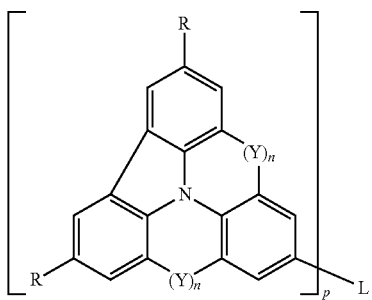

formula (21)

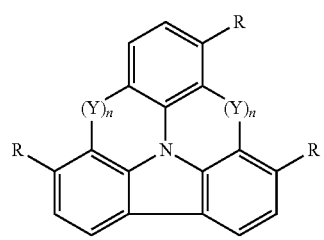

formula (22)

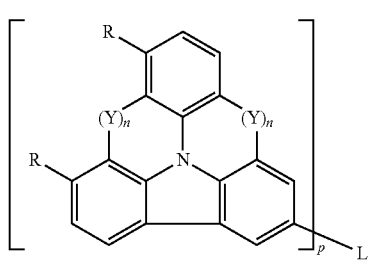

formula (23)

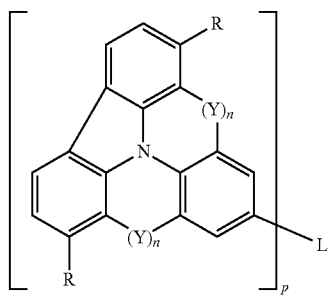

formula (24)

where Y stands, identically or differently on each occurrence, for O, S, $C(R)_2$ or NR, preferably $C(R)_2$ or NR, or where, in addition, one Y stands for a single bond, the C atoms drawn as unsubstituted may also be substituted by D instead of H, and the other symbols and indices have the meanings given above. The radicals R which are bonded to Y preferably have the preferred meanings given above.

In a further preferred embodiment of the invention, L is a divalent or polyvalent straight-chain alkylene group having 1 to 10 C atoms or a branched or cyclic alkylene group having 3 to 10 C atoms, which may be substituted by in each case one or more radicals $R^1$, where one or more H atoms may be replaced by D or F, or an at least divalent aromatic or heteroaromatic ring system having 5 to 24 aromatic ring atoms, which may be substituted by one or more radicals $R^1$; or L is a chemical bond; or L is a group of one of the formulae (10) to (15).

In a preferred embodiment of the invention, R is selected, identically or differently on each occurrence, from the group consisting of H, D, F, Cl, Br, CN, $N(Ar)_2$, $C(=O)Ar$, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which may be substituted by one or more radicals $R^1$, where one or more non-adjacent $CH_2$ groups may be replaced by O and where one or more H atoms may be replaced by D or F, an aromatic or heteroaromatic ring system having 5 to 30 aromatic ring atoms, which may in each case be substituted by one or more radicals $R^1$, an aryloxy or heteroaryloxy group having 5 to 30 aromatic ring atoms, which may be substituted by one or more radicals $R^1$, or a combination of these systems. At least one radical R here is a group of the formulae (3) to (9) as defined above.

In a particularly preferred embodiment of the invention, R is selected, identically or differently on each occurrence, from the group consisting of H, D, F, Cl, Br, CN, a straight-chain alkyl group having 1 to 10 C atoms or a branched or cyclic alkyl group having 3 to 10 C atoms, each of which may be substituted by one or more radicals $R^1$, where one or more H atoms may be replaced by D or F, an aromatic or heteroaromatic ring system having 5 to 18 aromatic ring atoms, which may in each case be substituted by one or more radicals $R^1$, or a combination of these systems. As described above, at least one of the substituents R here is selected from groups of the formulae (3) to (9).

In a further preferred embodiment of the invention, the symbols R which do not stand for a group of the formulae (3) to (6) and are not bonded to Y stand for H or D in compounds of the formulae (1), (2) and (16) to (18).

For compounds which are processed by vacuum evaporation, the alkyl groups preferably have not more than four C atoms, particularly preferably not more than 1 C atom. For compounds which are processed from solution, compounds which are substituted by alkyl groups having up to 10 C atoms or which are substituted by oligoarylene groups, for example ortho-, meta-, para- or branched terphenyl groups or quaterphenyl groups, are also suitable.

In a further preferred embodiment, two indices n in the compounds of the formula (1) or (2) are equal to 1 and the third index n is 0 or 1, where n=0 means that a hydrogen or radical $R^1$ is present instead of Y. It is furthermore preferred in compounds of the formulae (16) to (24) if one index n=1 and the second index n=0 or 1. This in each case relates to a unit of the formula (1). In compounds of the formula (2), this applies correspondingly to each moiety which is bonded to L.

In a further preferred embodiment of the invention, the index p=2 or 3, particularly preferably 2.

As described above, at least one of the radicals R stands for a group of the above-mentioned formulae (3) to (6) or also stands for the formulae (7) to (9) where Y=NR, or L stands for a group of the formulae (10) to (15). This group R may either be bonded to one of the phenyl rings of the basic structure or to the group Y. In a preferred embodiment of the invention, the group R of the formulae (3) to (6) is bonded to one of the phenyl rings of the basic structure. In a further preferred embodiment of the invention, the group R in the formulae (3) to (9) is bonded to the group Y if Y stands for N(R).

In a further preferred embodiment, one or two groups R stand for a group of the formulae (3) to (6), particularly preferably precisely one group R.

Particular preference is therefore given to the compounds of the following formulae (25) to (58):

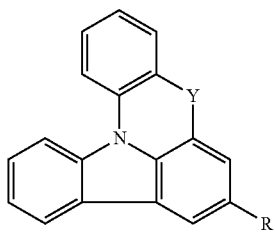

formula (25)

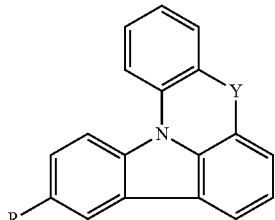

formula (26)

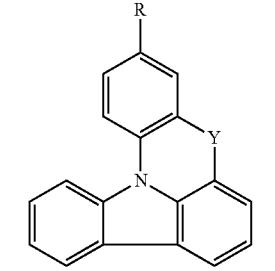

formula (27)

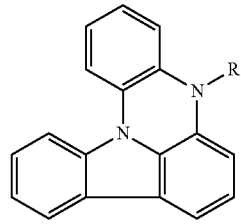

formula (28)

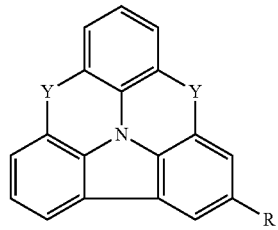

formula (29)

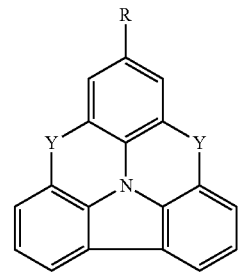

formula (30)

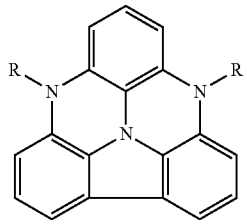

formula (31)

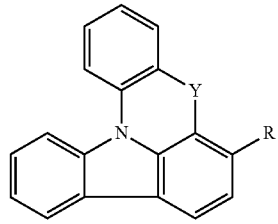

formula (32)

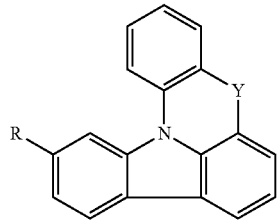

formula (33)

formula (34)
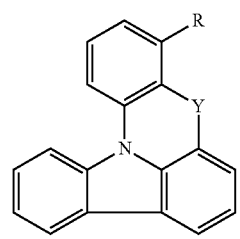
formula (35)
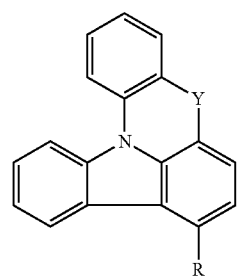
formula (36)
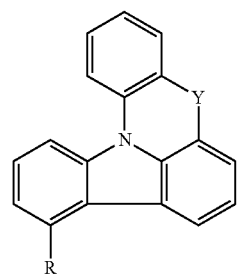
formula (37)
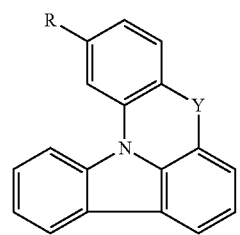
formula (38)
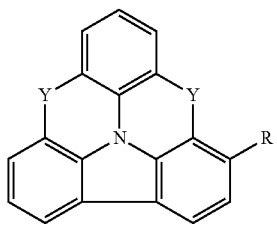
formula (39)
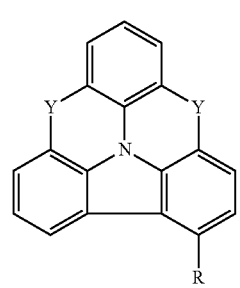
formula (40)
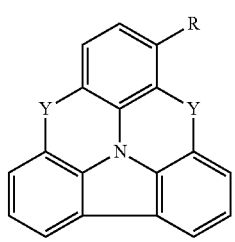
formula (41)
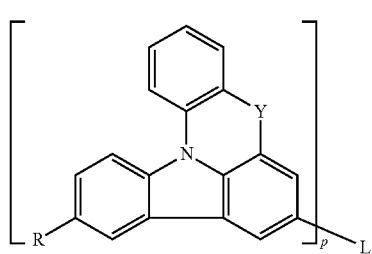
formula (42)
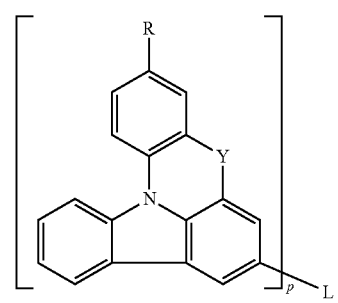
formula (43)
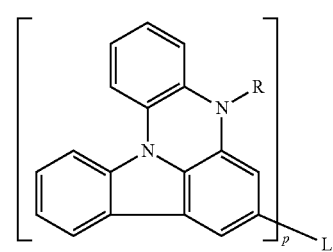
formula (44)
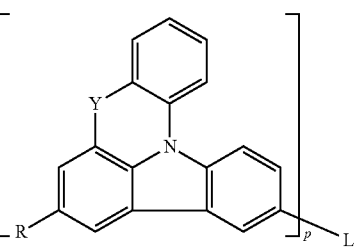
formula (45)
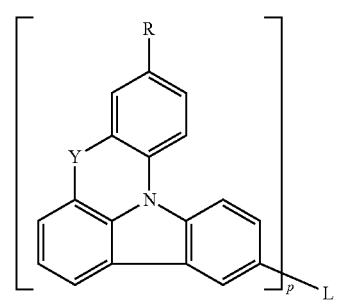

formula (46)
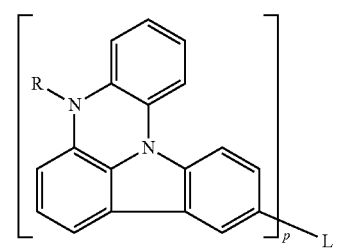
formula (47)
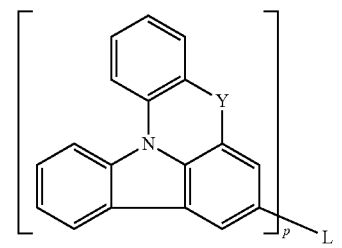
formula (48)
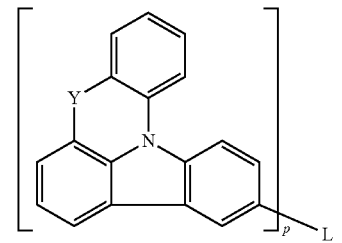
formula (49)
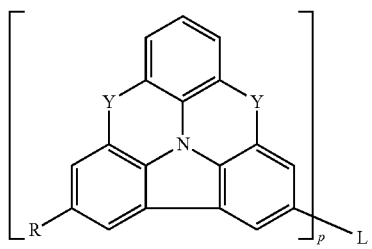
formula (50)
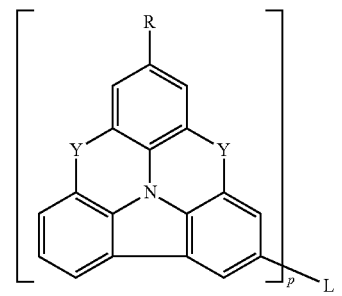
formula (51)
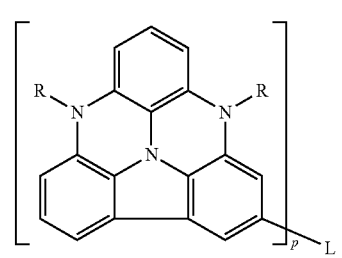
formula (52)
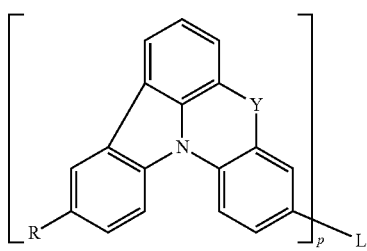
formula (53)
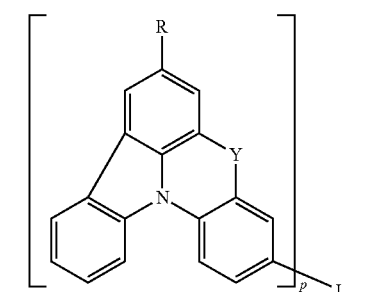
formula (54)
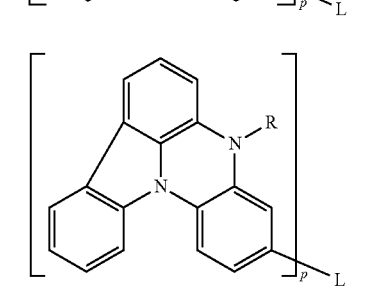
formula (55)
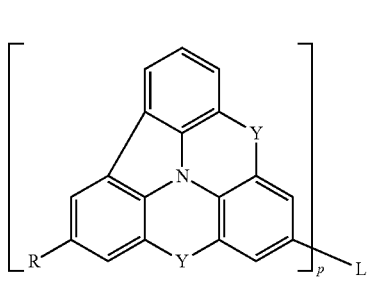
formula (56)
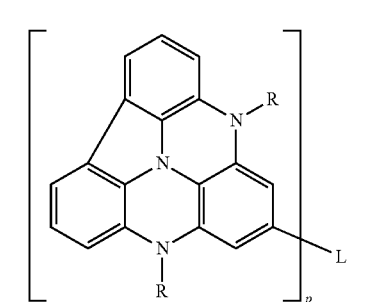
formula (57)
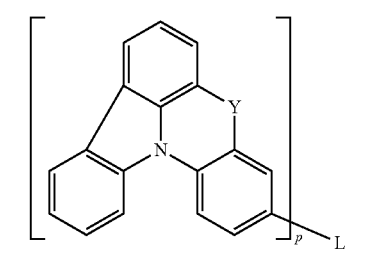

-continued formula (58)

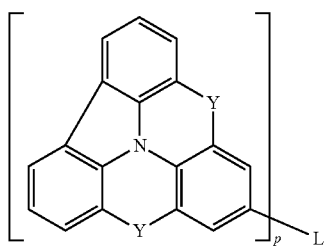

where R represents a group of one of the formulae (3) to (6) or, in formulae (28), (31), (42), (46), (51), (54) and (56), also a group of one of the formulae (7) to (9), and where L in formulae (47), (48), (57) and (58) represents a group of one of the formulae (10) to (15), Y stands, identically or differently, preferably identically, on each occurrence, for $C(R)_2$ or NR, where R which is bonded in the $C(R)_2$ or NR group stands, identically or differently on each occurrence, for an alkyl group having 1 to 10 C atoms or an aromatic or heteroaromatic ring system having 5 to 18 aromatic ring atoms, each of which may be substituted by one or more radicals $R^1$; furthermore, the C atoms drawn as unsubstituted may also be substituted by D instead of H, and the other symbols and indices have the meanings given above.

In particular, R which is bonded in the $C(R)_2$ or NR group preferably stands for the preferred groups mentioned above.

Preference is furthermore given to the compounds of the formulae (1) and (2) in which two groups Y stand for single bonds, i.e. compounds of the following formulae (59) to (82):

formula (59)

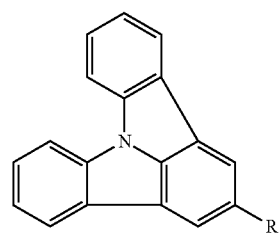

formula (60)

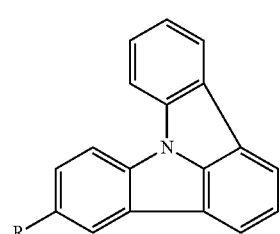

formula (61)

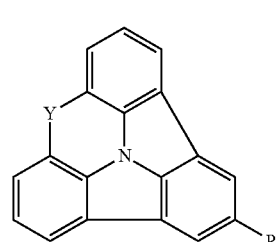

formula (62)

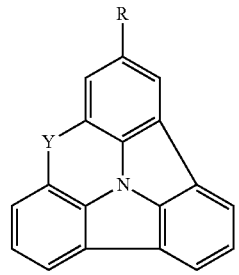

formula (63)

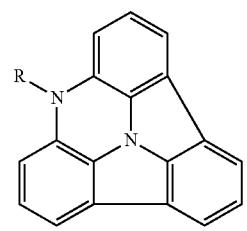

formula (64)

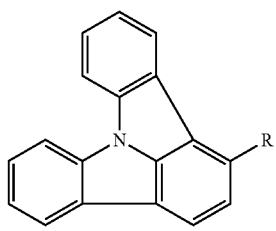

formula (65)

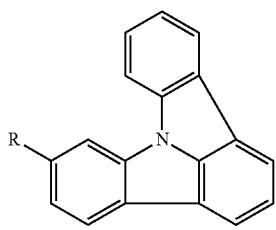

formula (66)

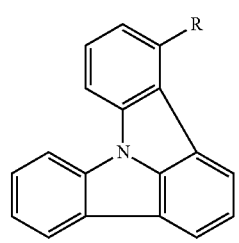

formula (67)

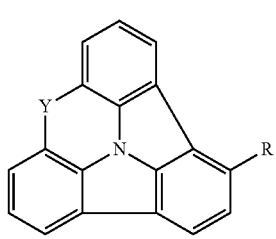

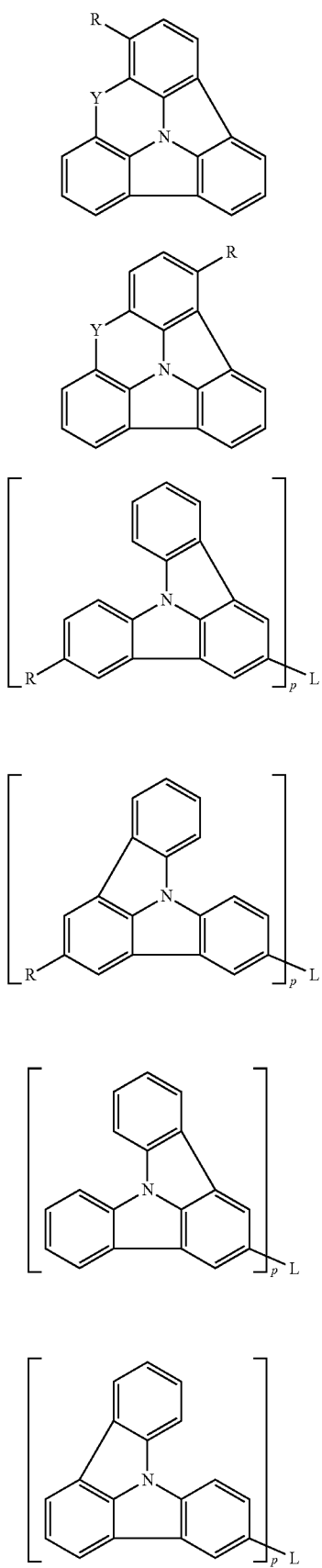
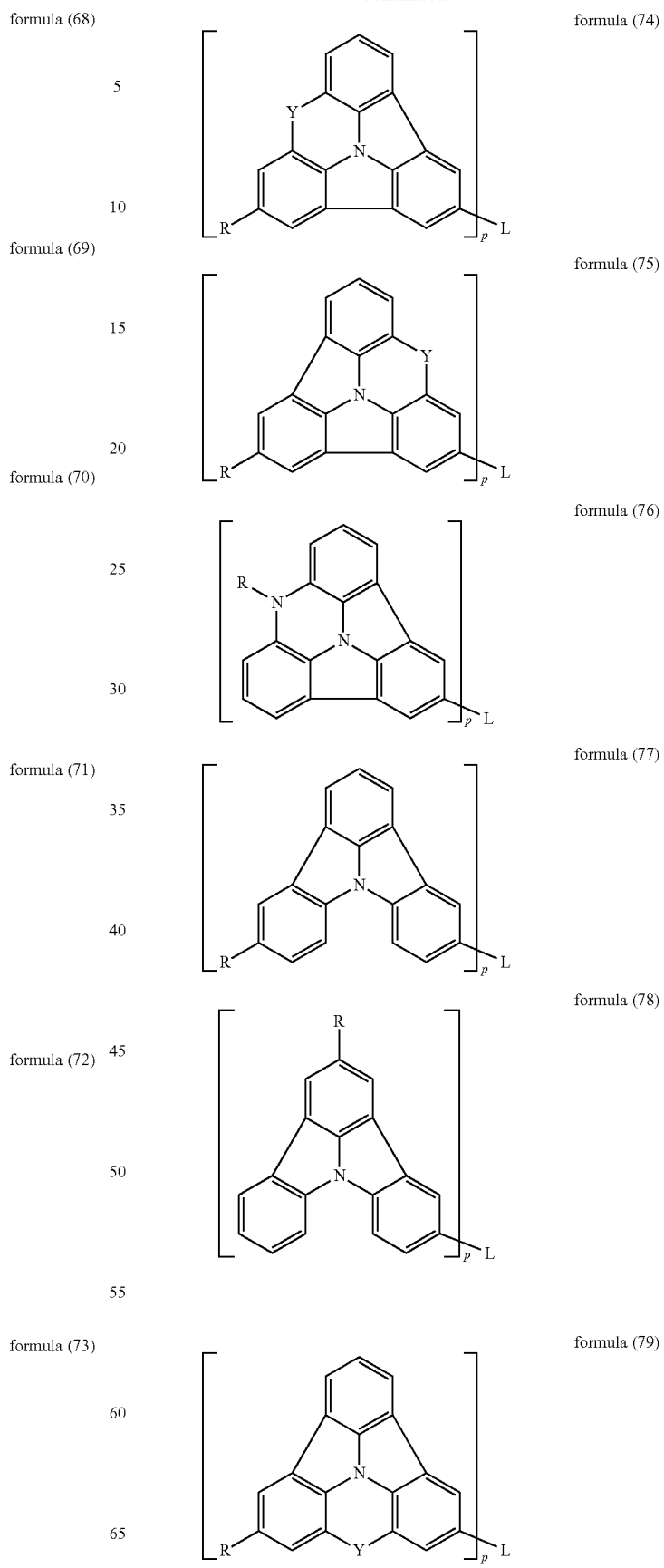

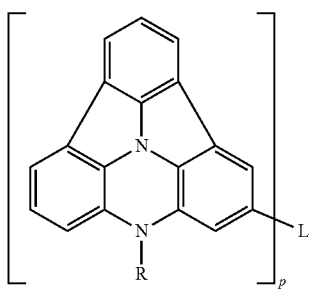
formula (80)

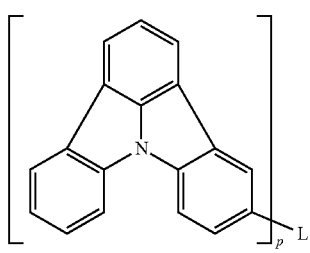
formula (81)

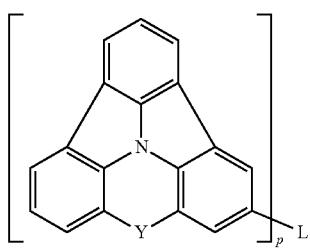
formula (82)

where R represents a group of one of the formulae (3) to (6) or, in the formulae (63) and (76), also represents a group of one of the formulae (7) to (9), and where L in formulae (72), (73), (81) and (82) represents a group of one of the formulae (10) to (15), Y stands, identically or differently, preferably identically, on each occurrence, for $C(R)_2$ or NR, where R which is bonded in the $C(R)_2$ or NR group stands, identically or differently on each occurrence, for an alkyl group having 1 to 10 C atoms or an aromatic or heteroaromatic ring system having 5 to 18 aromatic ring atoms, each of which may be substituted by one or more radicals $R^1$; furthermore, the C atoms drawn as unsubstituted may also be substituted by D instead of H, and the other symbols and indices have the meanings given above.

In a further preferred embodiment of the invention, the structures of the formulae (16) to (82) each contain a radical R other than H or D in the position para to the central atom X, i.e., in particular, para to the nitrogen. The substituents R in the para-position of X which do not stand for a group of the formulae (3) to (6) particularly preferably stand for an alkyl group having 1 to 10 C atoms, in particular having 1 to 4 C atoms, or for an aromatic or heteroaromatic ring system having 5 to 24 aromatic ring atoms, which may be substituted by one or more radicals $R^1$, in particular for a phenyl group, which may be substituted by one or more radicals $R^1$. This preference gives selective synthetic access to the compounds according to the invention.

In the structures of the formulae (3) to (15), the symbol $R^1$ preferably stands for an aromatic or heteroaromatic ring system having 5 to 20 aromatic ring atoms, which contains no condensed aromatic ring systems having more than 10 aromatic ring atoms and which may in each case be substituted by one or more radicals $R^2$, particularly preferably for phenyl, ortho-, meta- or para-biphenyl, ortho-, meta- or para-terphenyl, quaterphenyl or 1- or 2-naphthyl, each of which may be substituted by one or more radicals $R^2$.

In a further preferred embodiment of the invention, the group Ar in the formulae (3) to (15) stands for an aromatic or heteroaromatic ring system having 5 to 20 aromatic ring atoms, which contains no condensed aromatic ring systems having more than 10 aromatic ring atoms and which may be substituted by one or more non-aromatic radicals $R^1$. Ar in the formulae (3) to (15) particularly preferably stands for phenyl, ortho-, meta- or para-biphenyl, ortho-, meta- or para-terphenyl or quaterphenyl, each of which may be substituted by one or more non-aromatic radicals $R^1$, but is preferably unsubstituted.

Examples of preferred compounds in accordance with the embodiments indicated above or compounds as can preferably be employed in organic electronic devices are the compounds of the following structures.

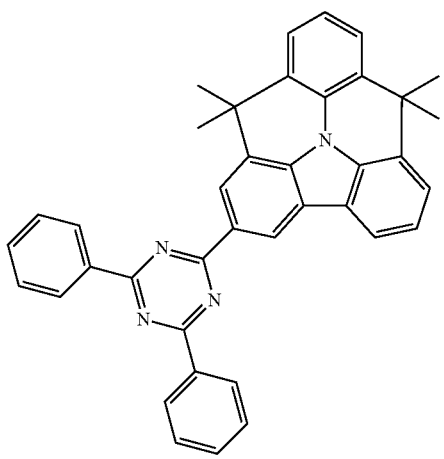

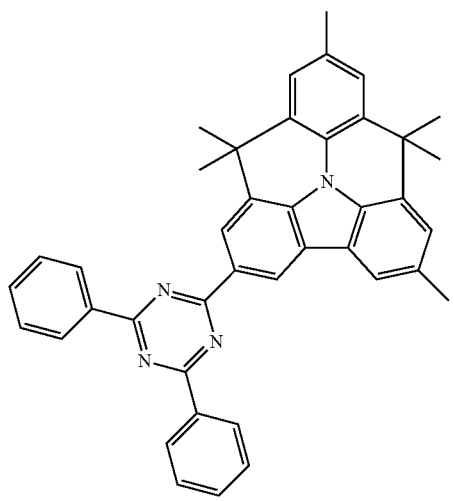

23
24
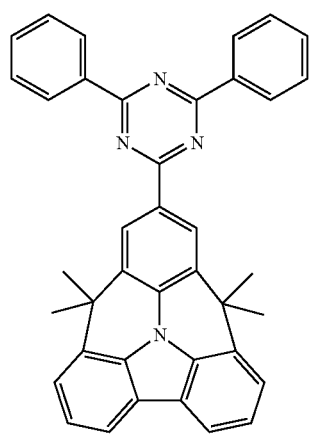
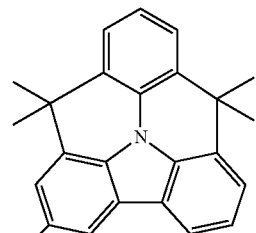
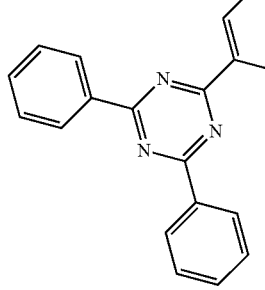
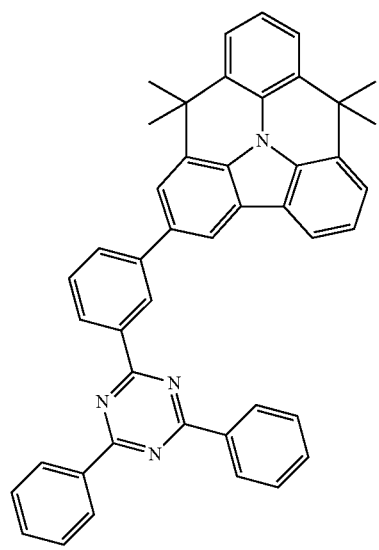
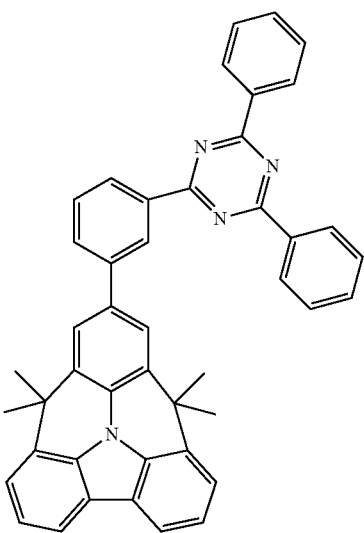
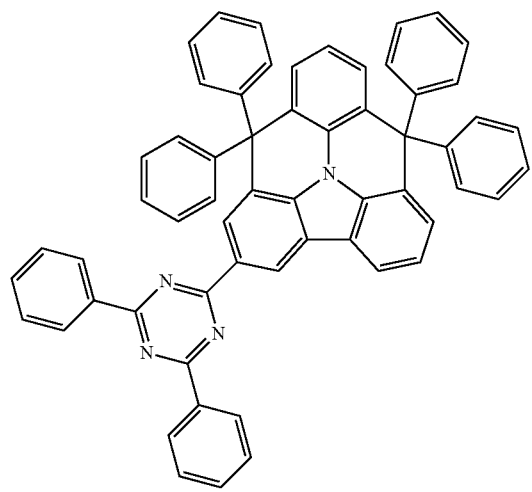
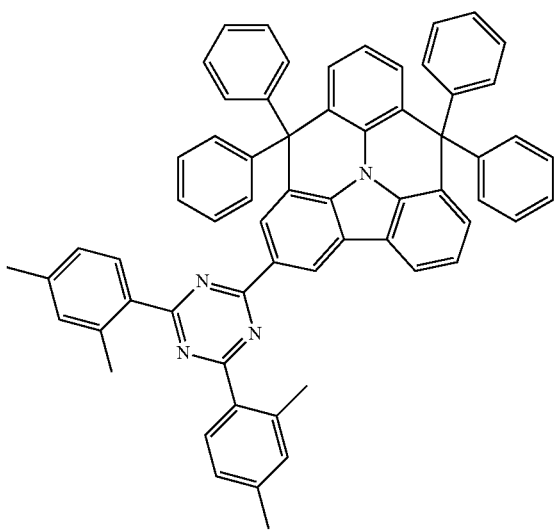

-continued
25
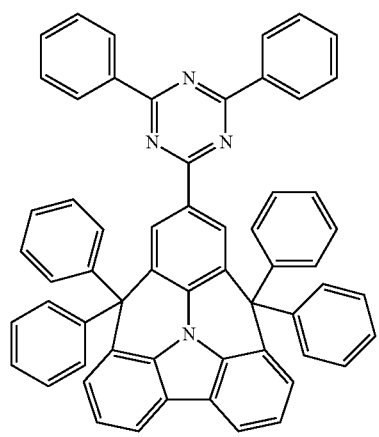
26
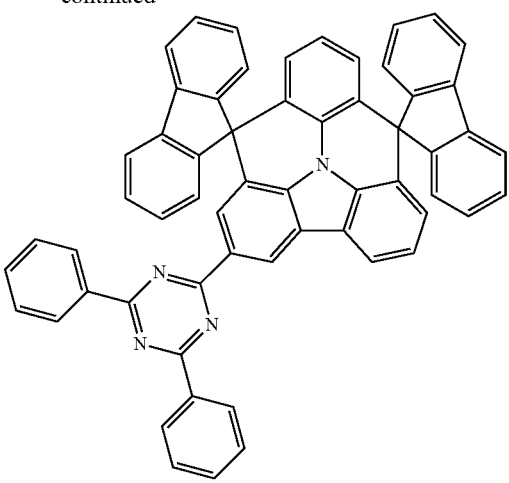
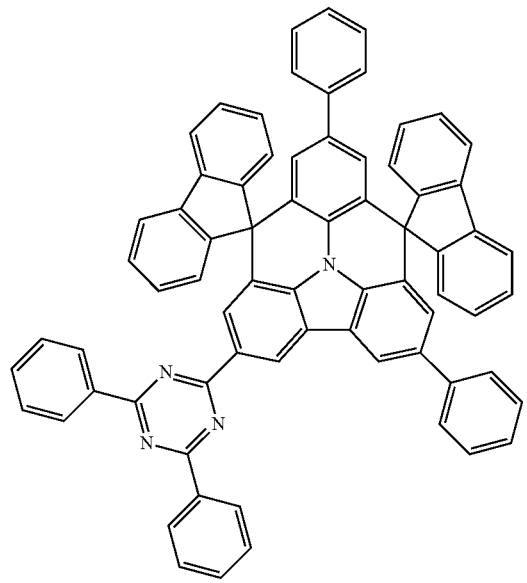
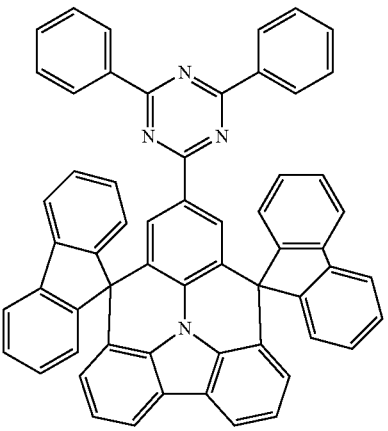
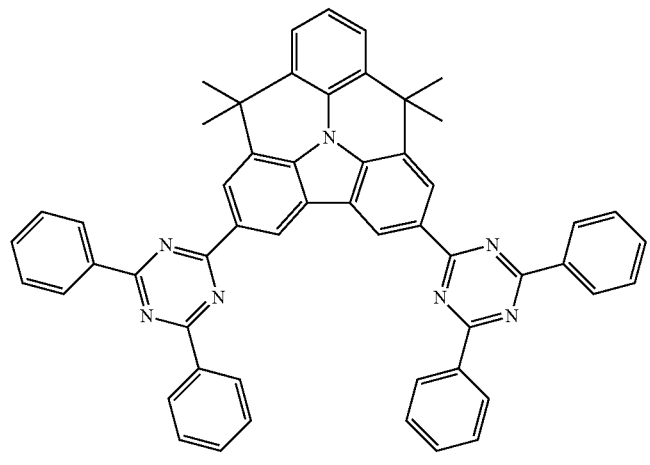
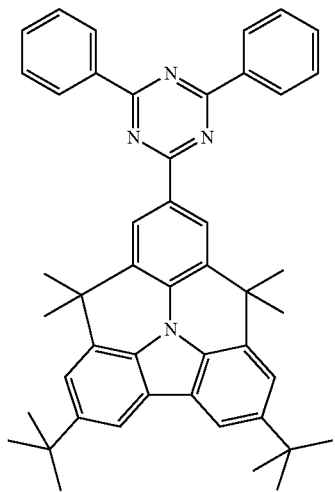

-continued
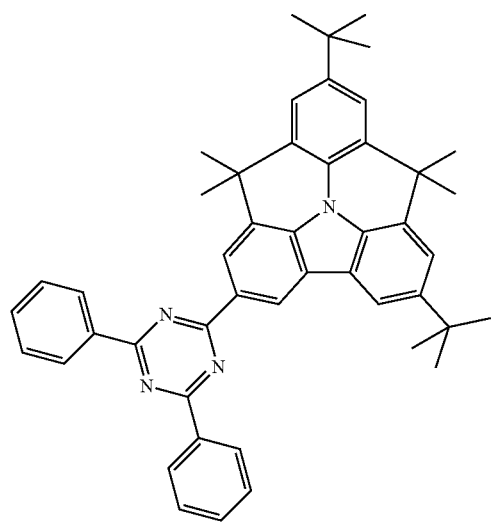
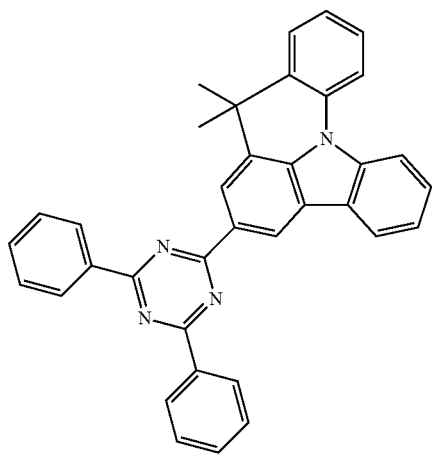
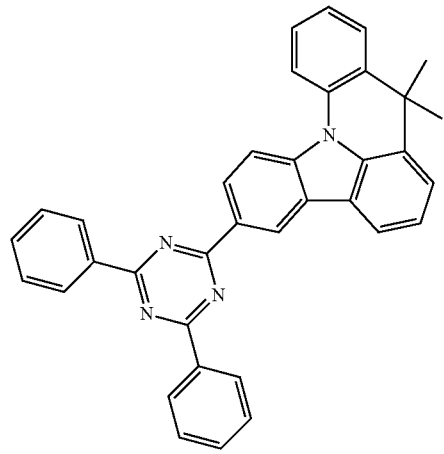
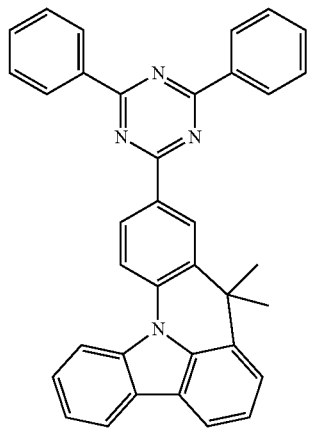
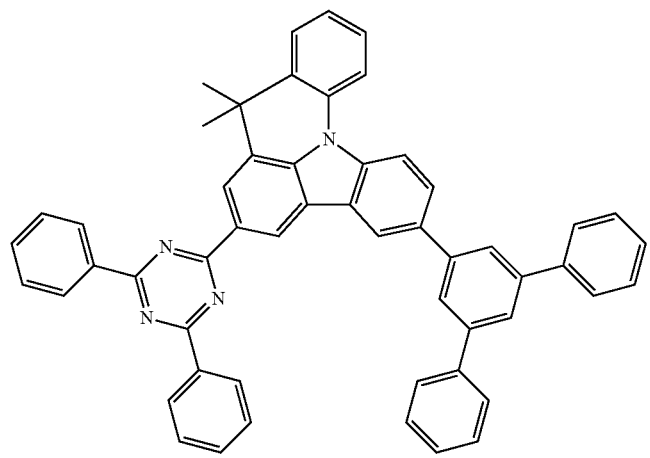
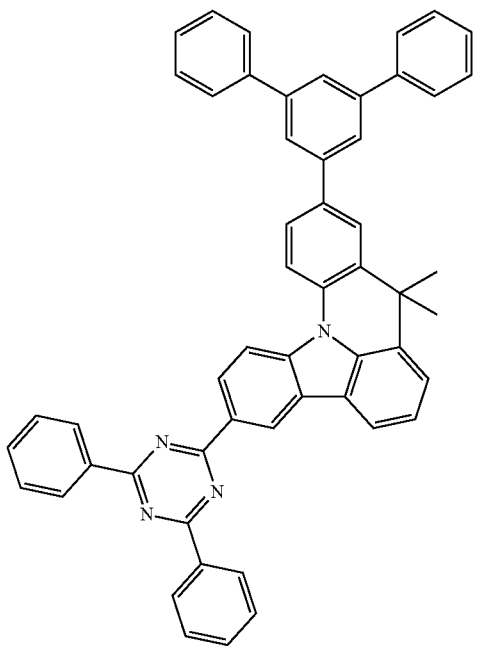

-continued
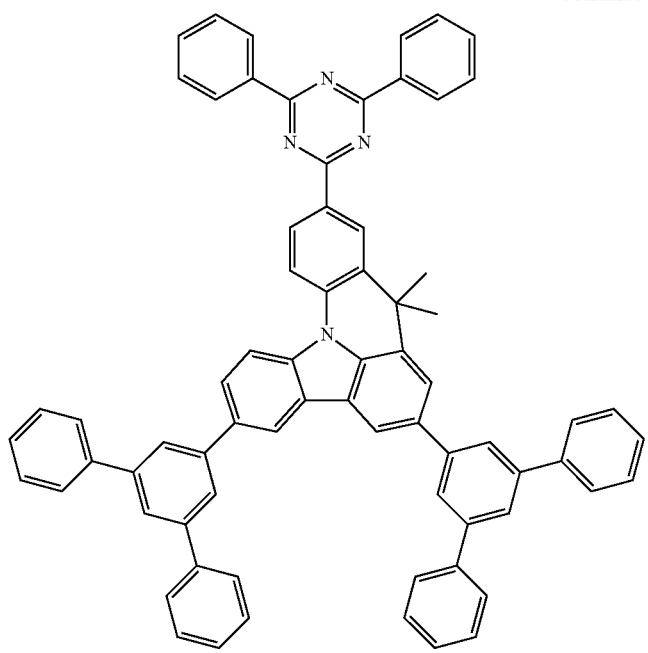
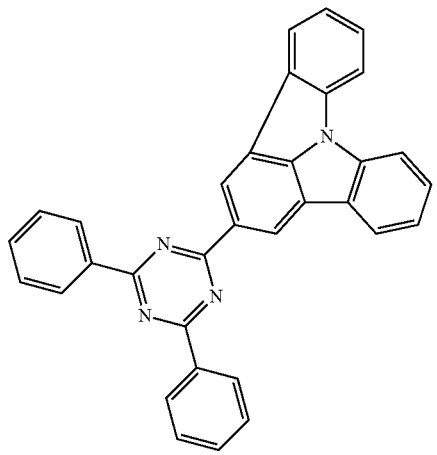
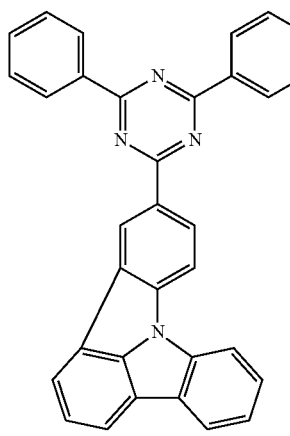
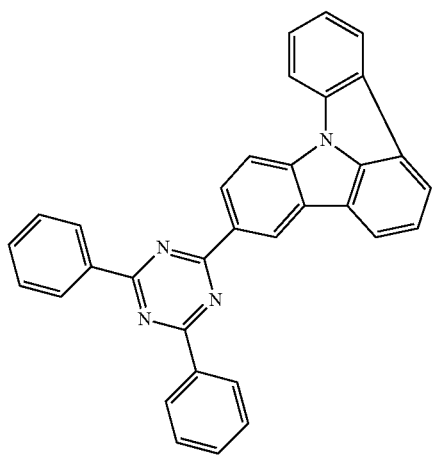
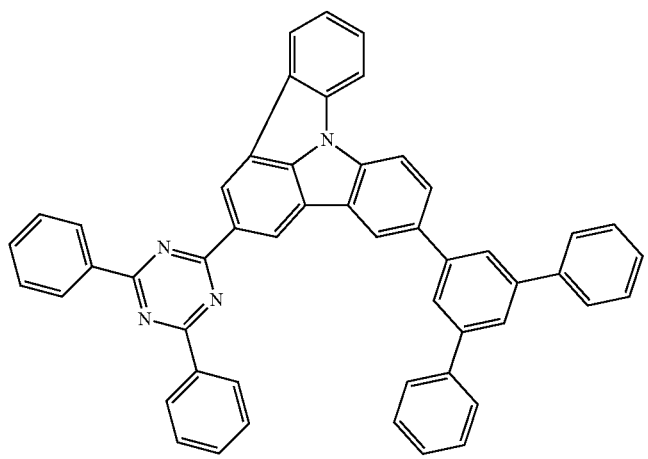
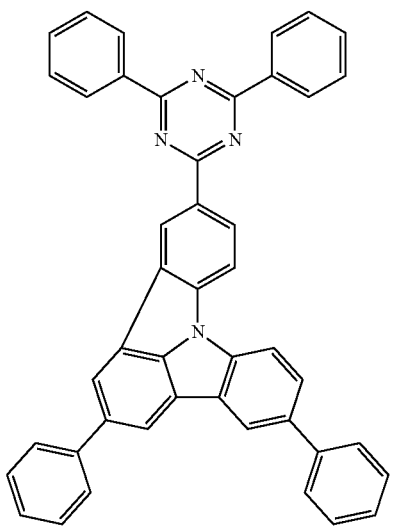

31
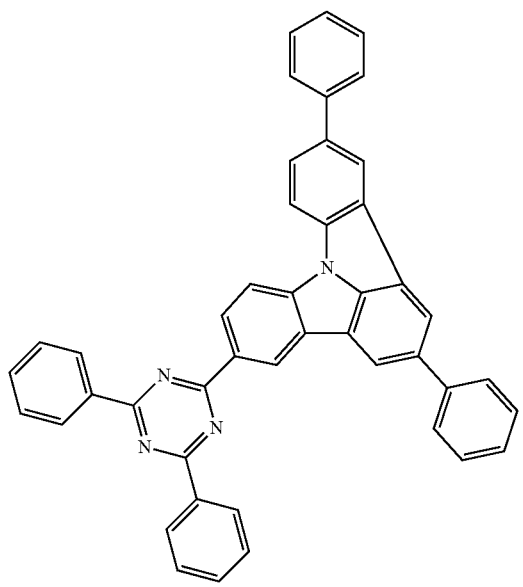
32
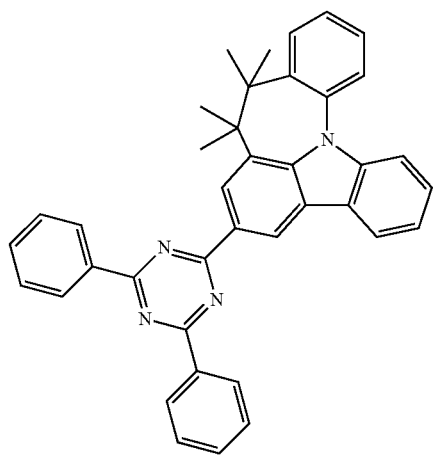
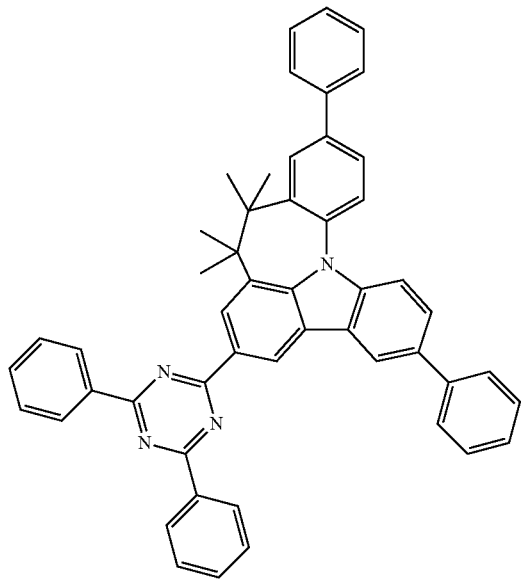
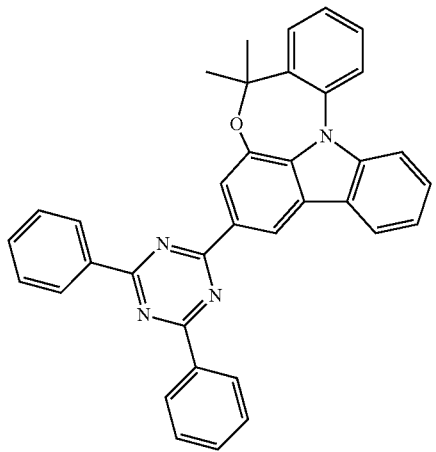

-continued
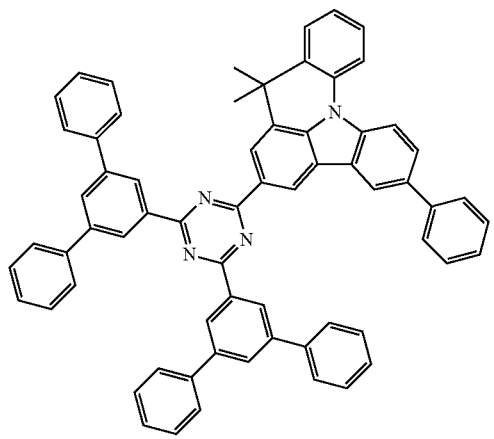
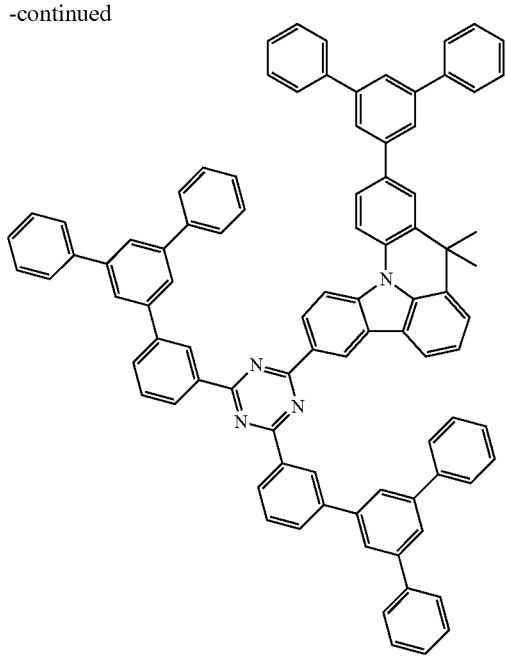
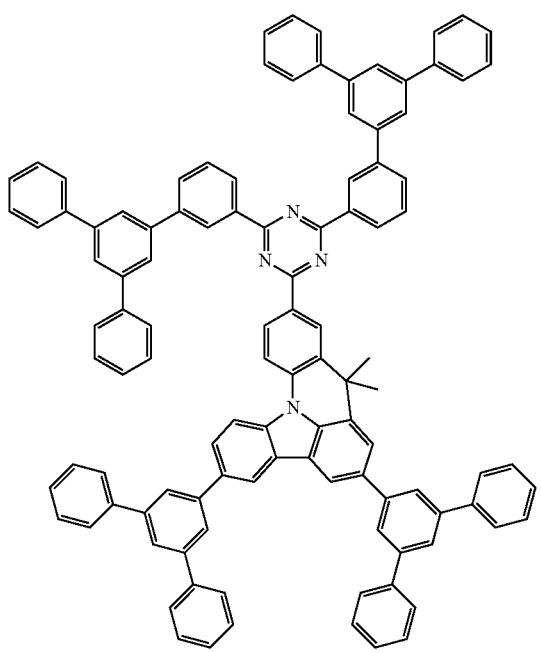
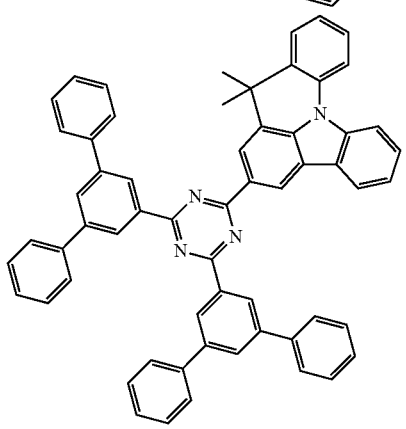
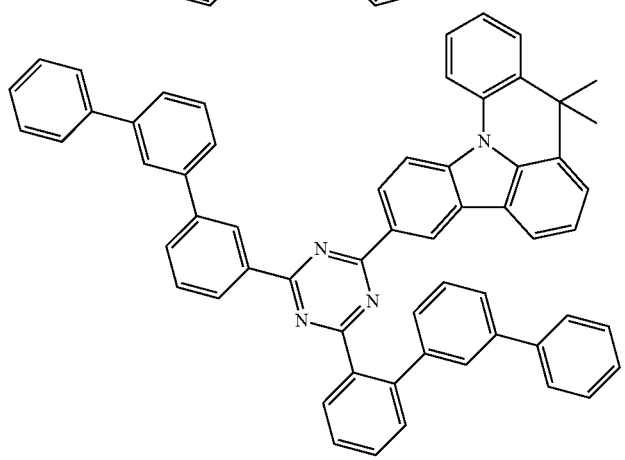

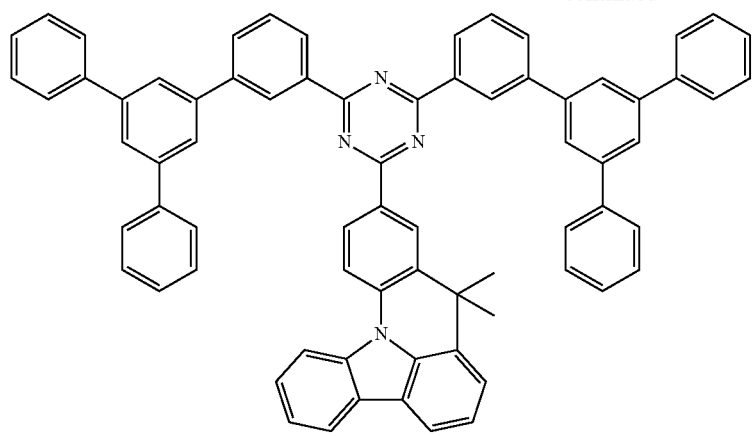
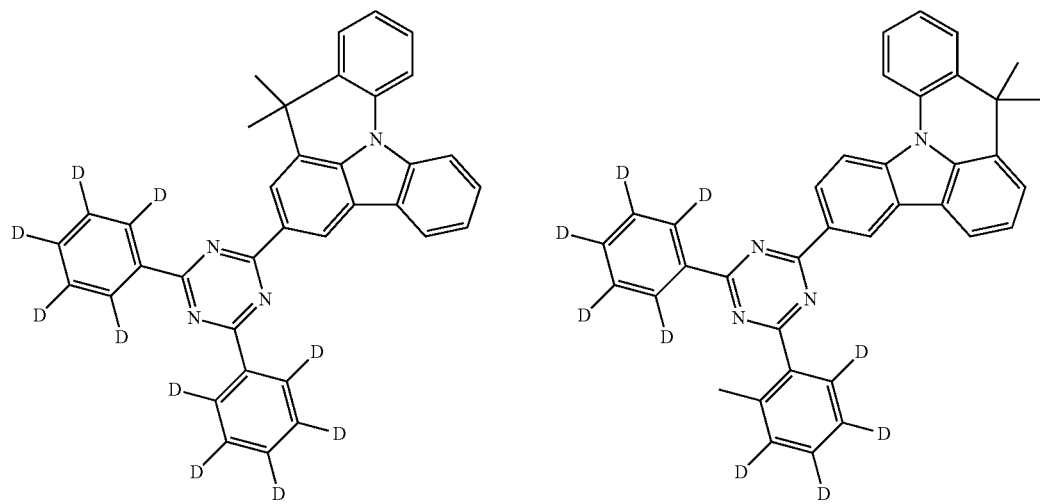
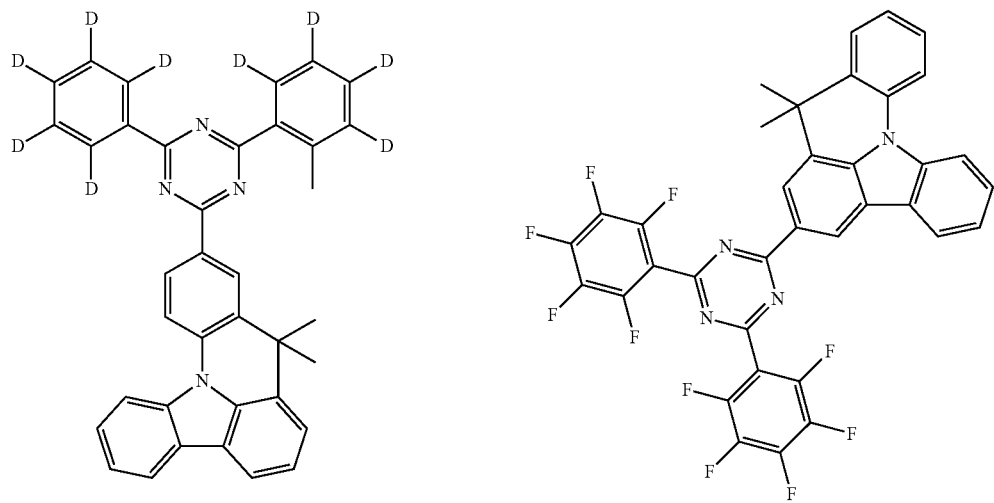

-continued
37
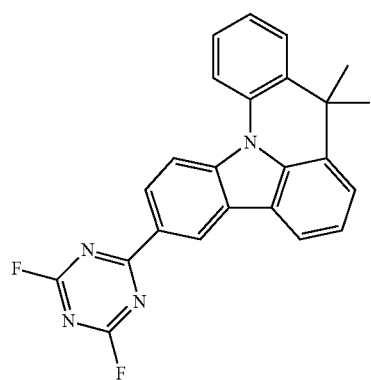
38
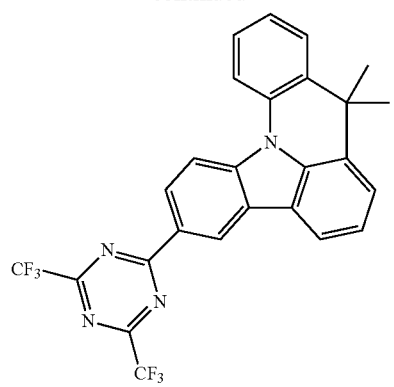
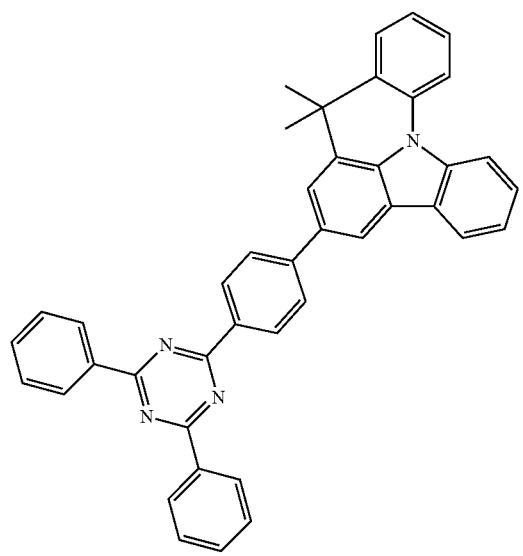
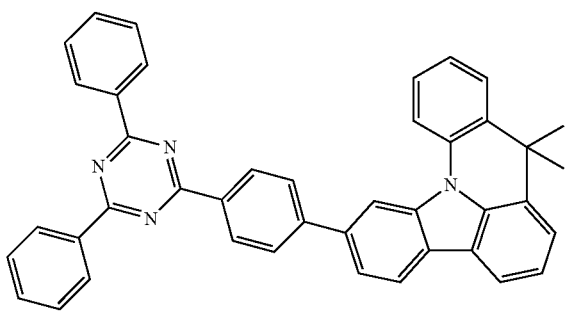
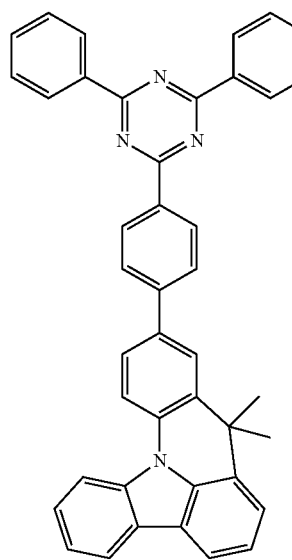
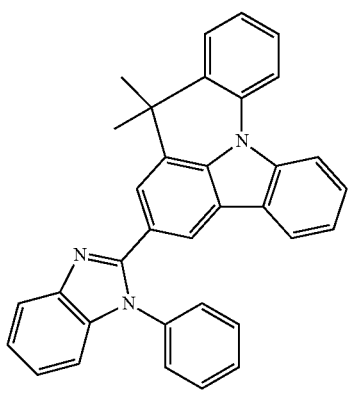
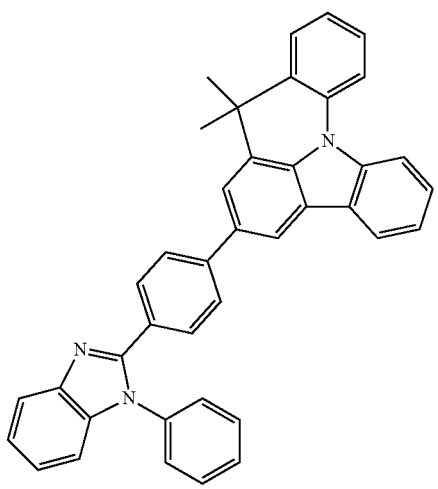

-continued
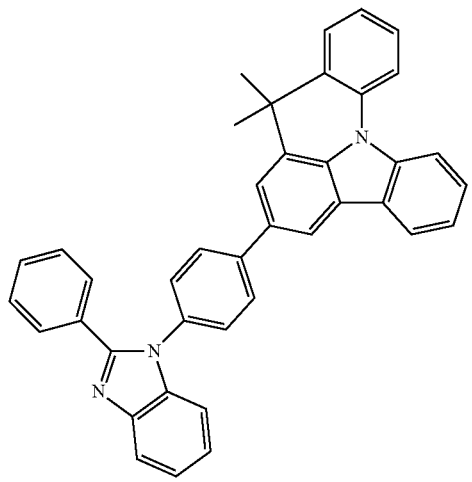
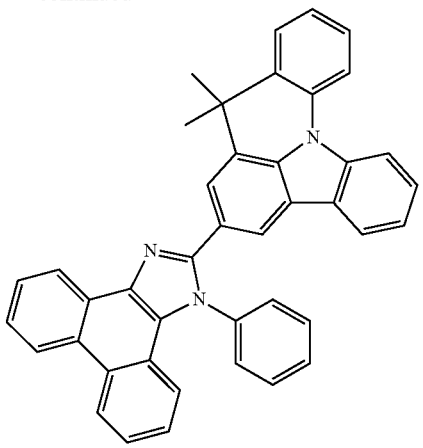
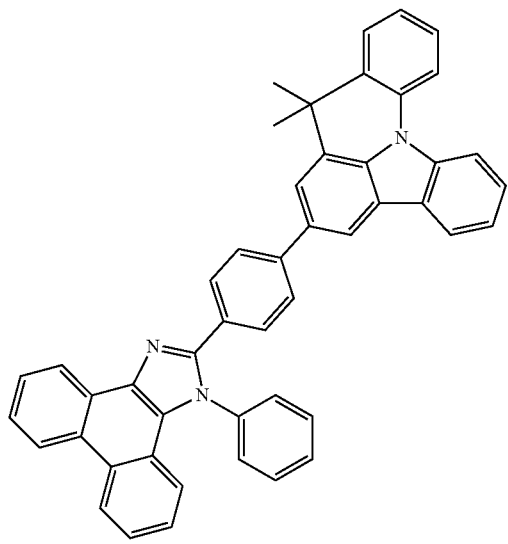
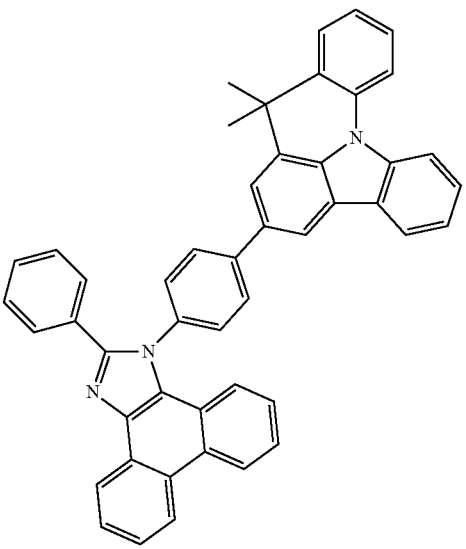
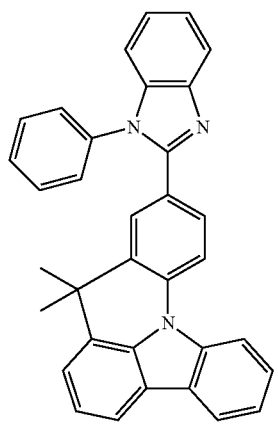
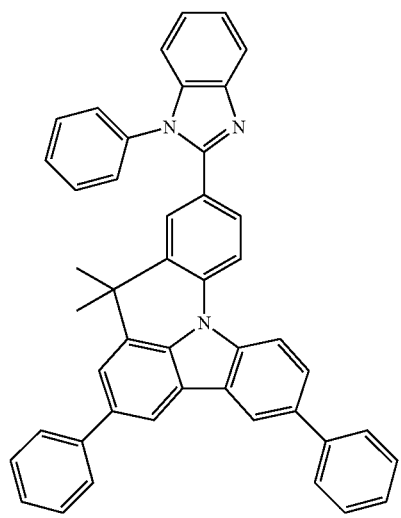
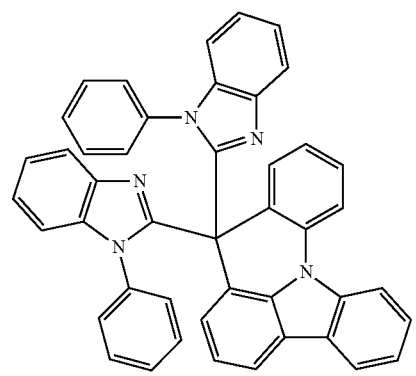

41
-continued
42
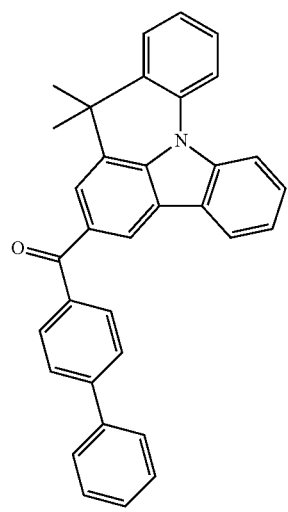 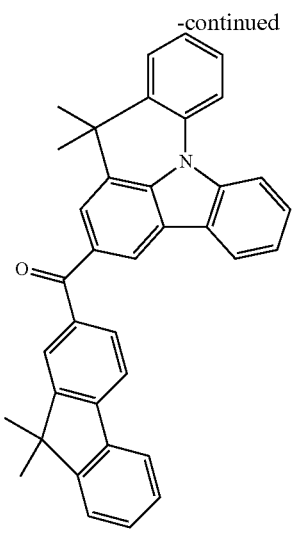 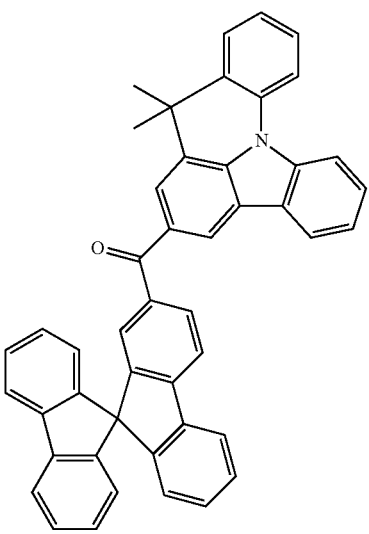
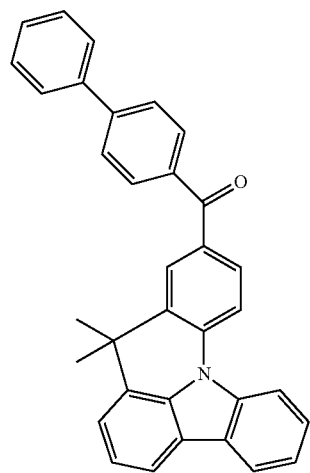 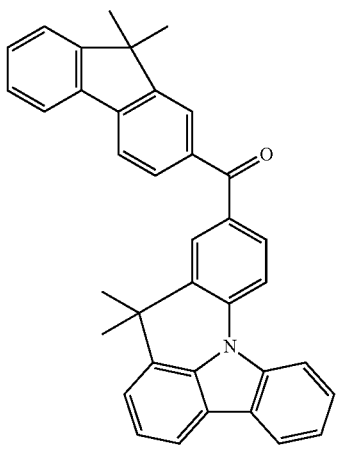 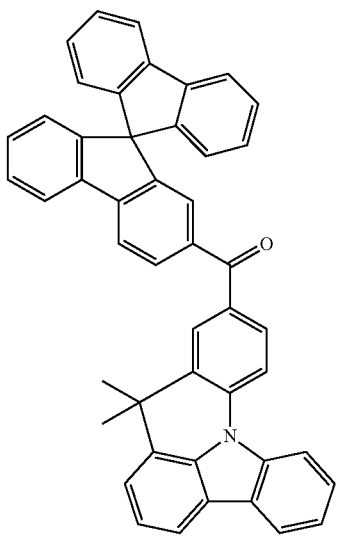
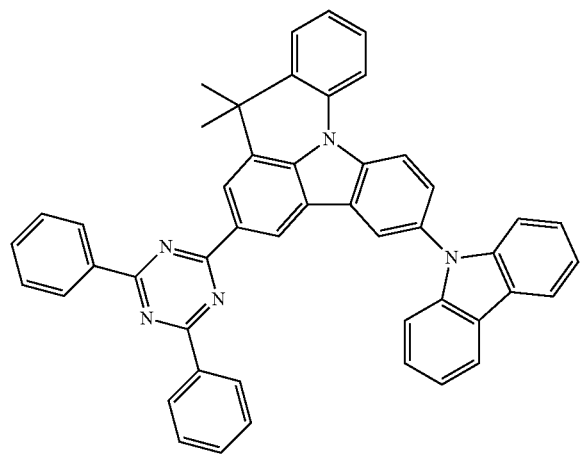

-continued
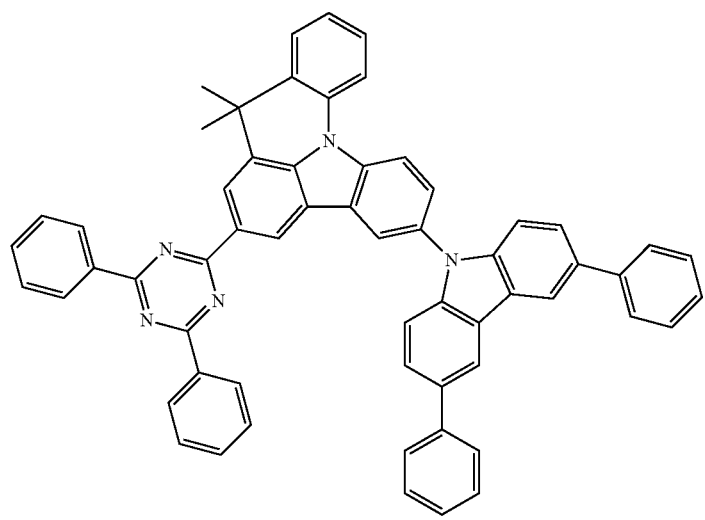
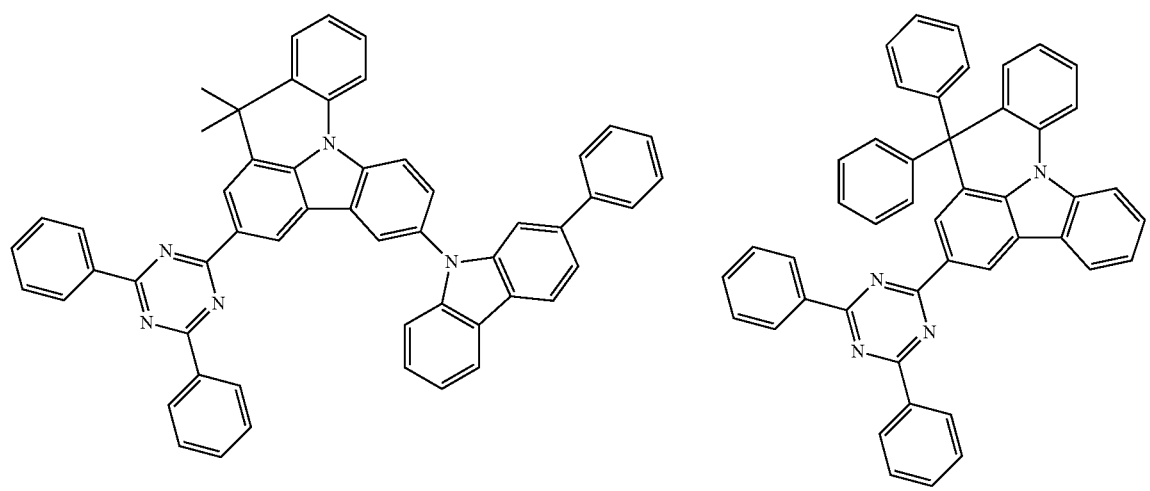
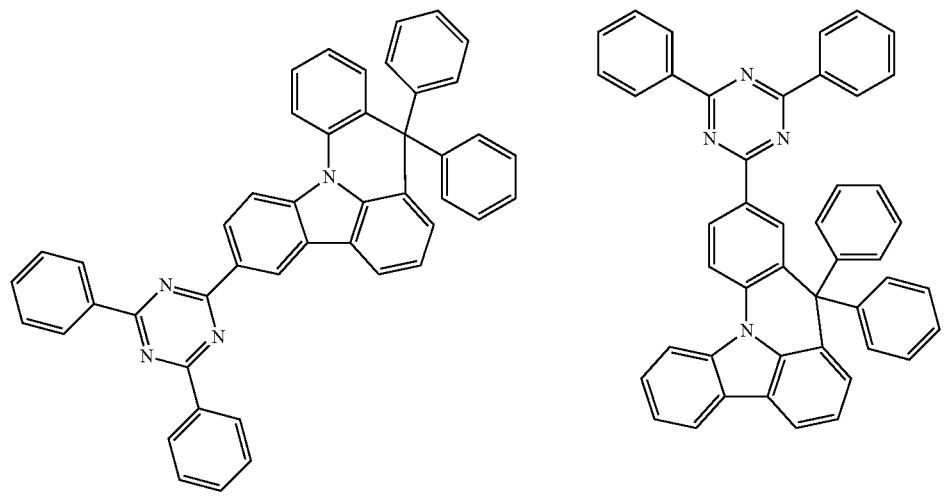

-continued
45
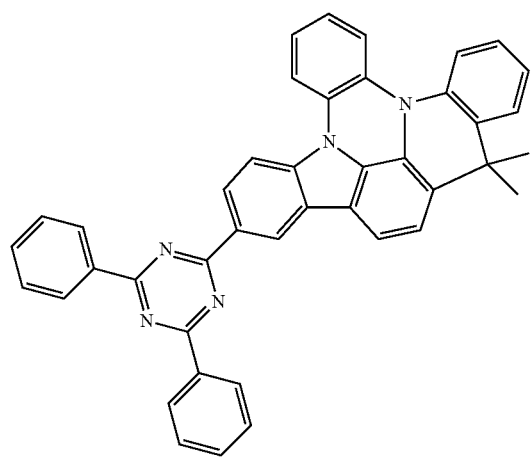
46
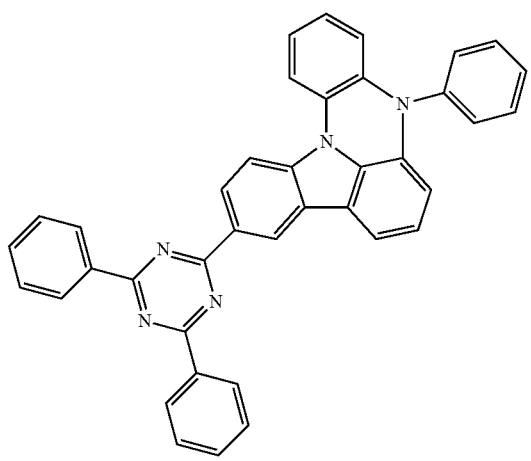
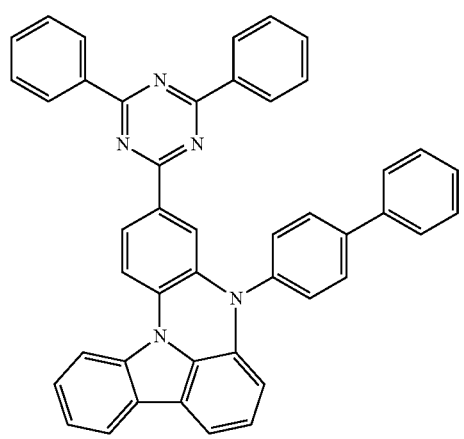
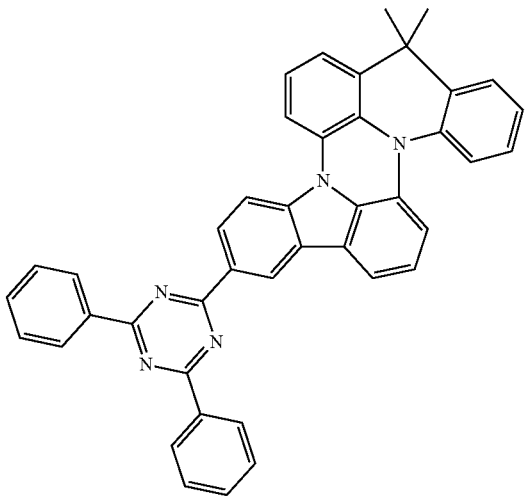
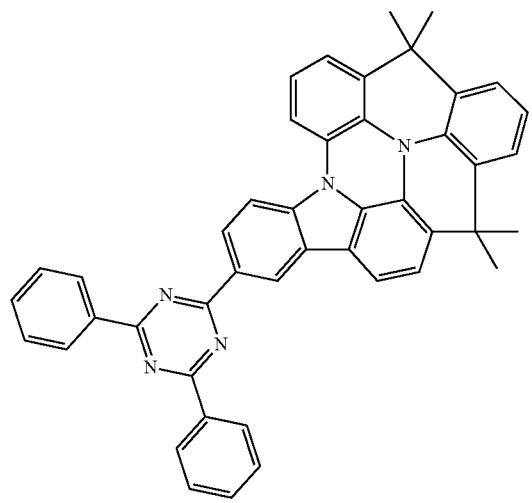
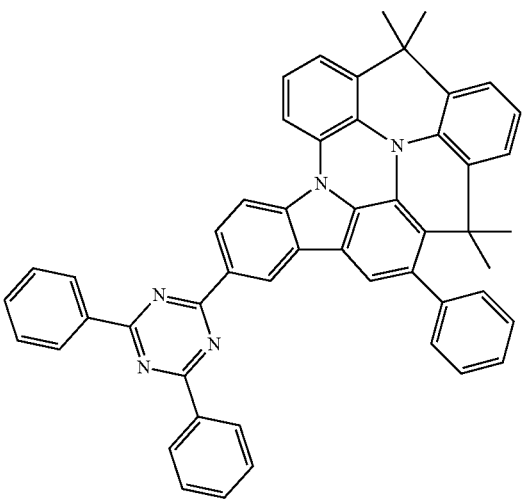

-continued
47
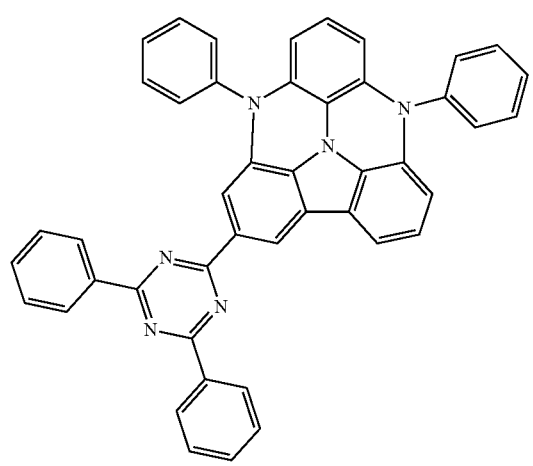
48
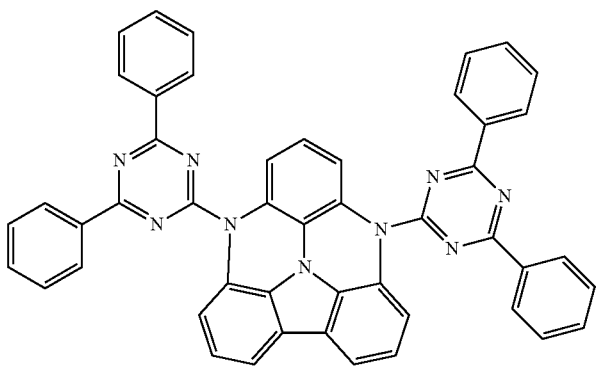
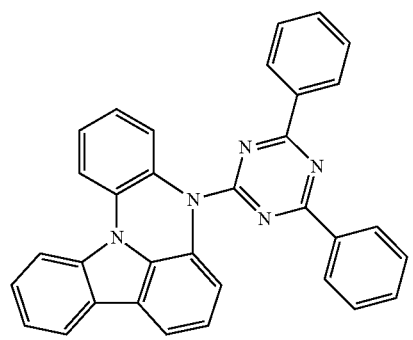
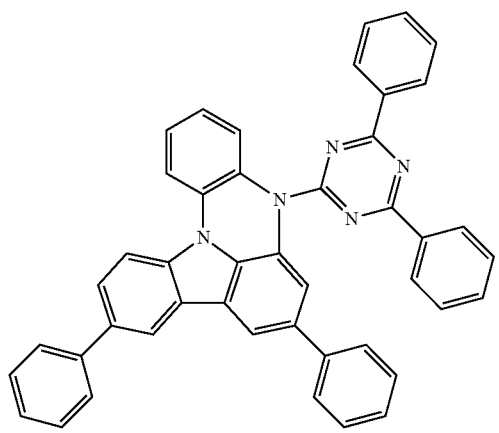
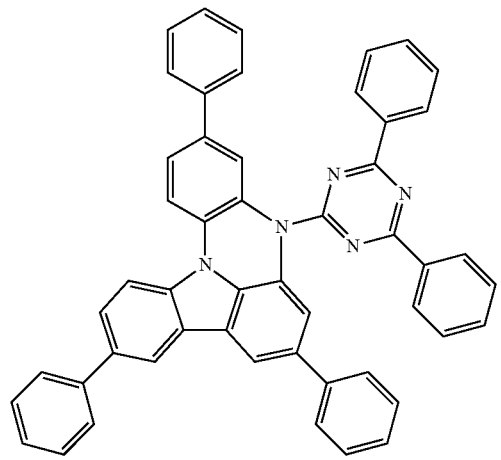
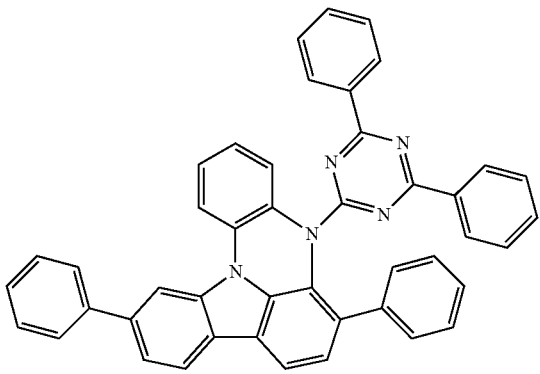

-continued
49
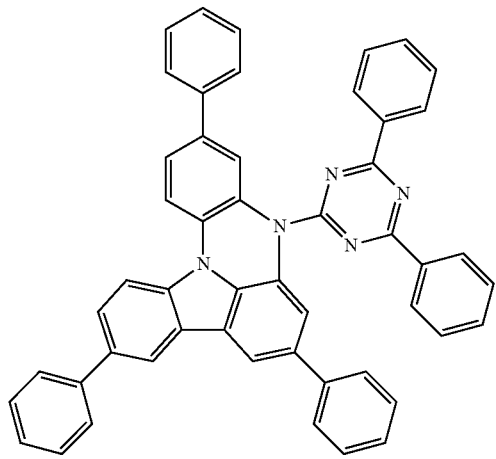
50
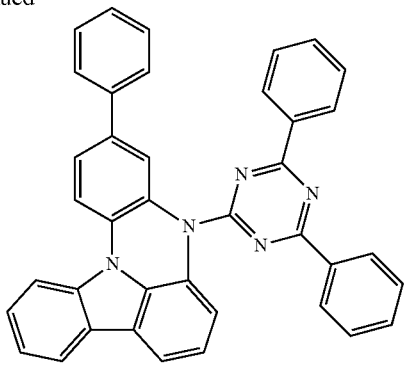
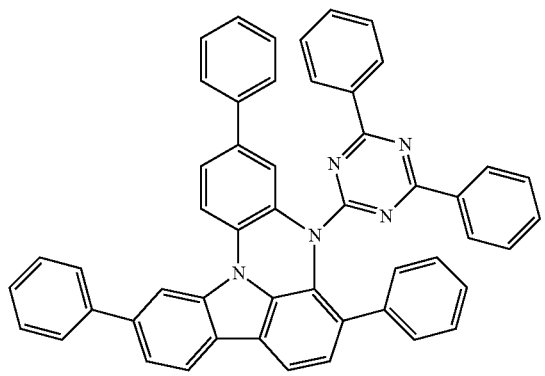
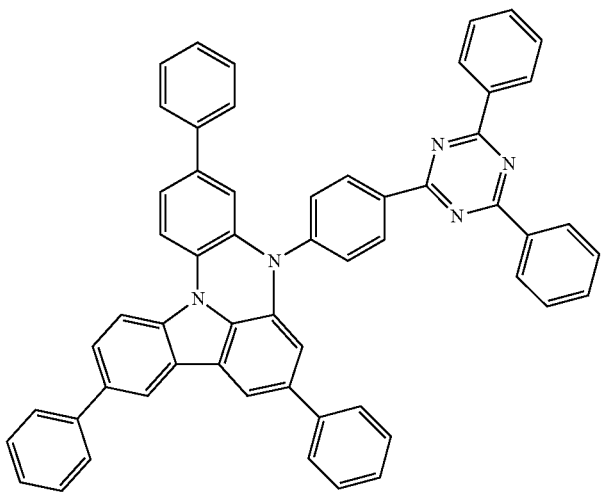
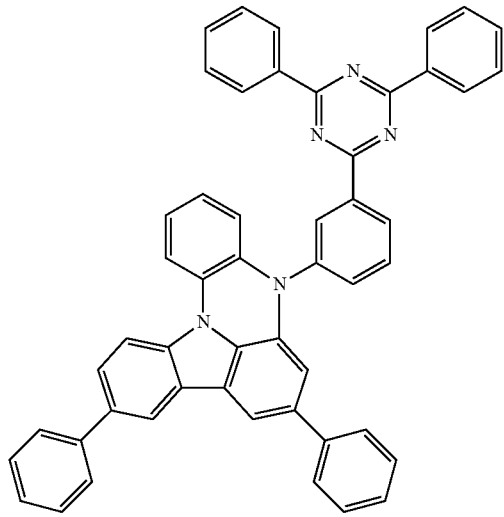
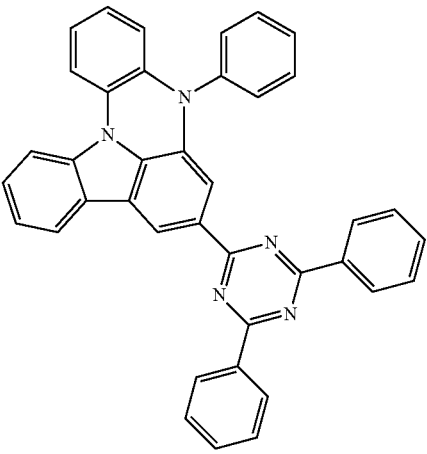

51
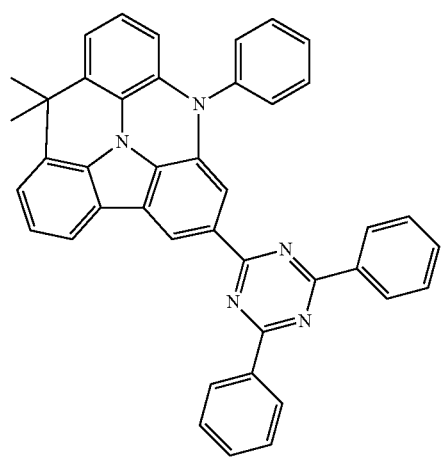
52
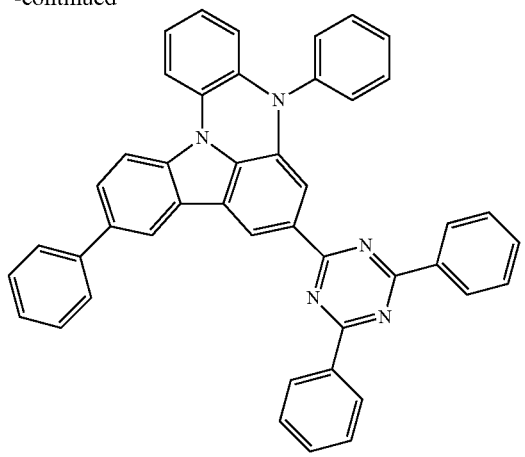
-continued
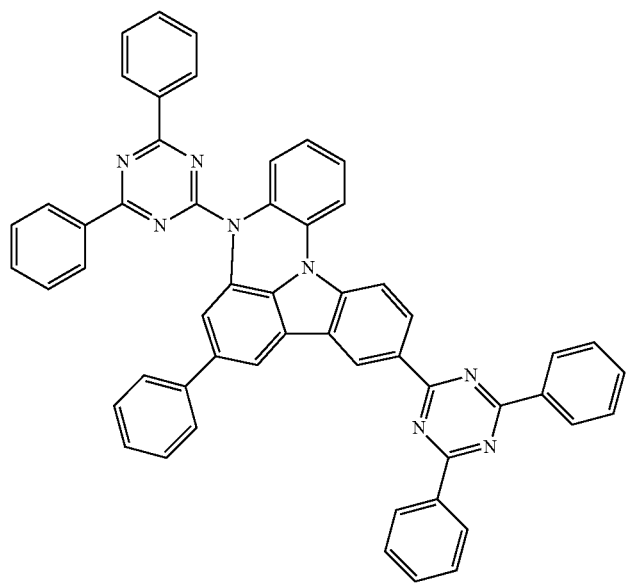
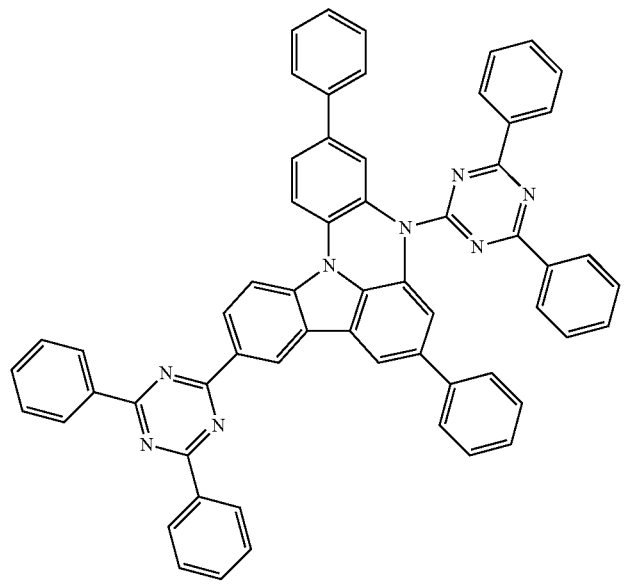

-continued
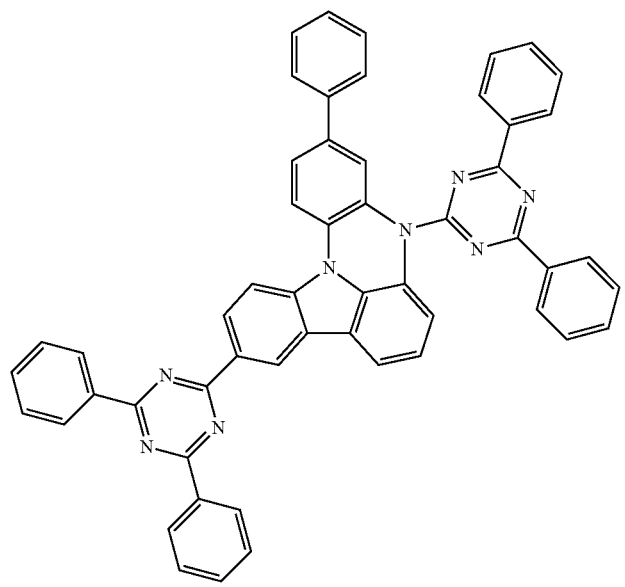
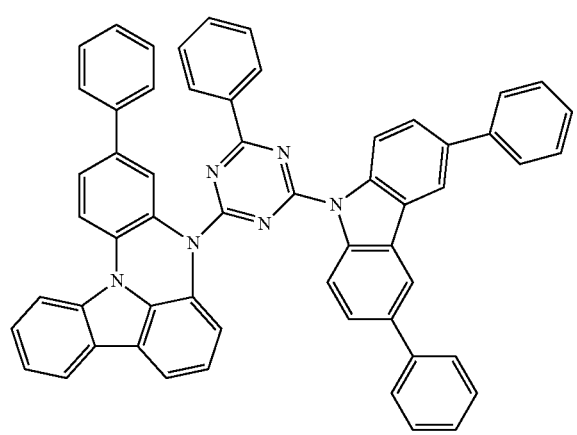
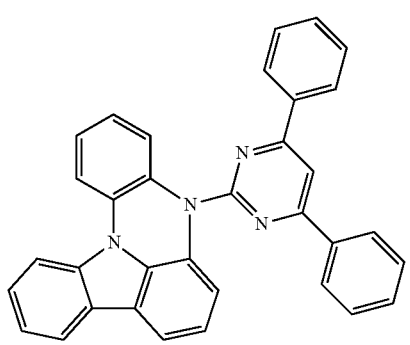
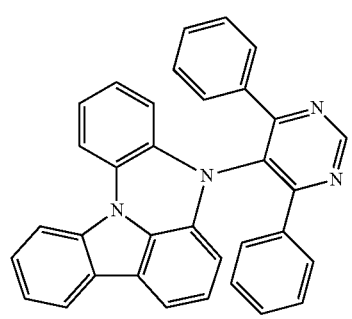
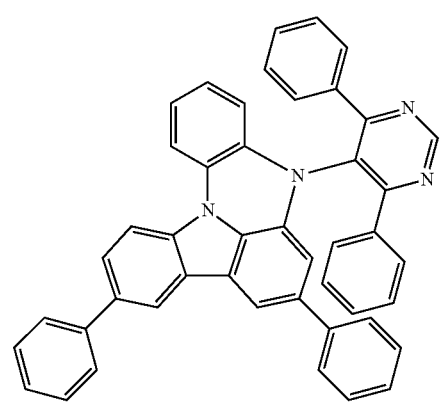

-continued
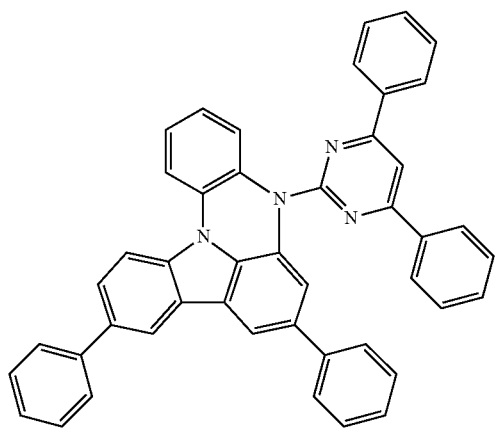
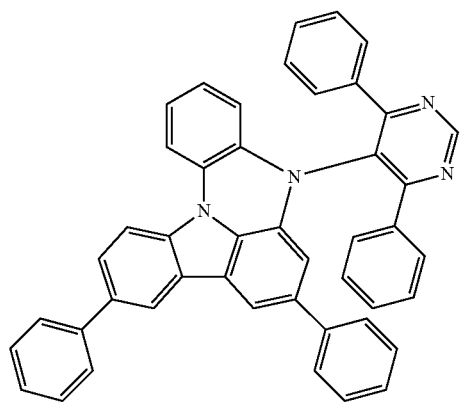
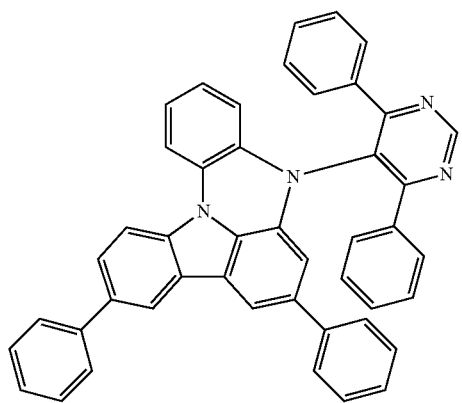
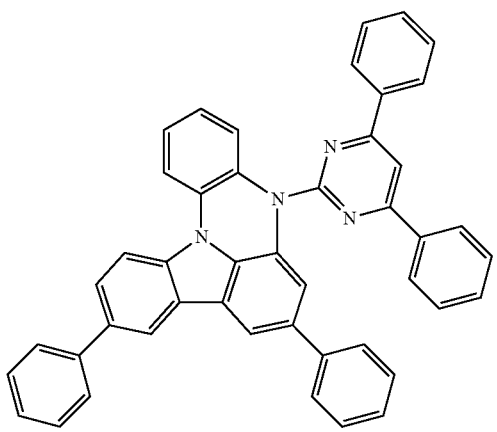
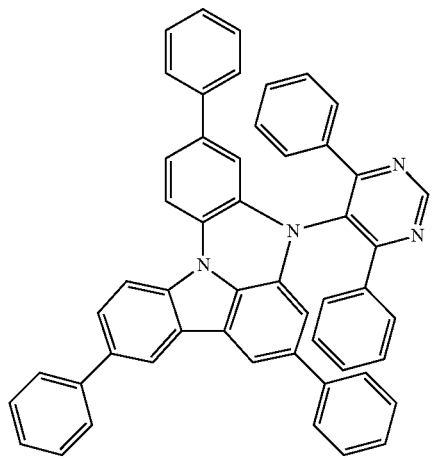
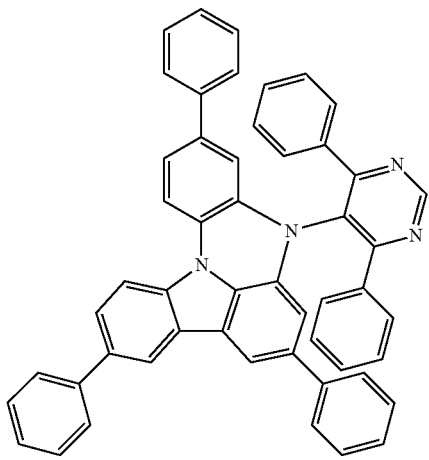

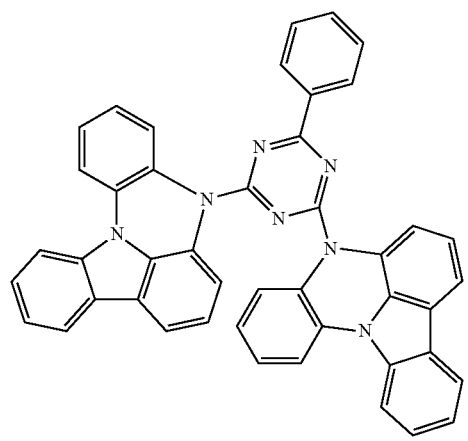
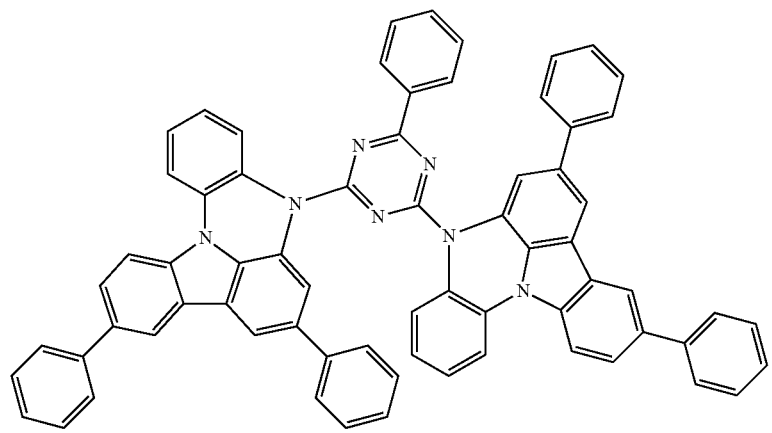
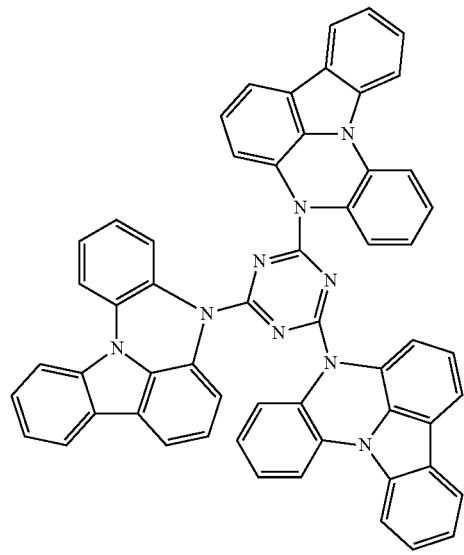
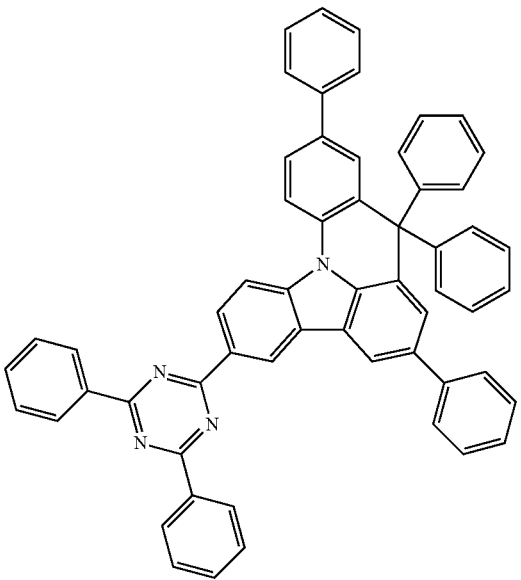

59
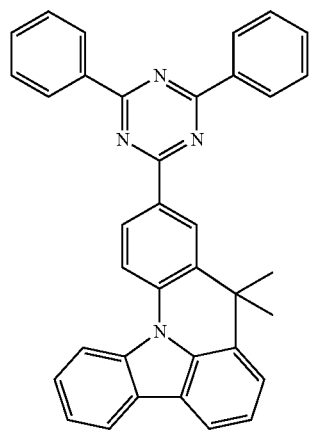
-continued
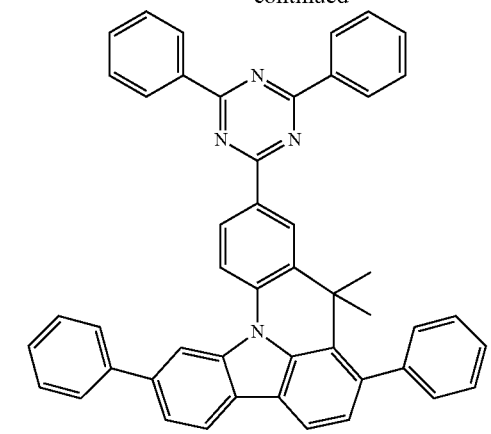
60
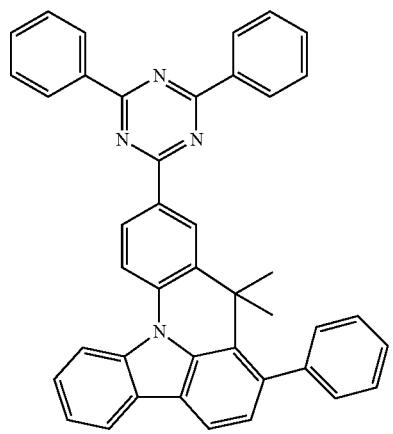
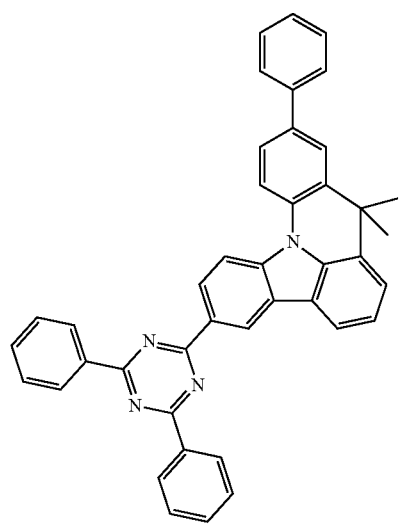
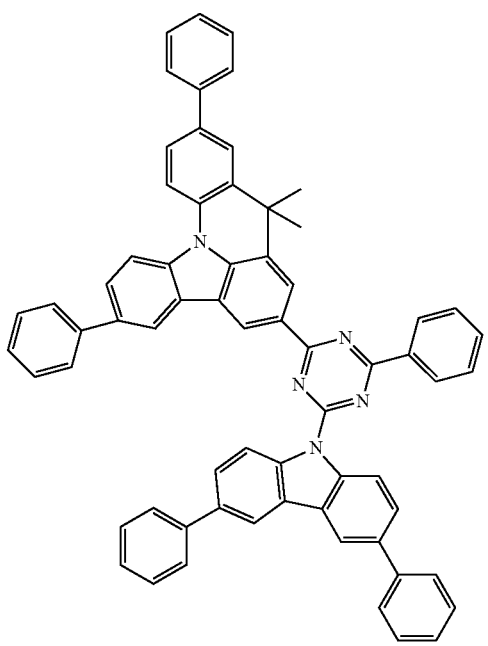
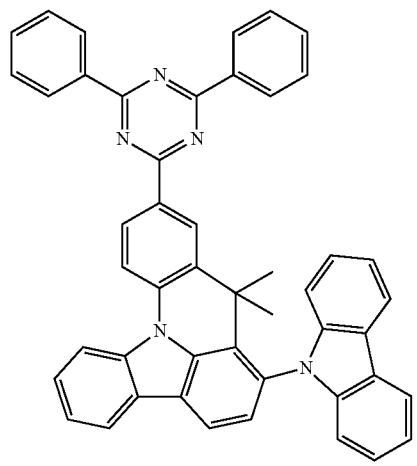
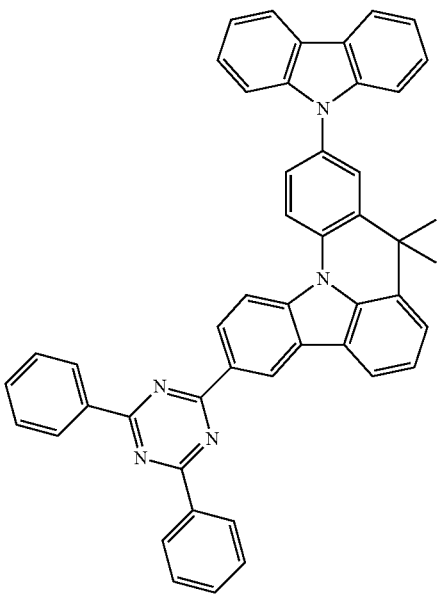

61
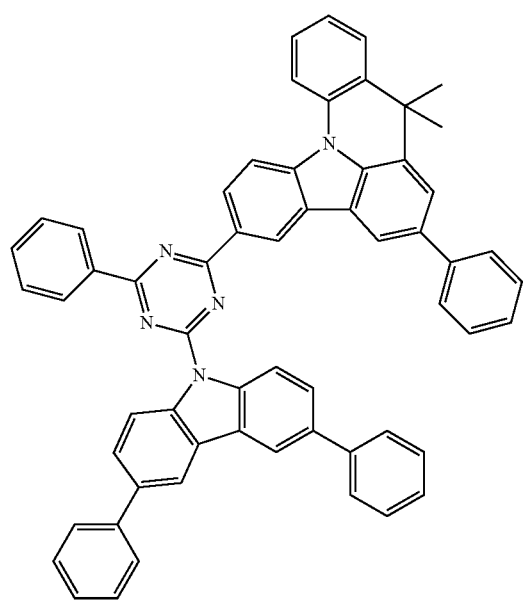
62
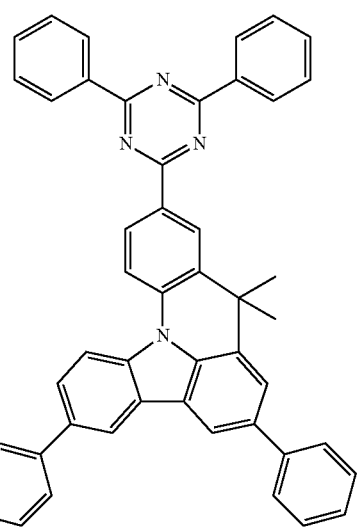
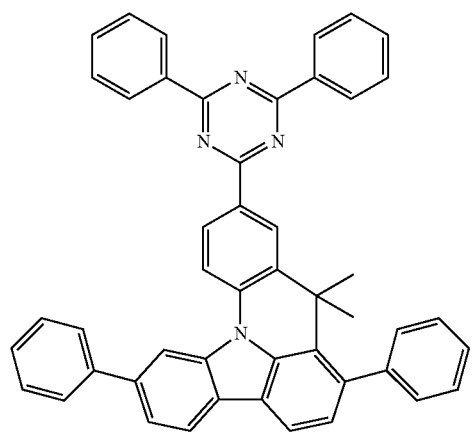
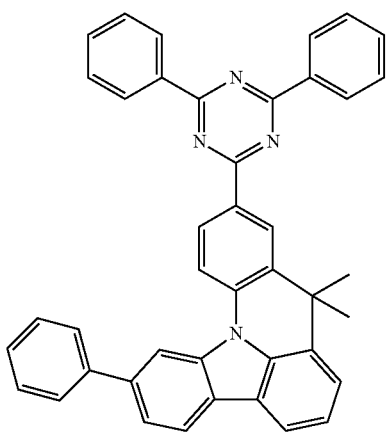
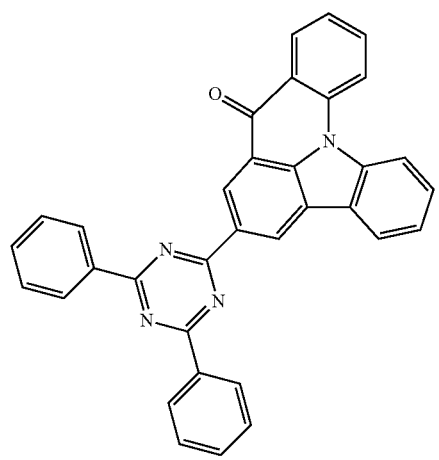
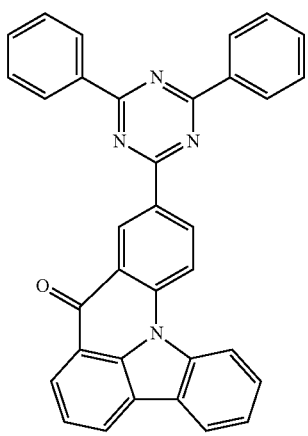

-continued
63
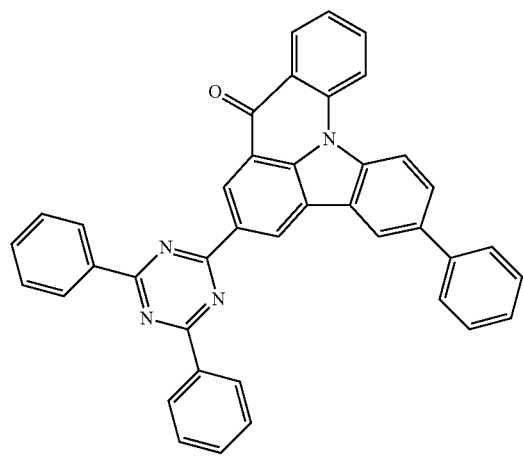
64
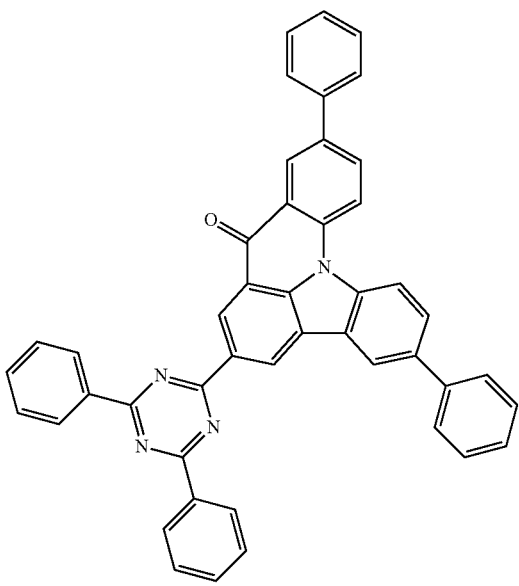
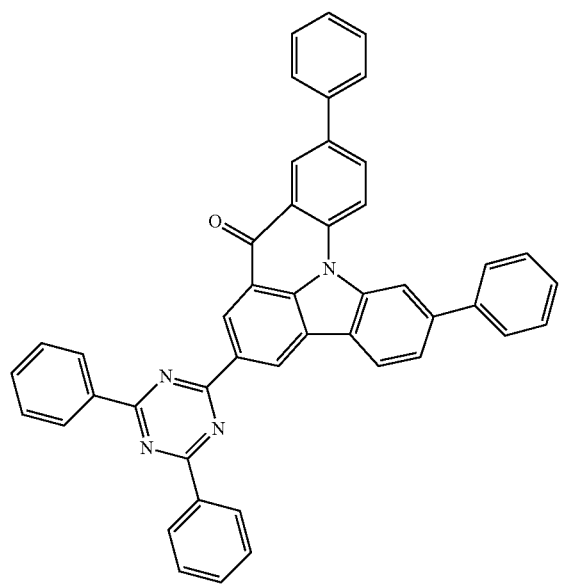
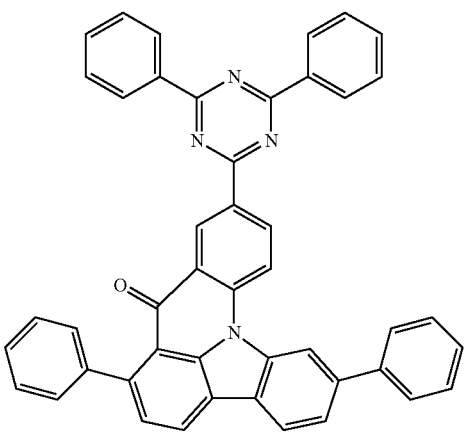
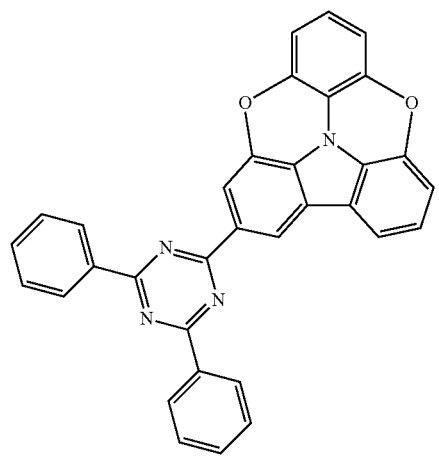
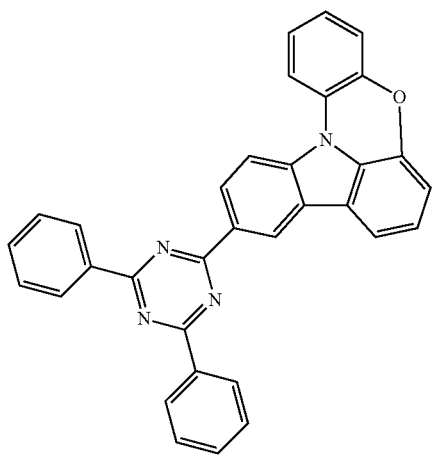

-continued
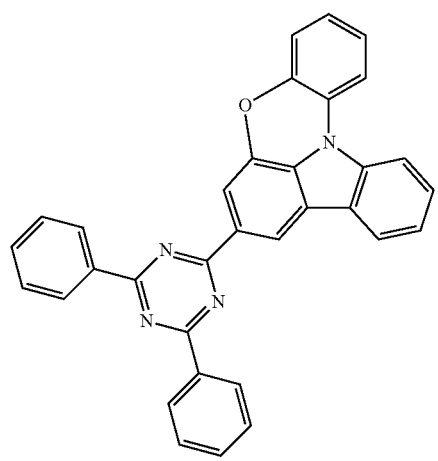
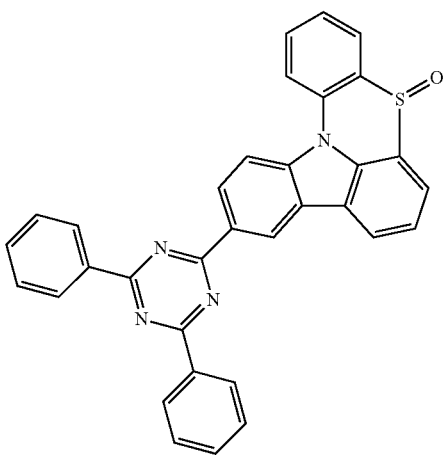
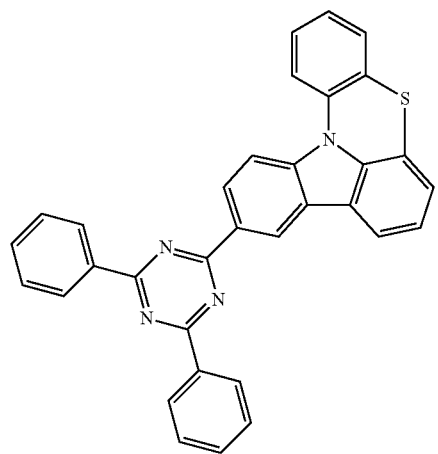
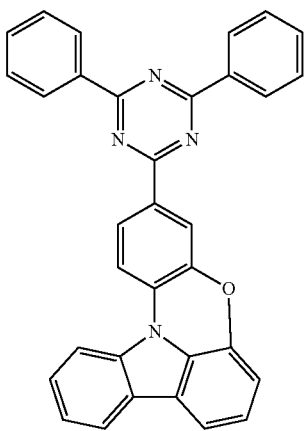
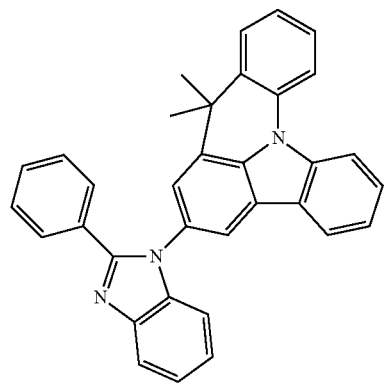
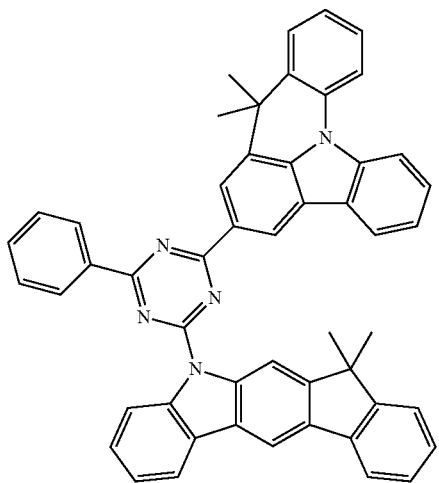

-continued
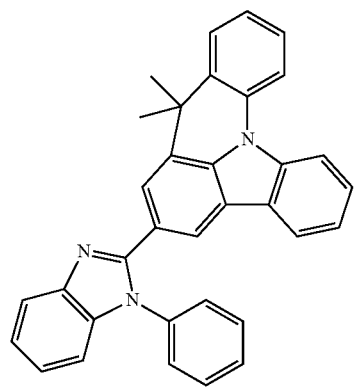
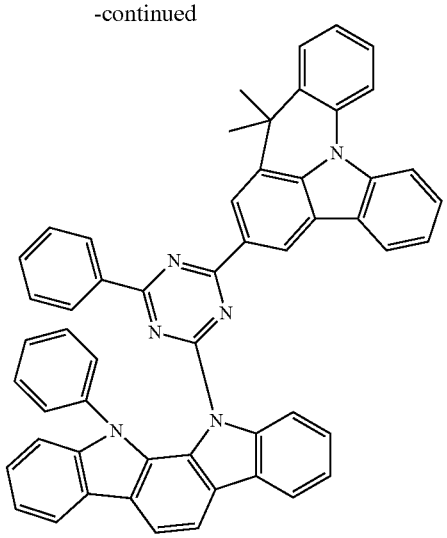
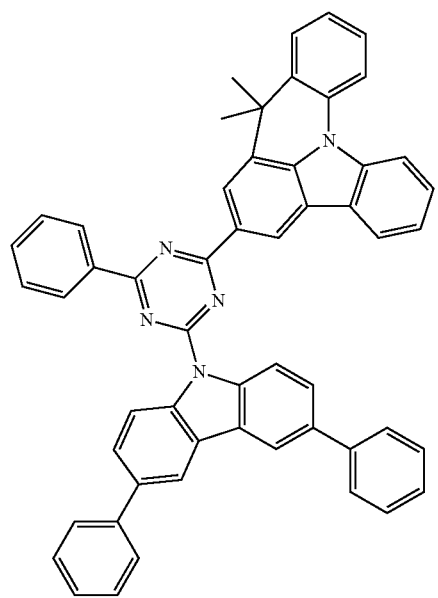
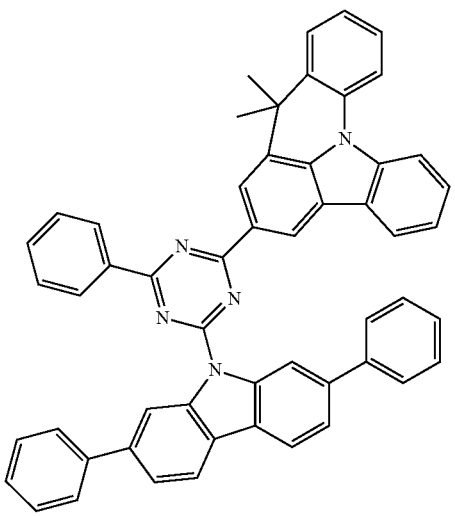
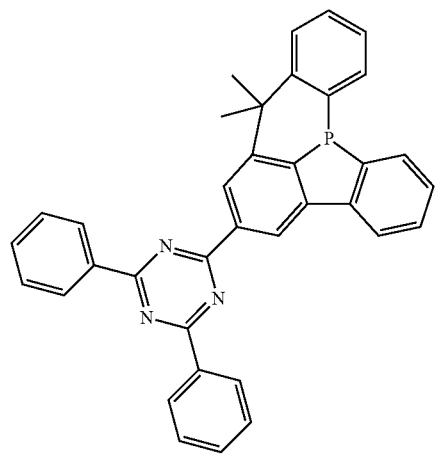
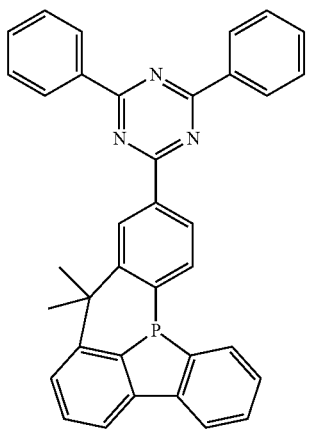
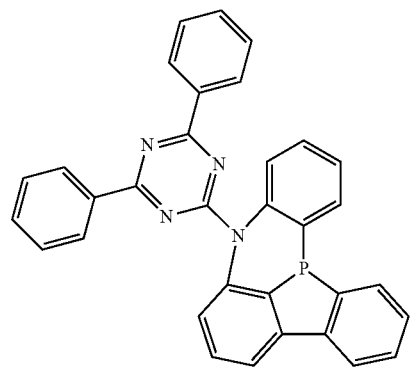

-continued
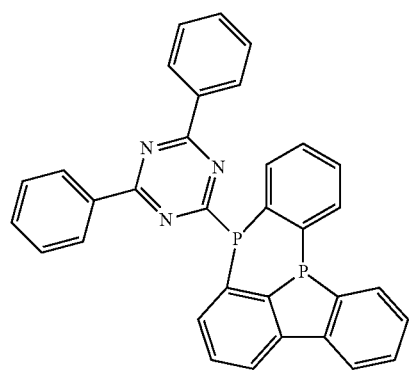
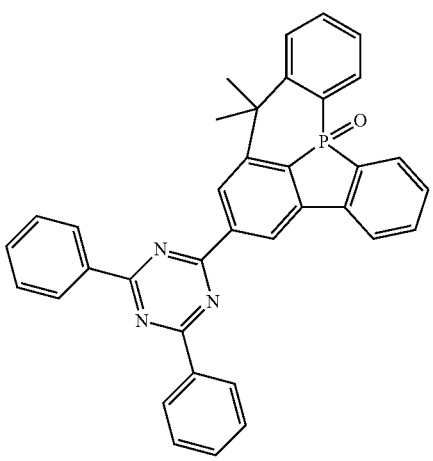
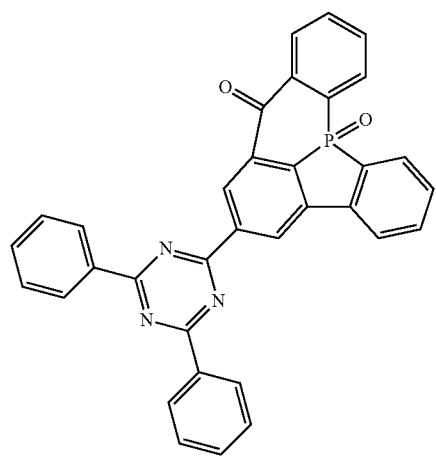
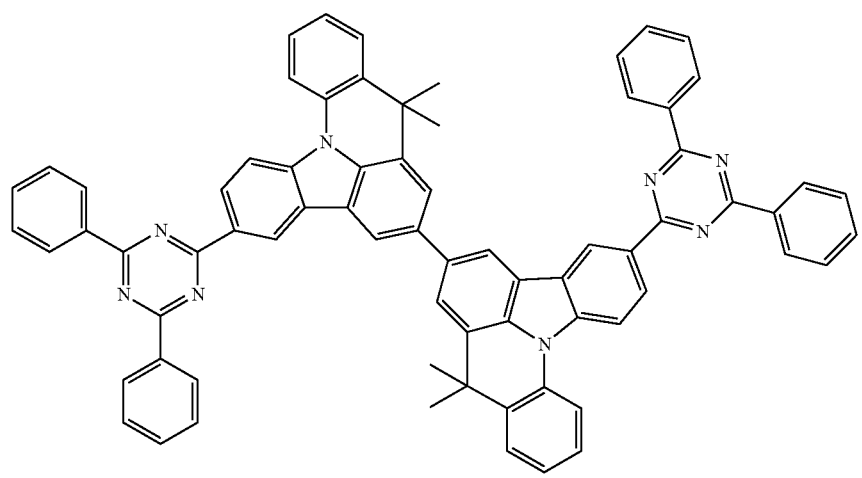

-continued
71
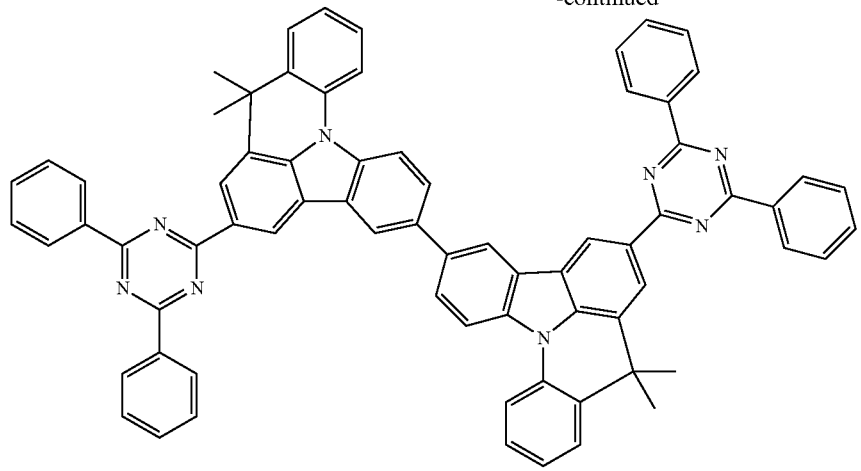
72
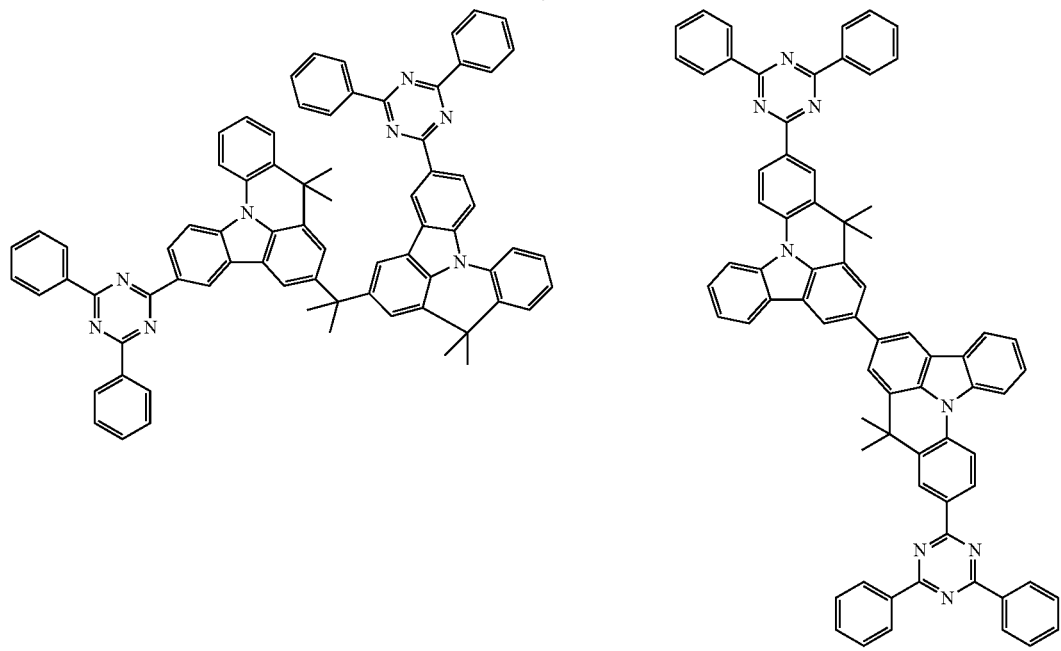
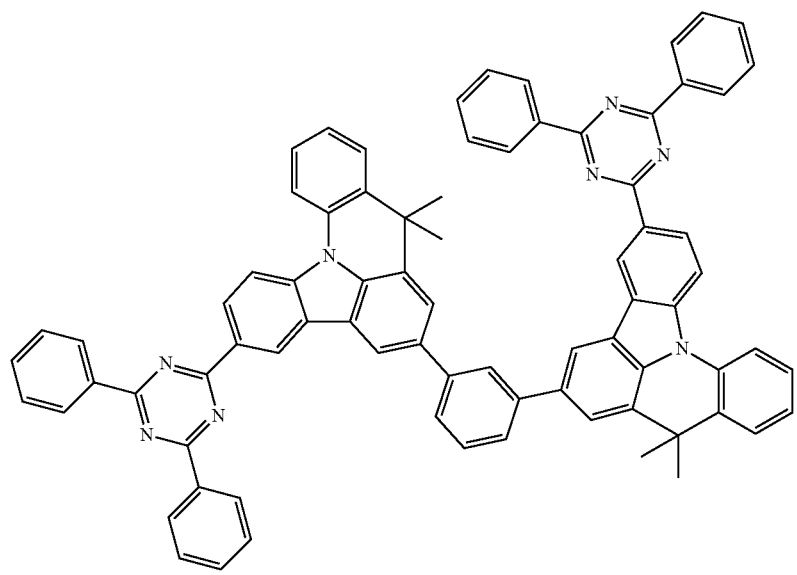

-continued
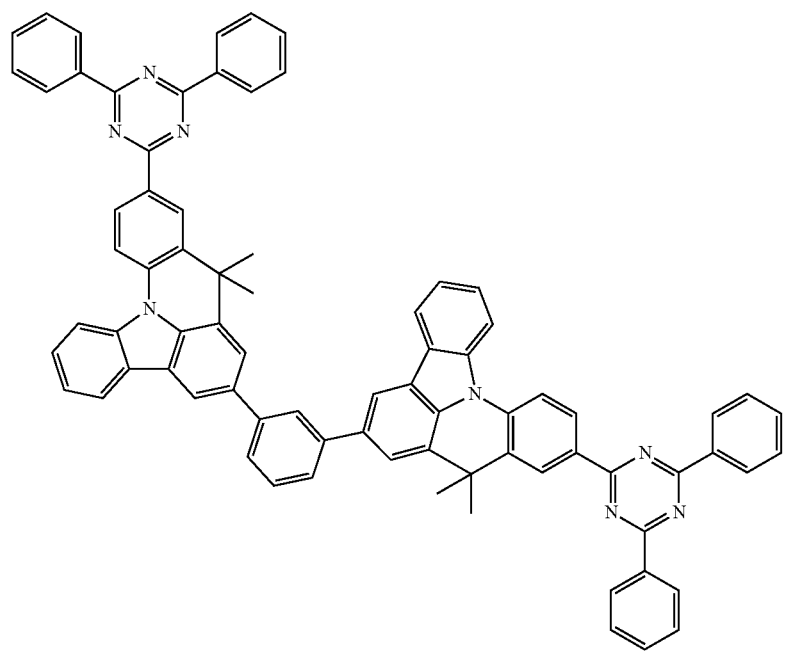
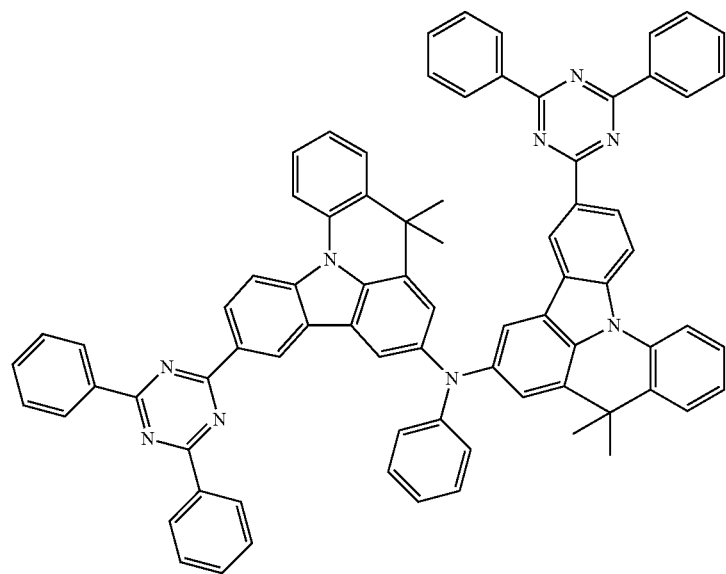

-continued
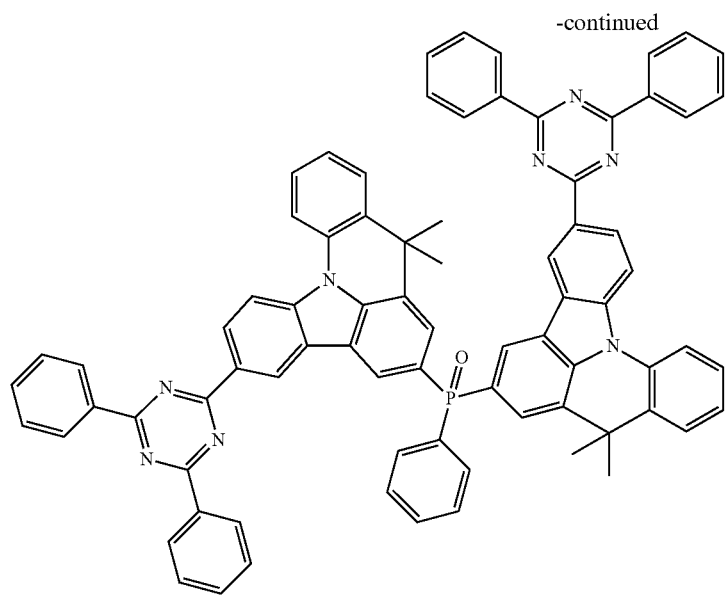
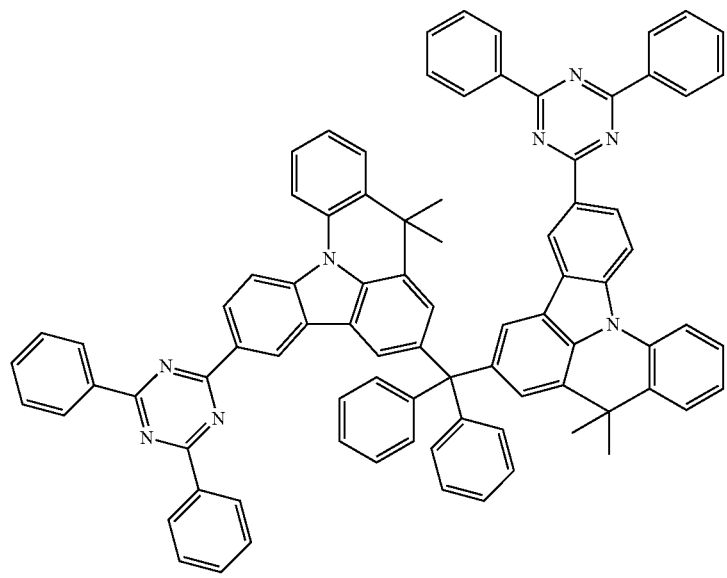
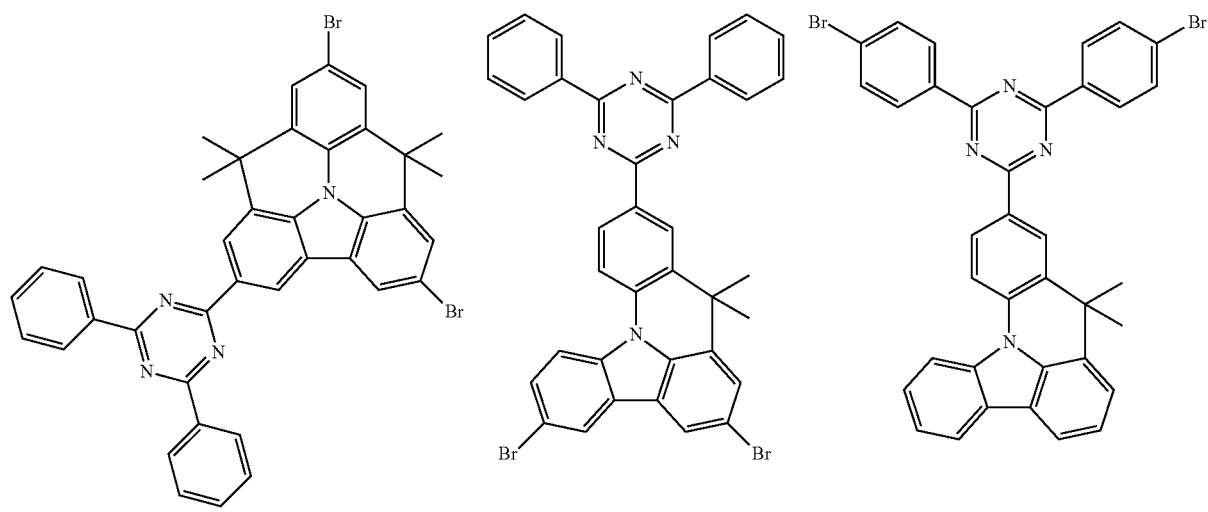

77
78
-continued
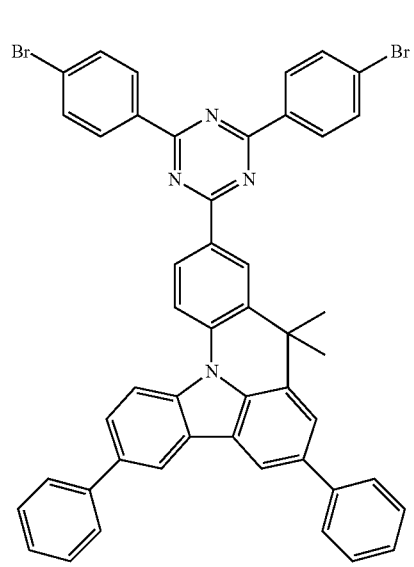
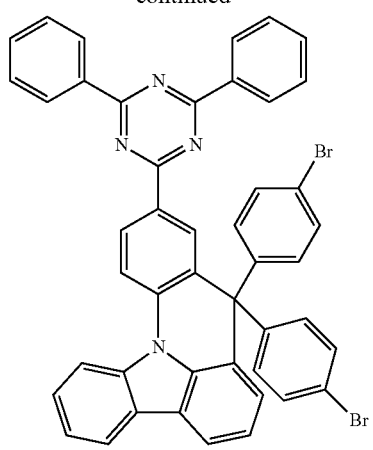
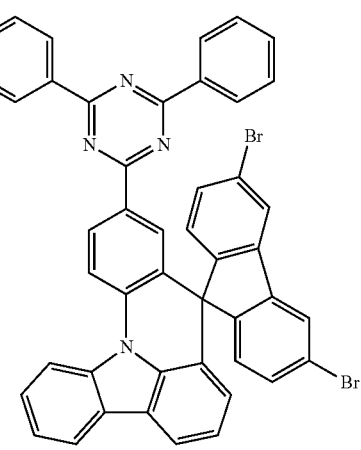
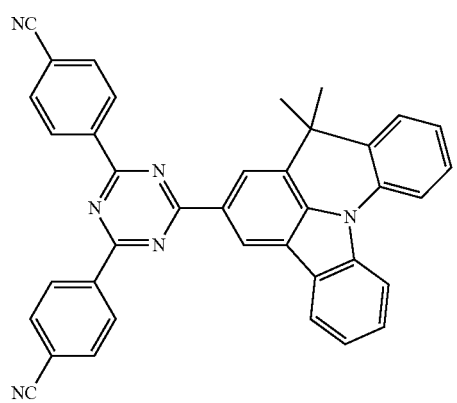
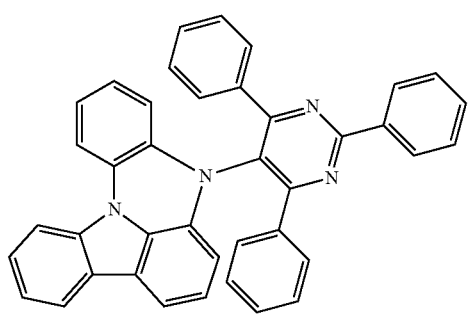
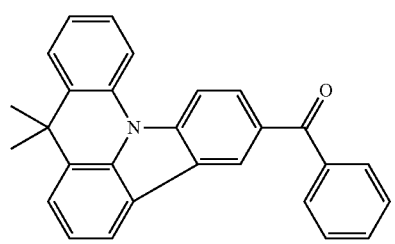
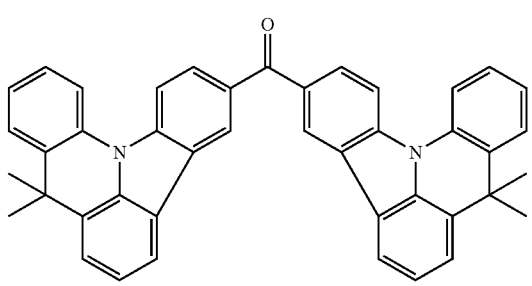
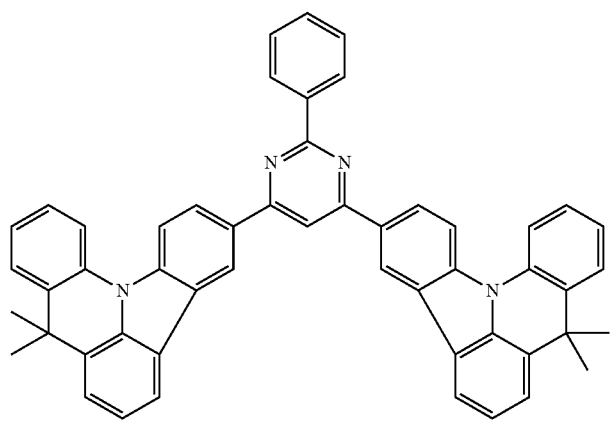

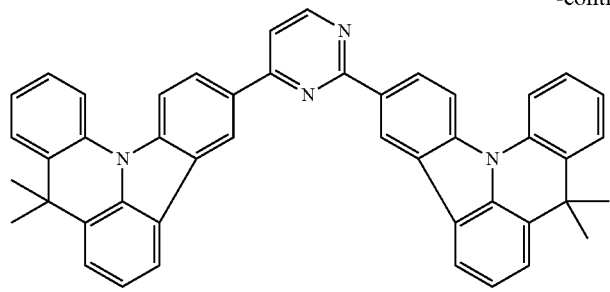
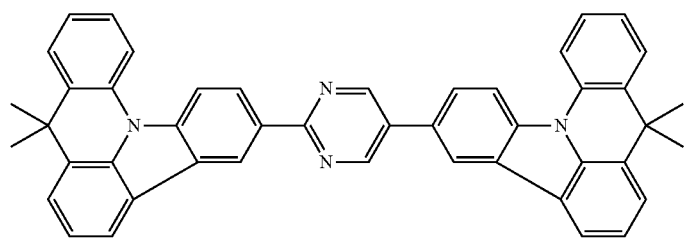
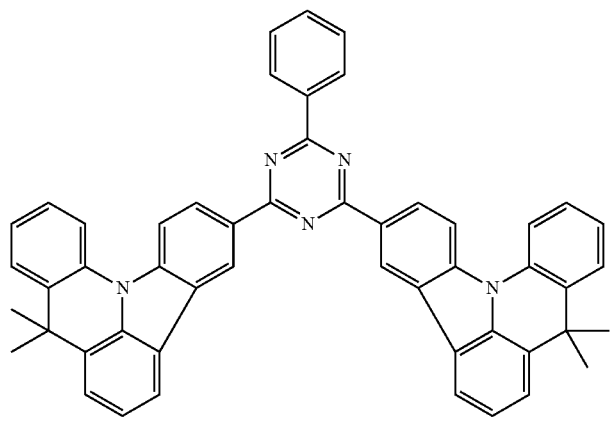
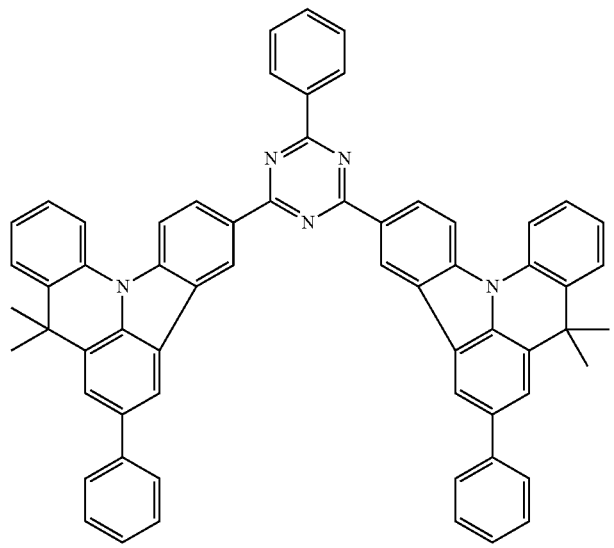

-continued
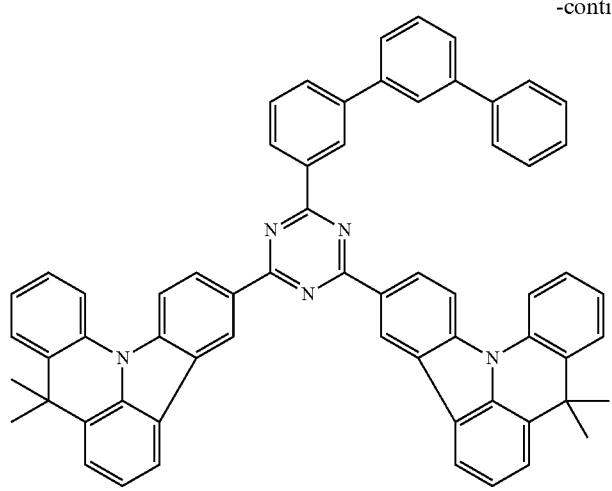
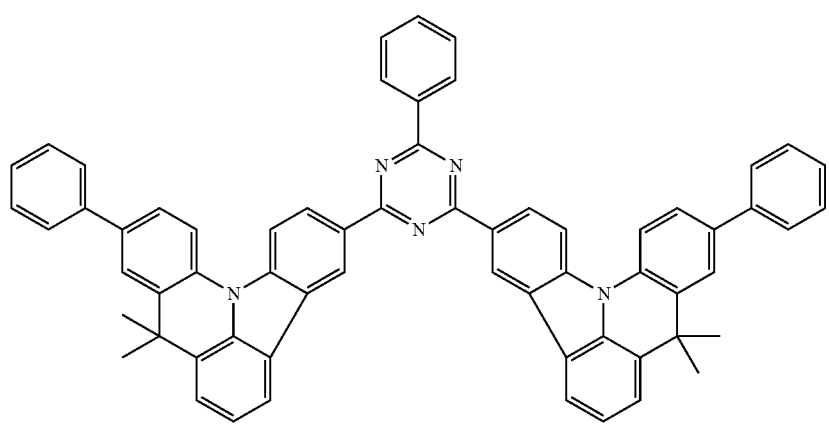
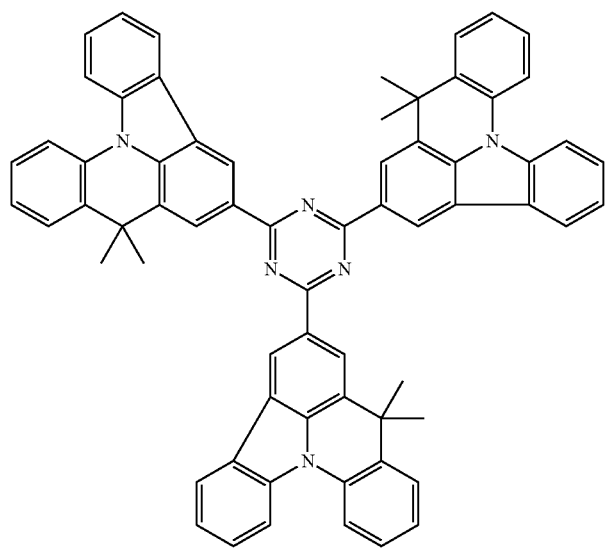

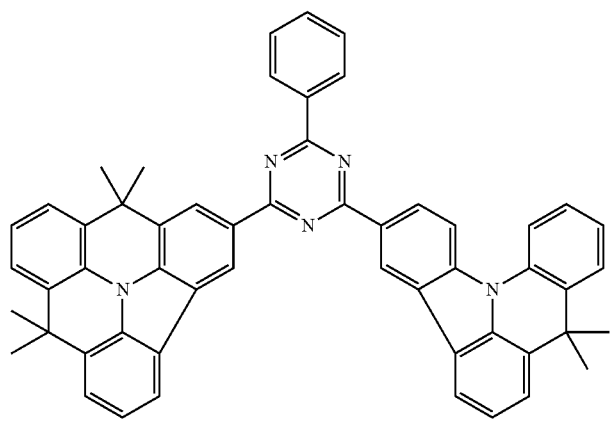
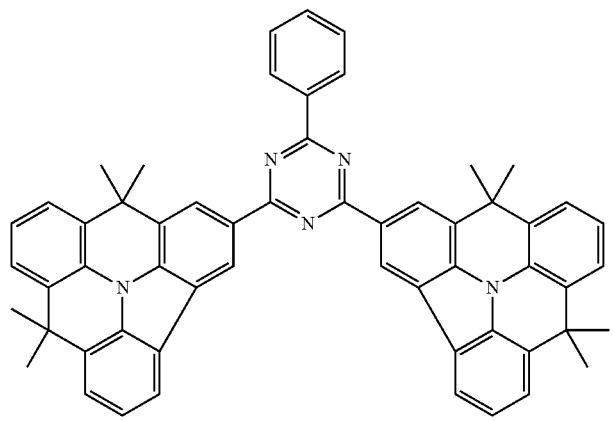
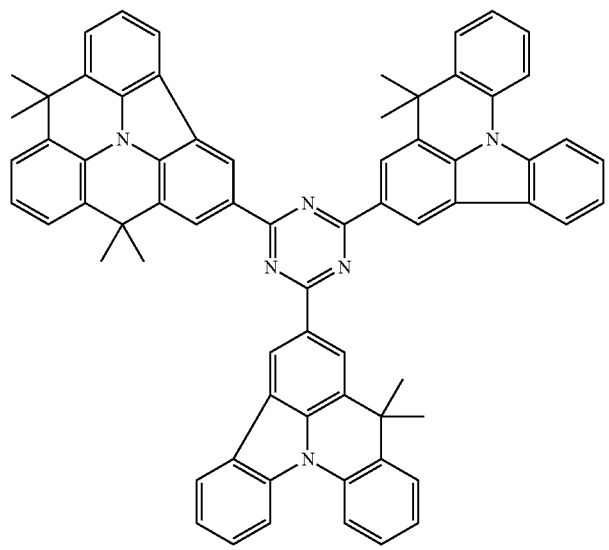

85
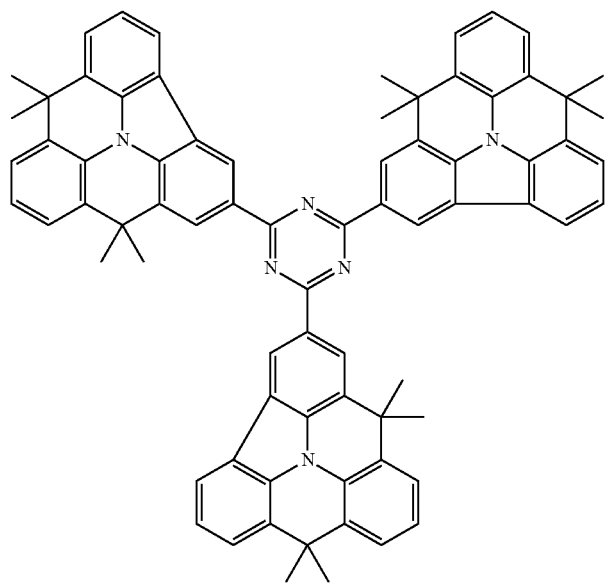
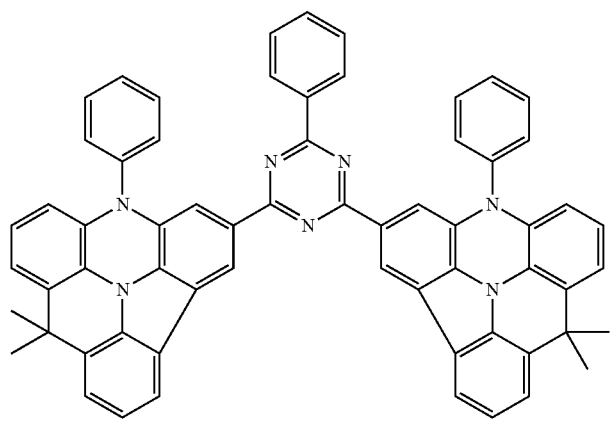
86
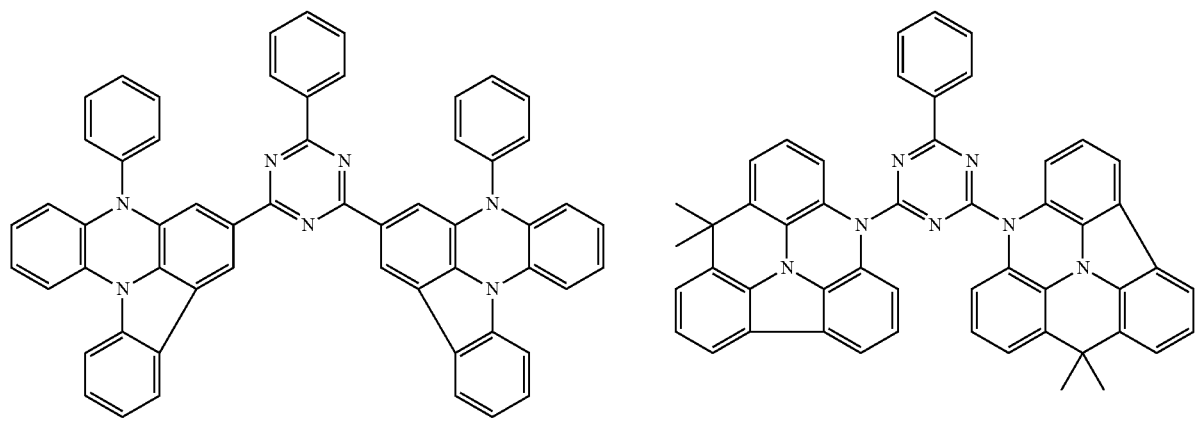

-continued
87
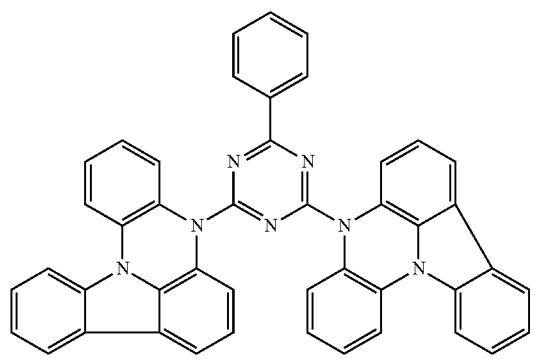
88
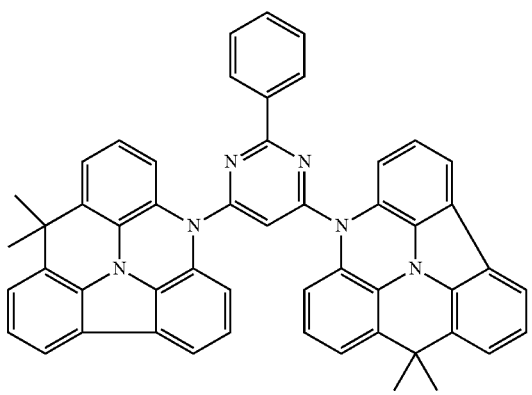
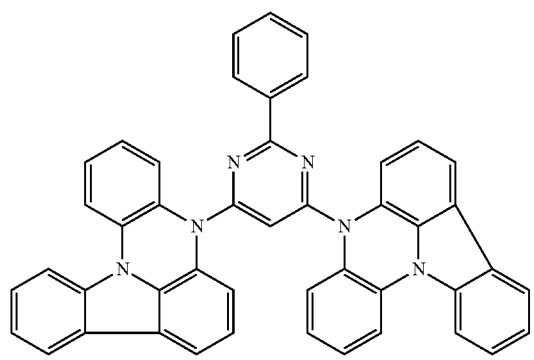
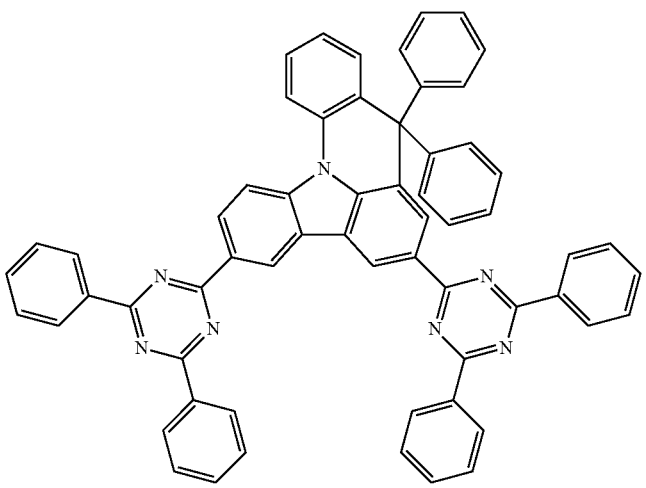
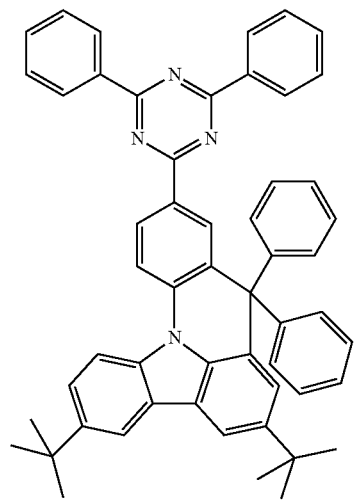
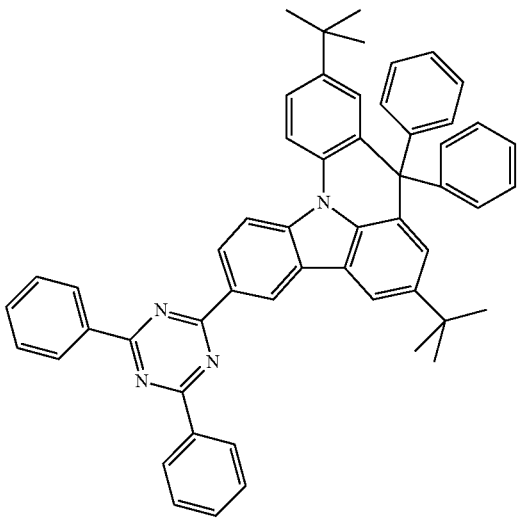

89
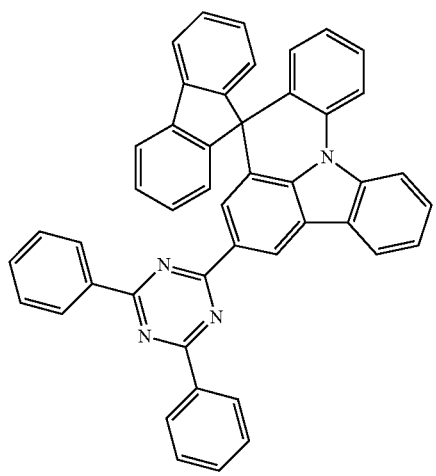
90
-continued
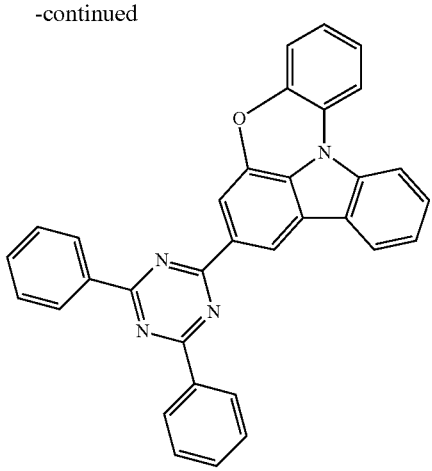
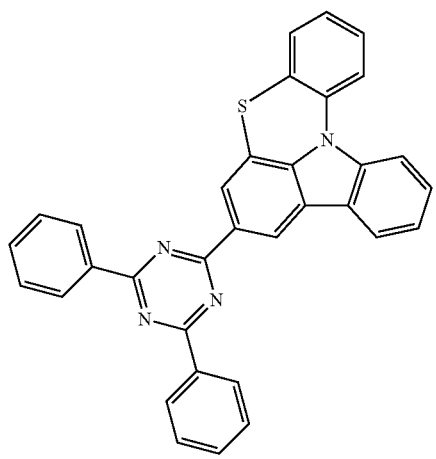
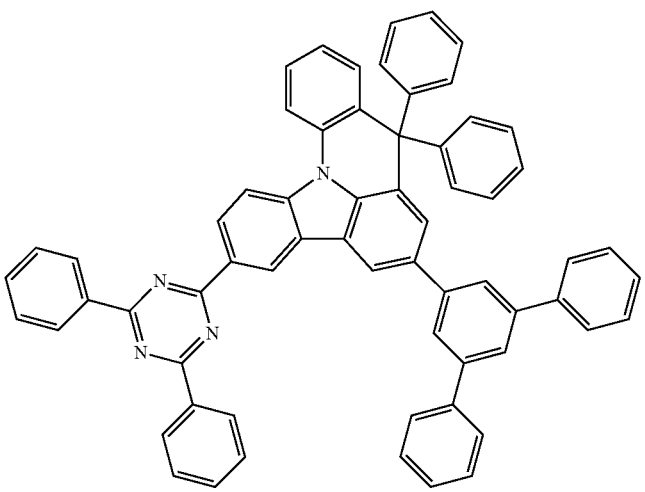
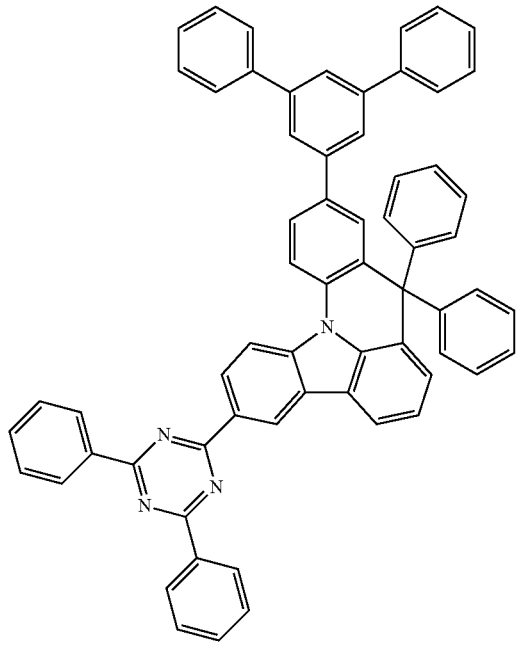
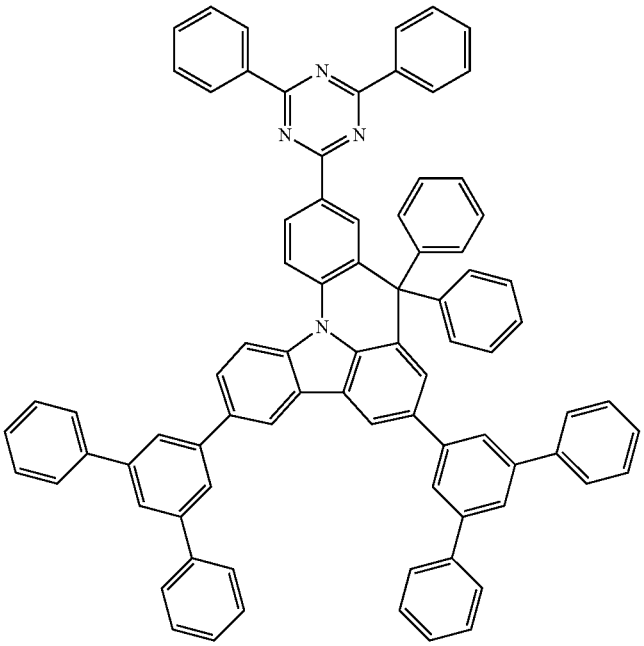

91
92
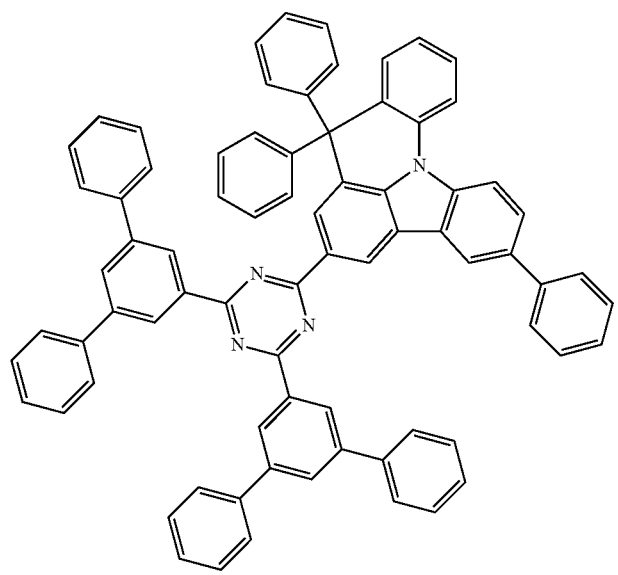
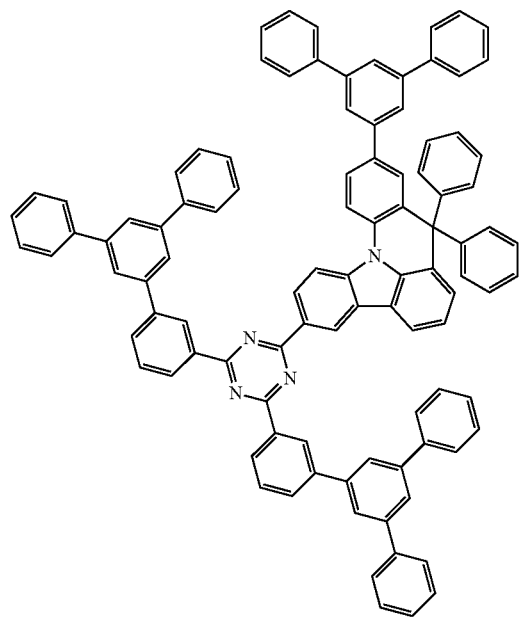
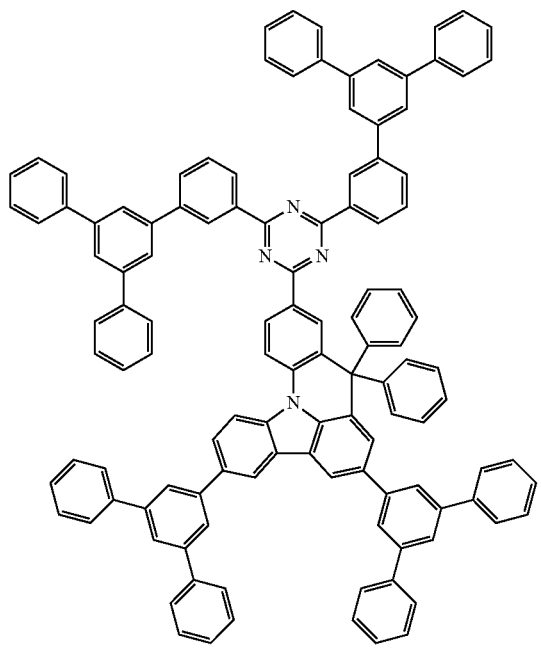

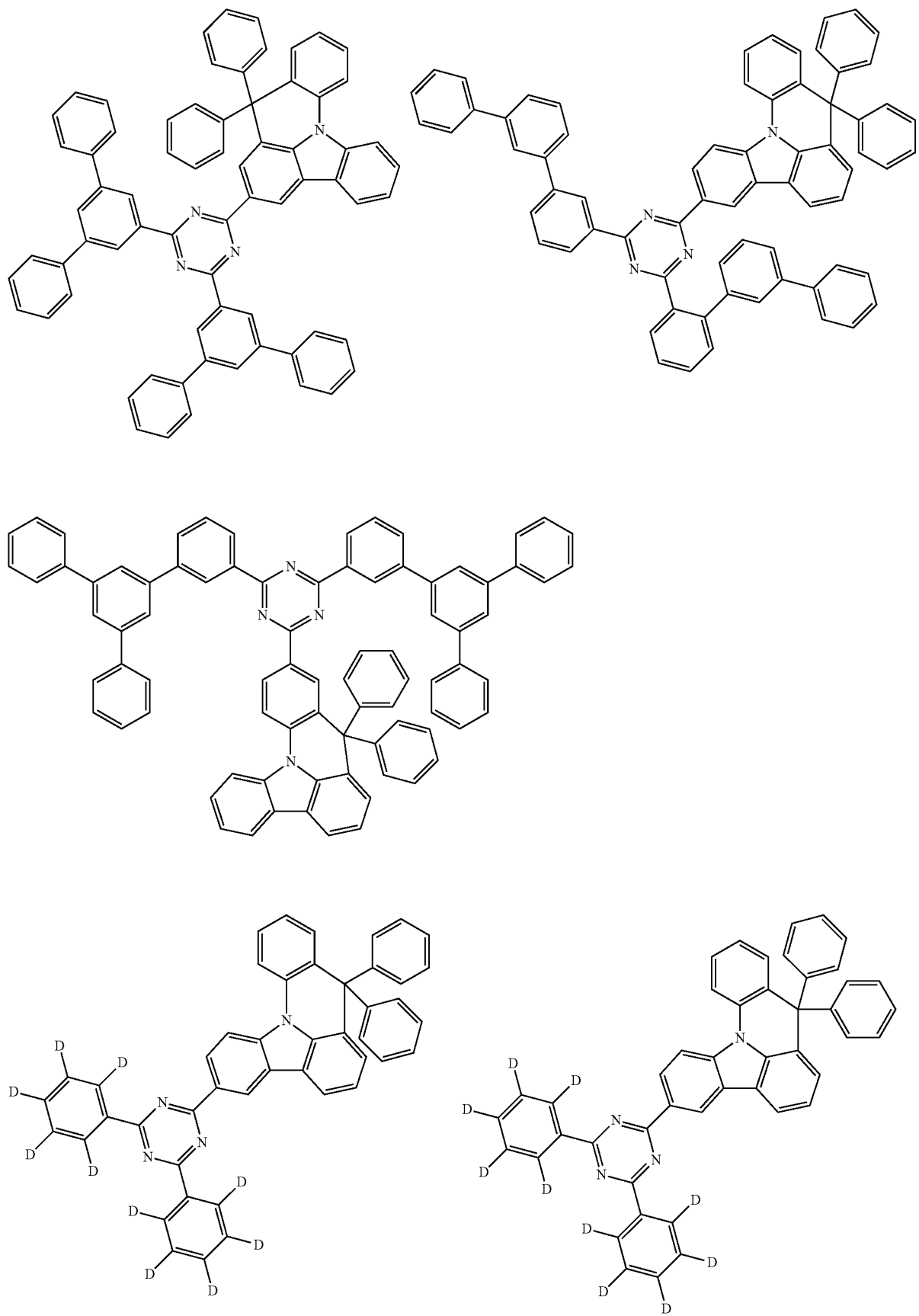

95
-continued
96
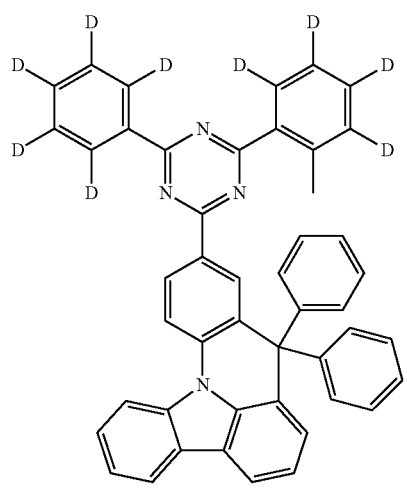
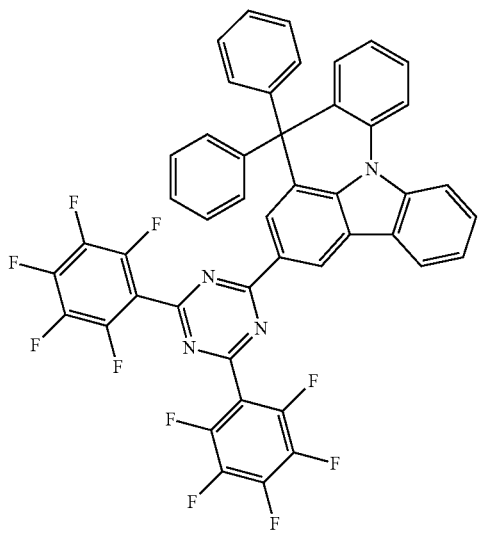
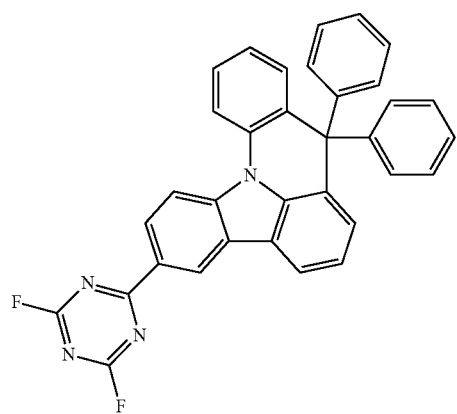
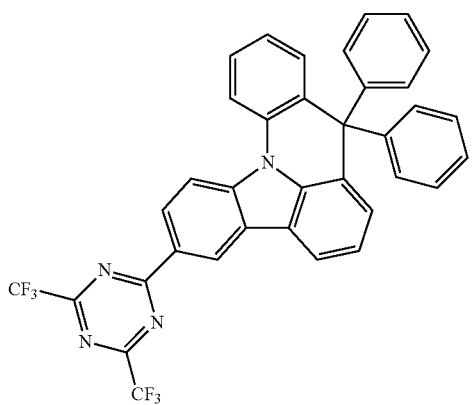
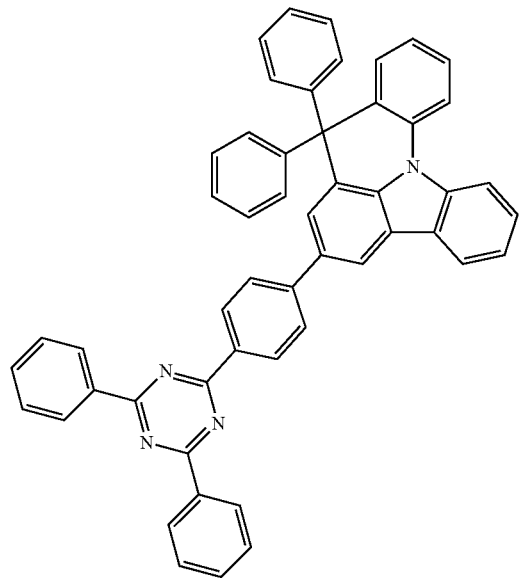
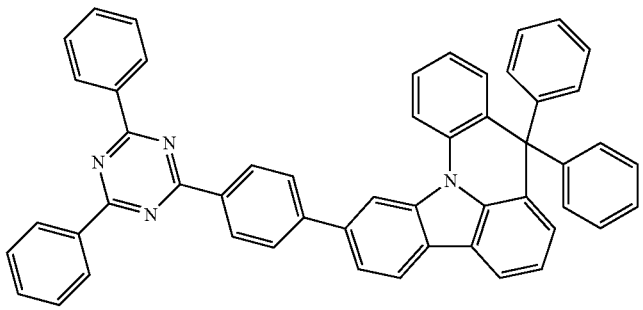

-continued
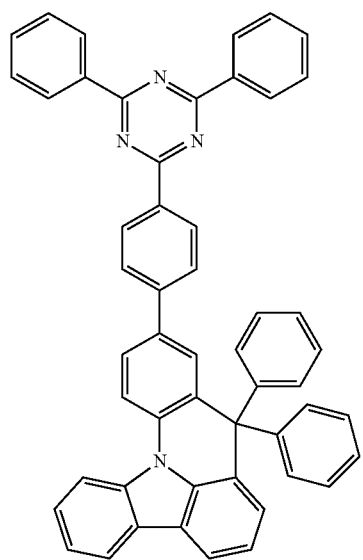
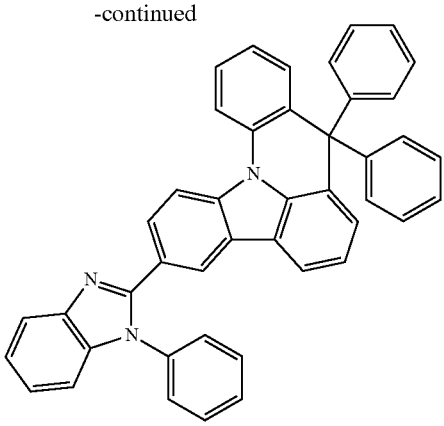
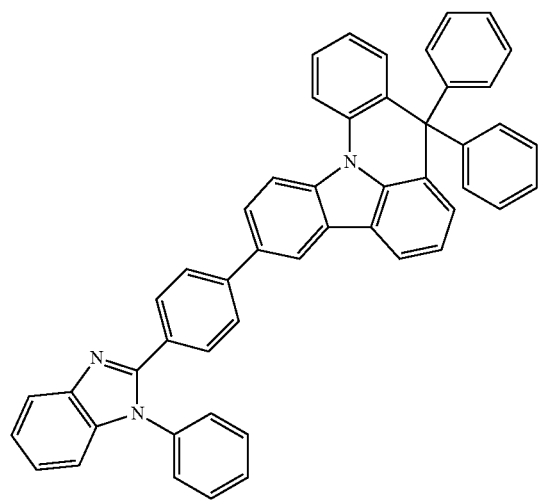
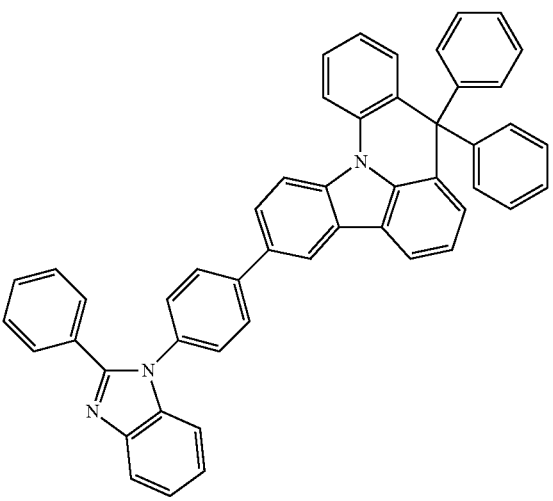
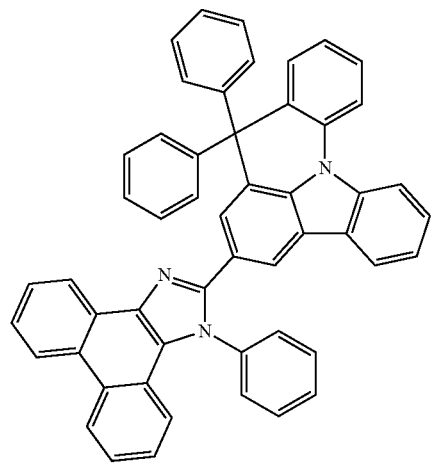
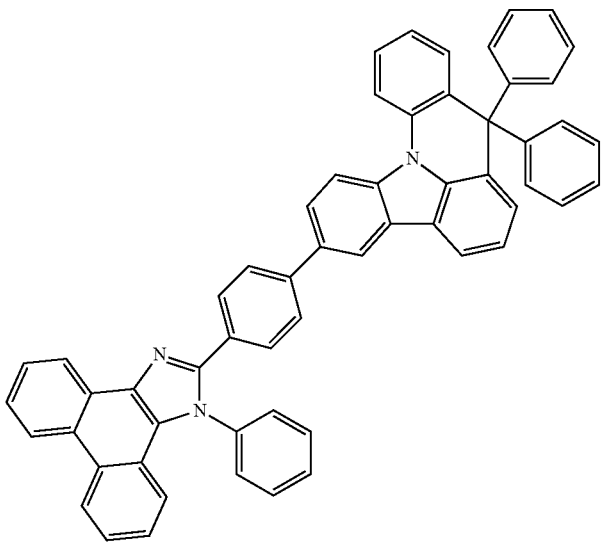

-continued
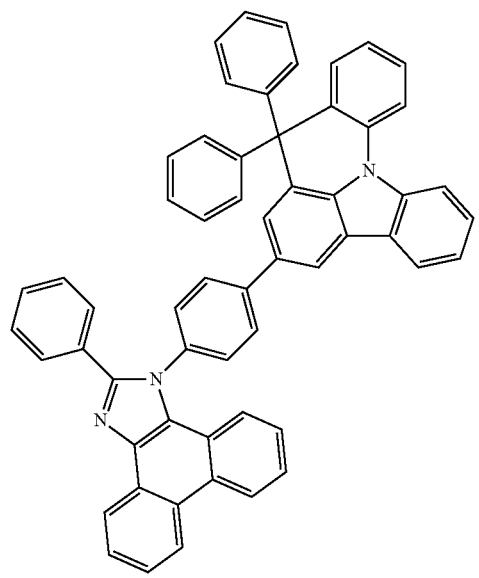
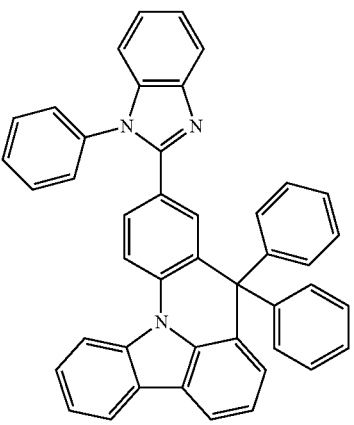
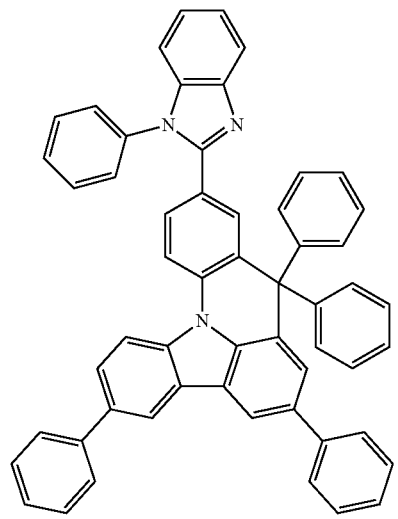
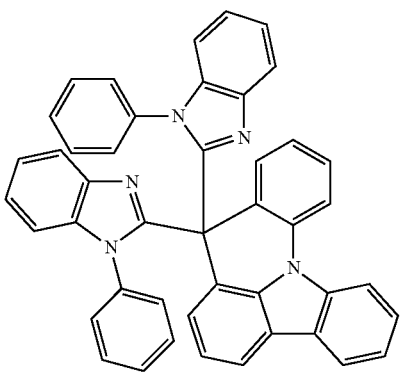
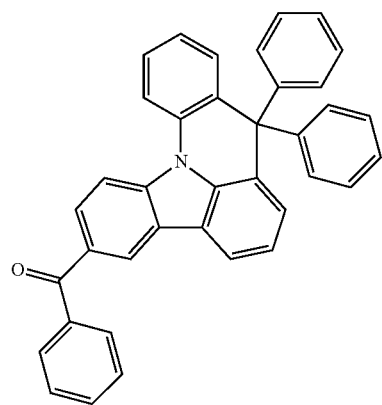
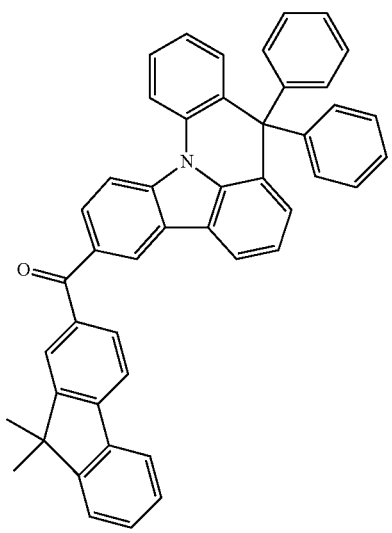
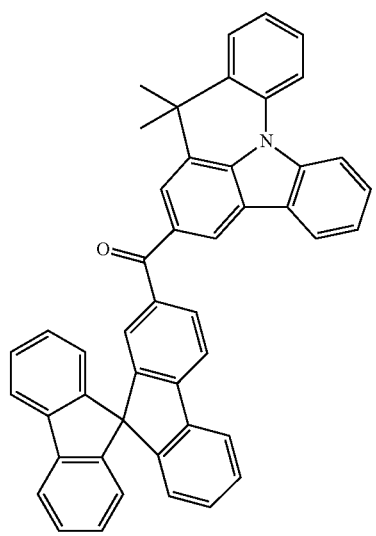

101
-continued
102
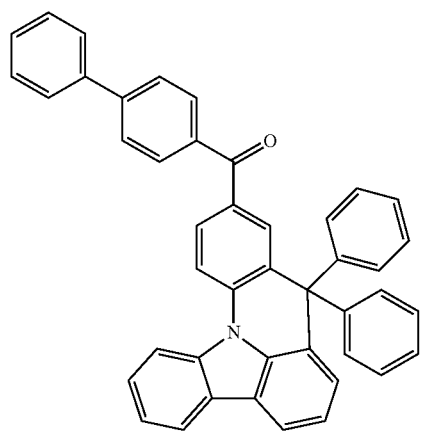
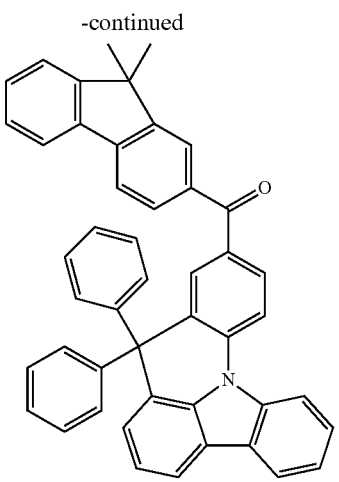
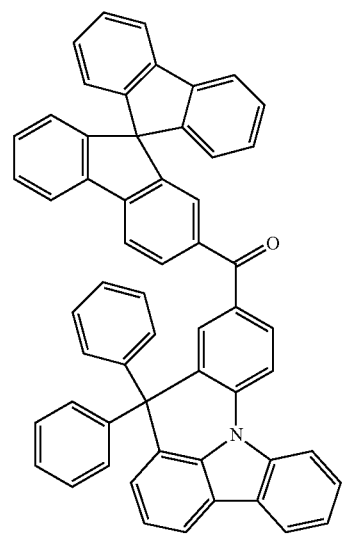
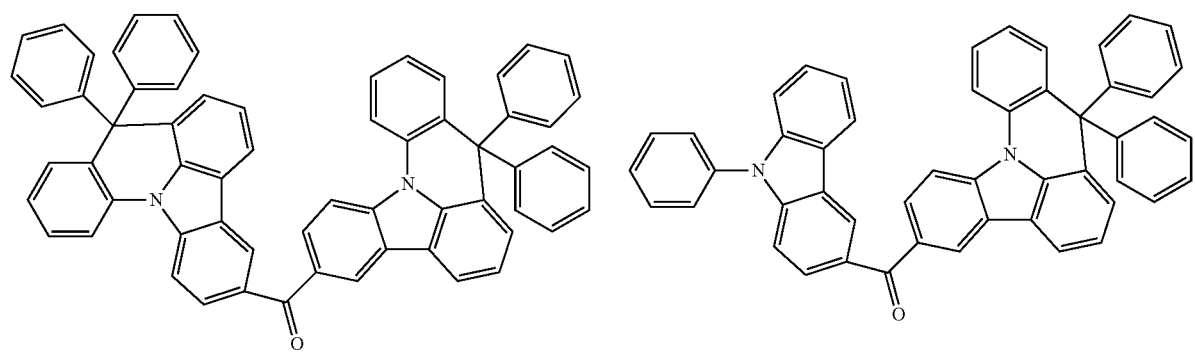
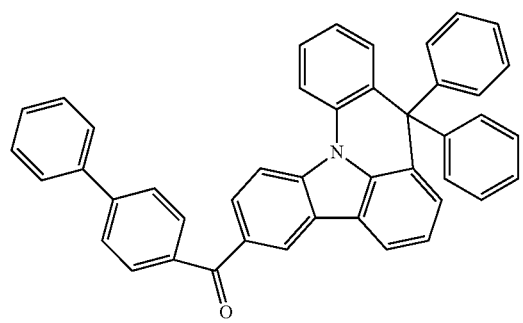
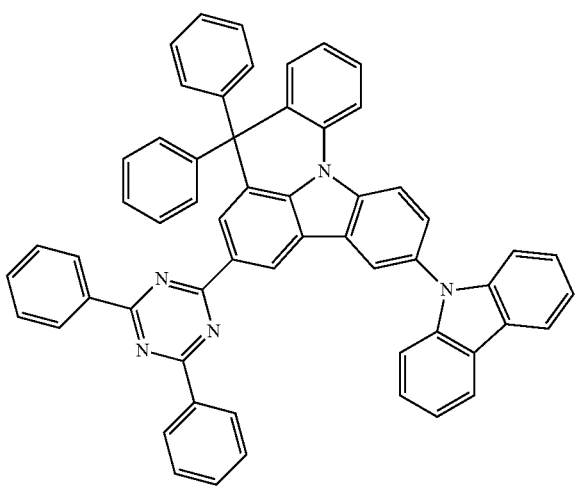

103
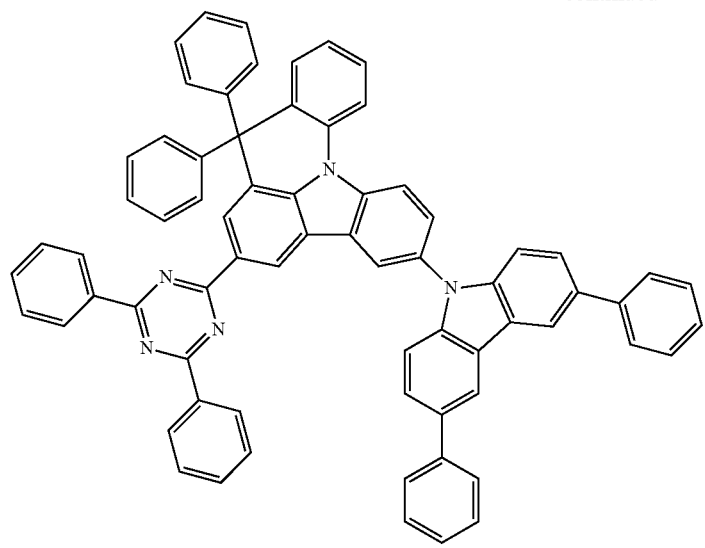
104
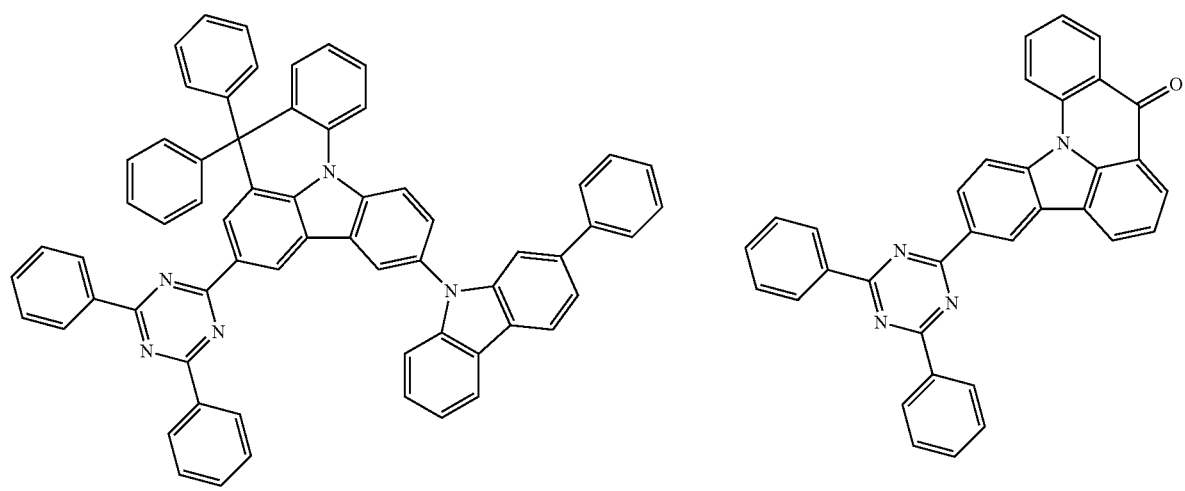
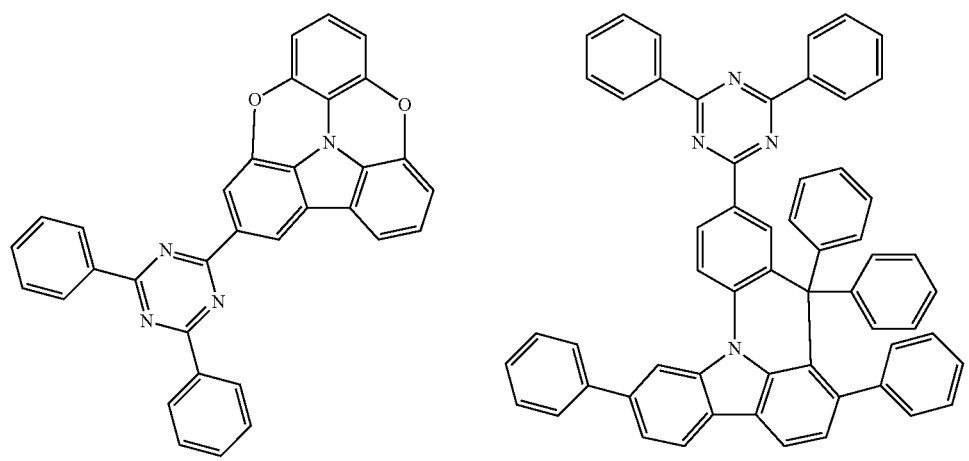

105
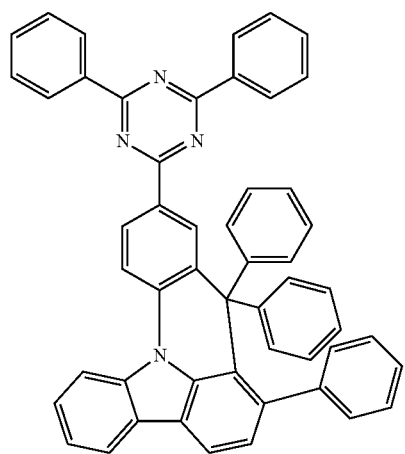
106
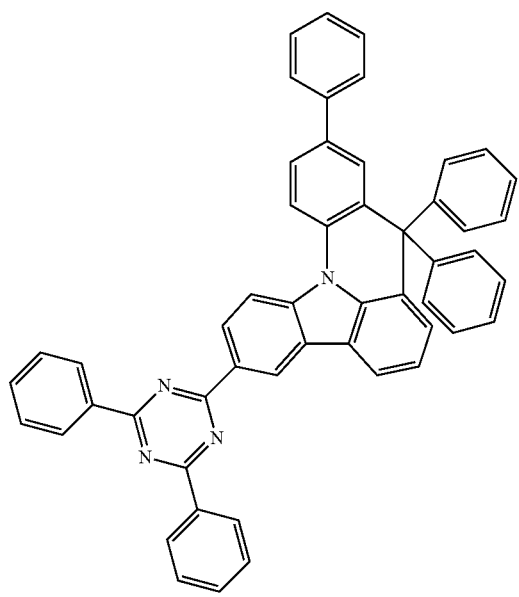
-continued
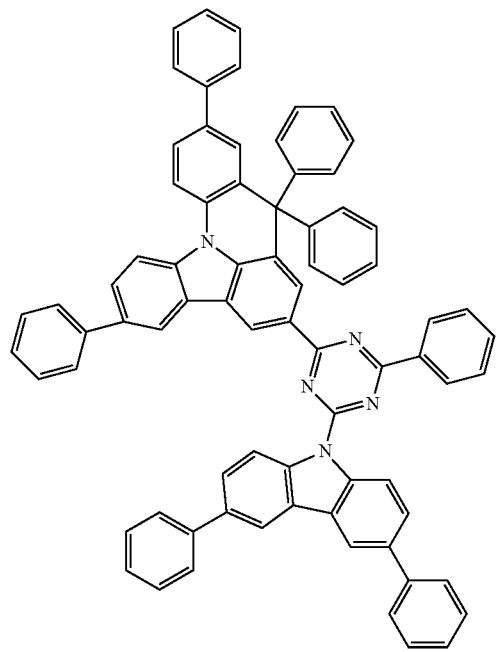
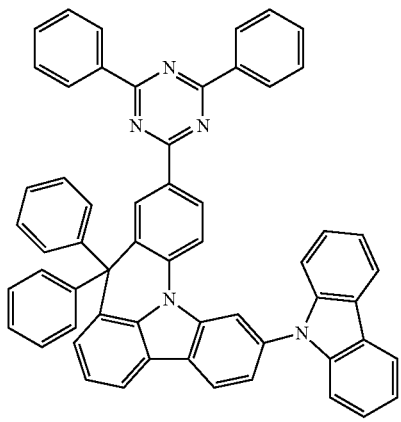

-continued
107
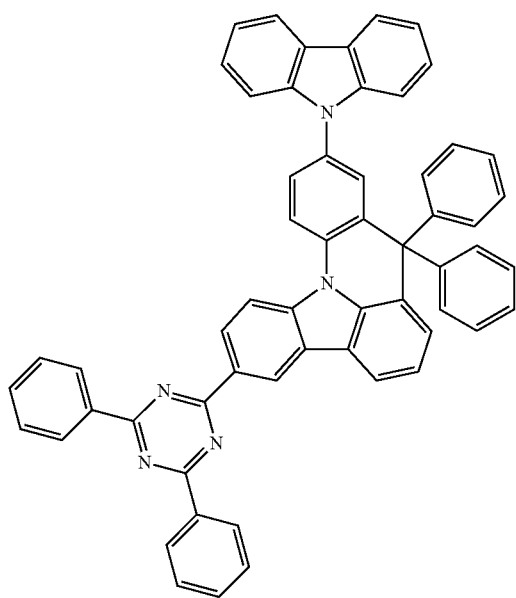
108
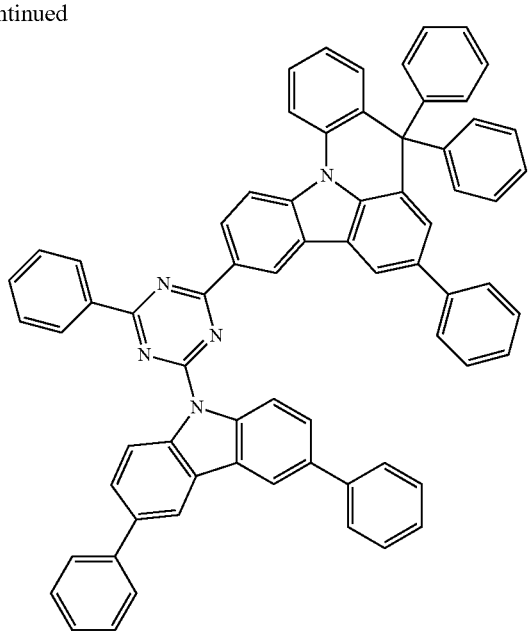
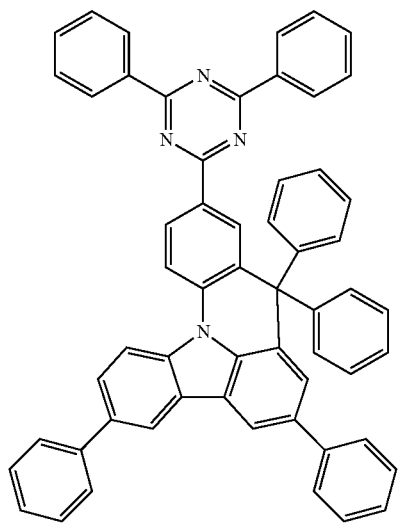
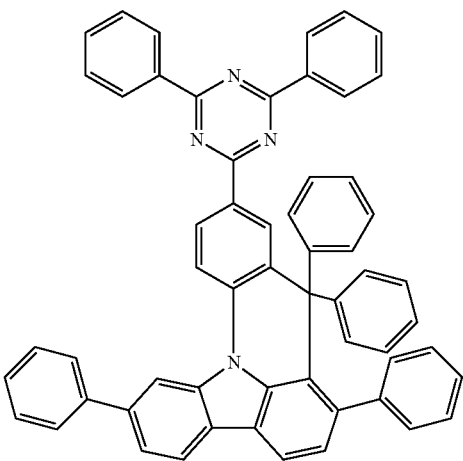
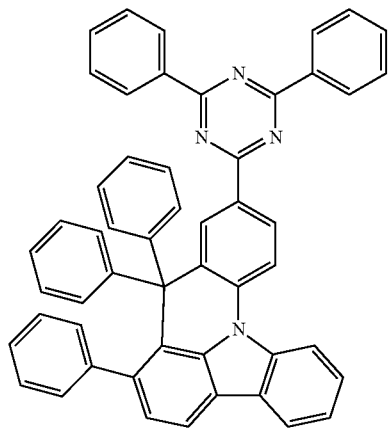
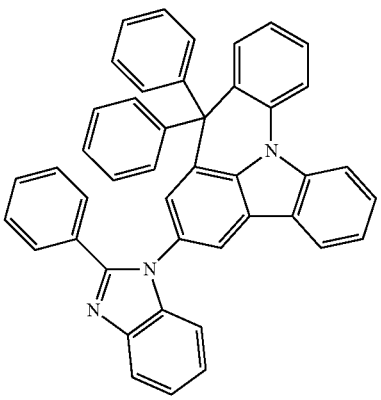

-continued
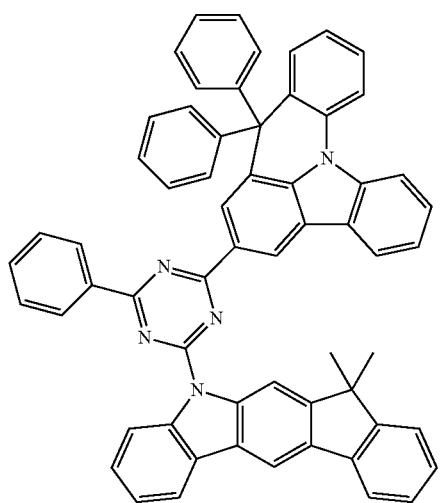
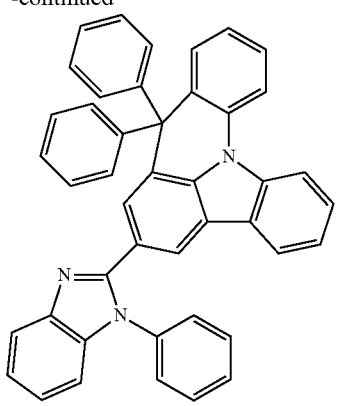
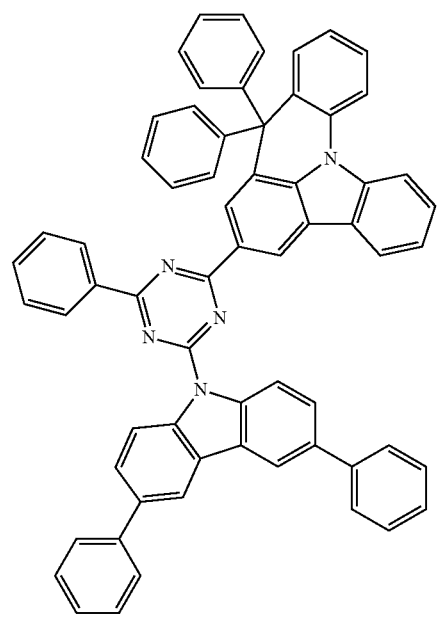
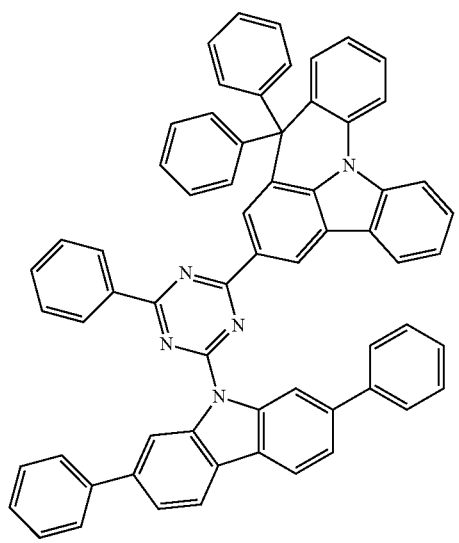
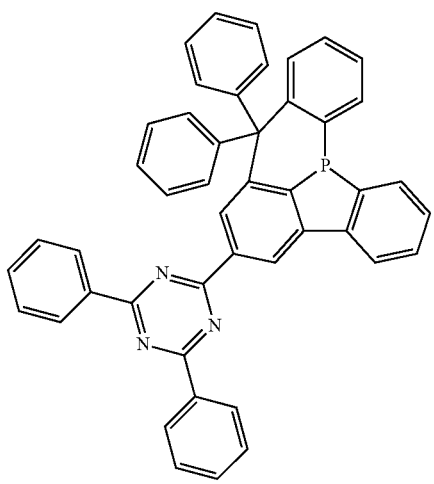

111
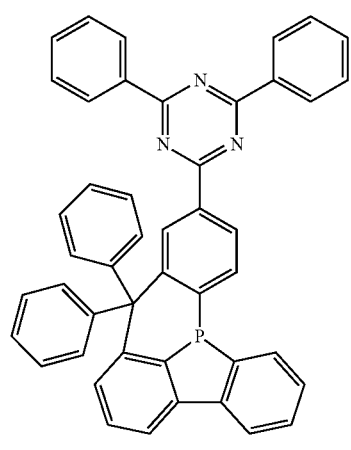
112
-continued
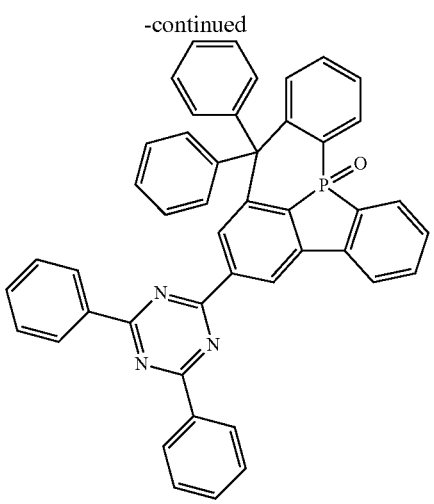
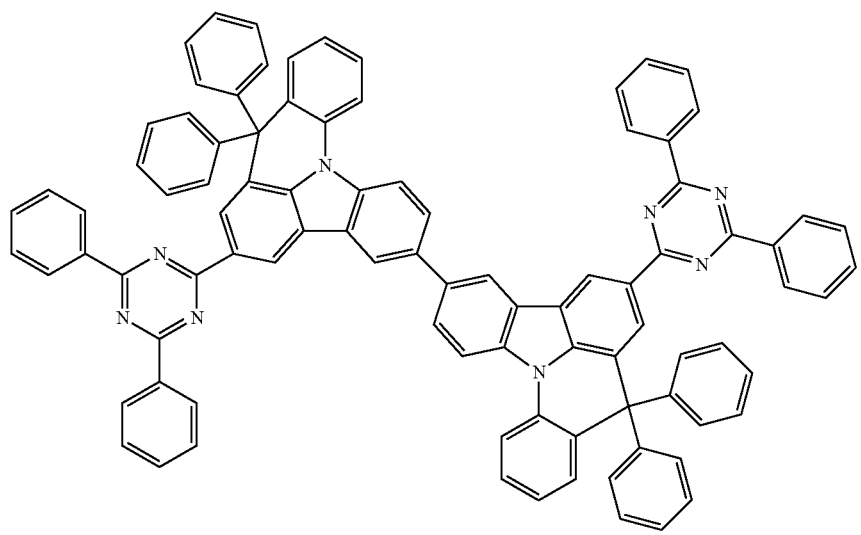
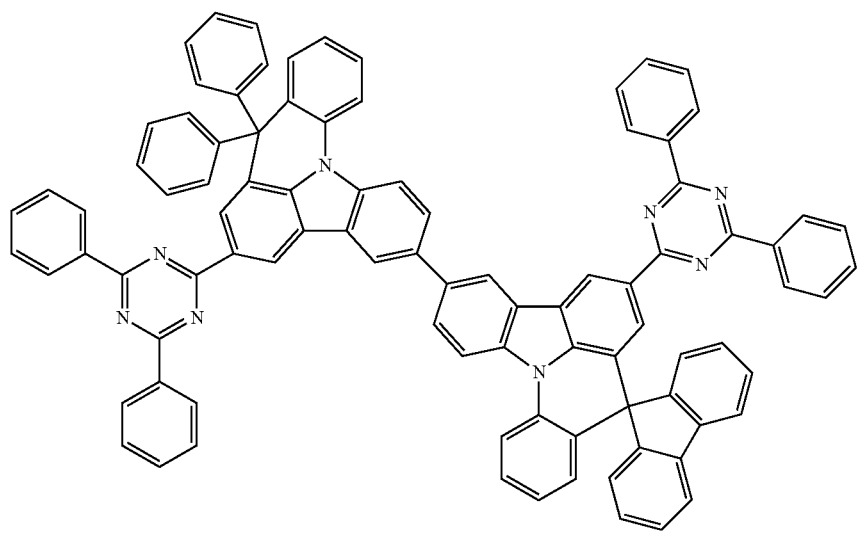

113
114
-continued
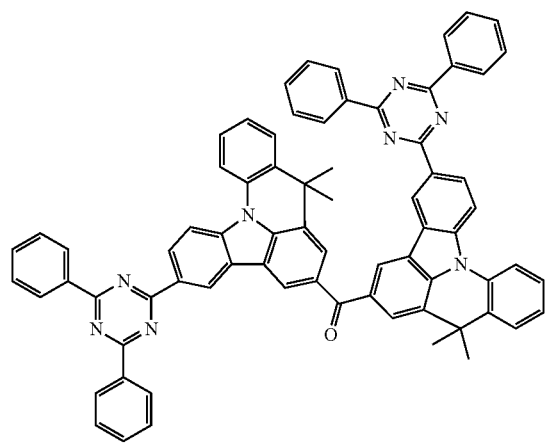
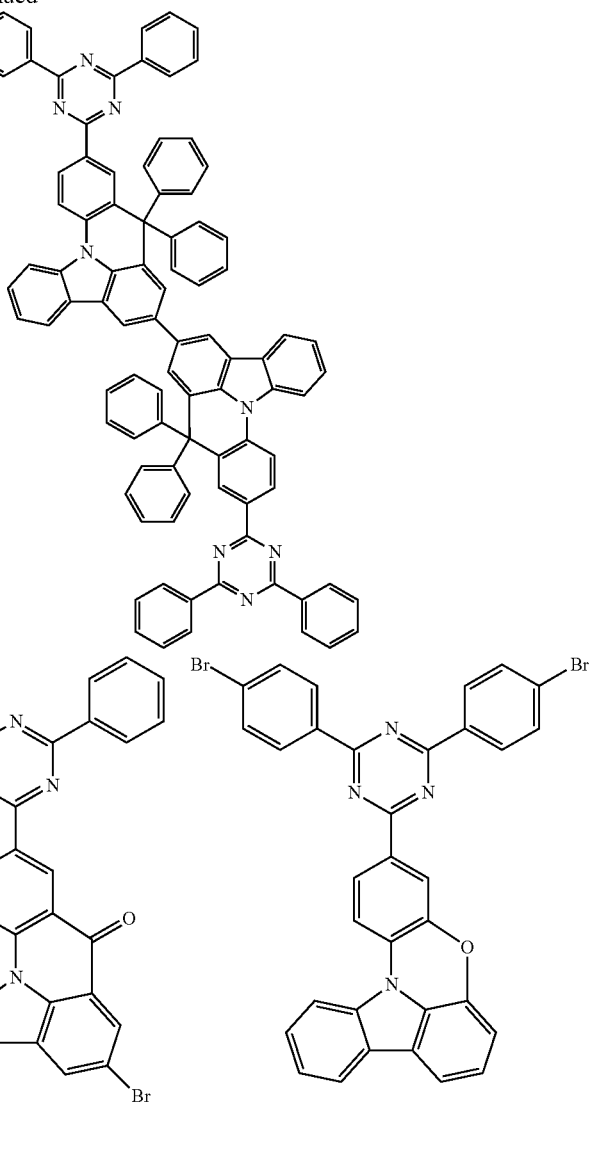
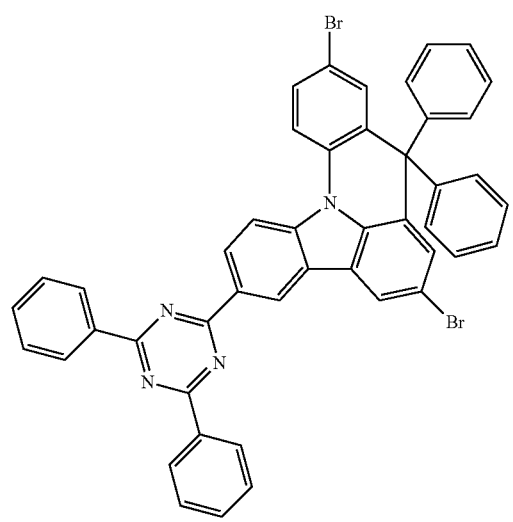
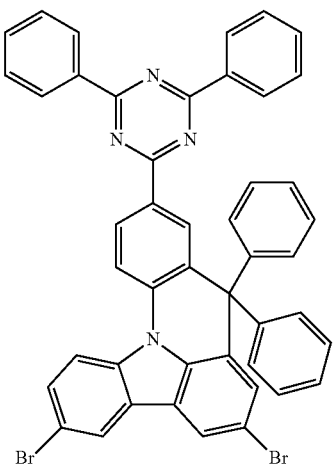

115
116
-continued
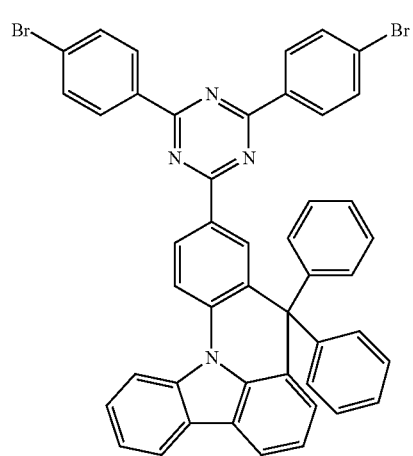
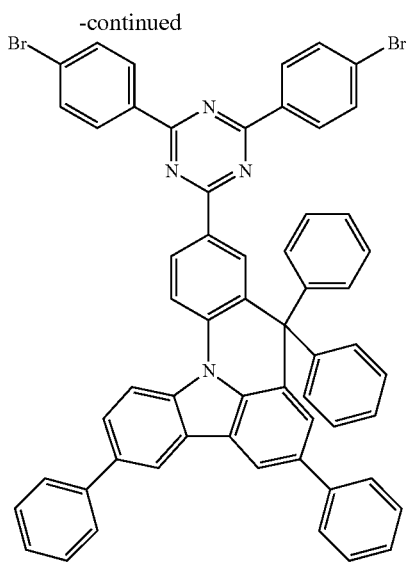
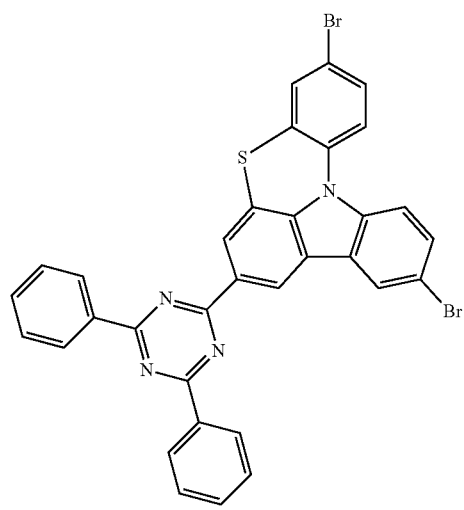
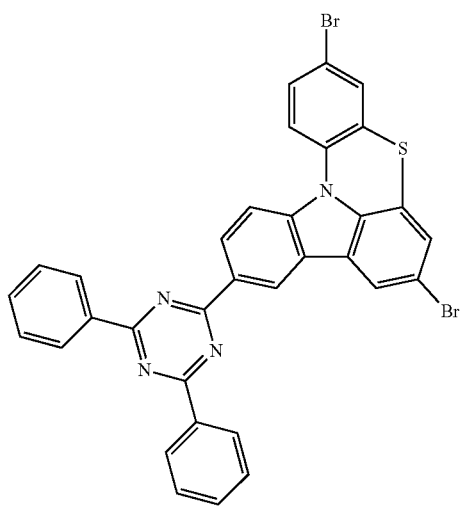
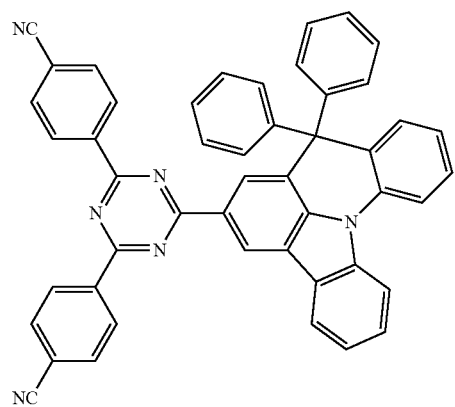

-continued
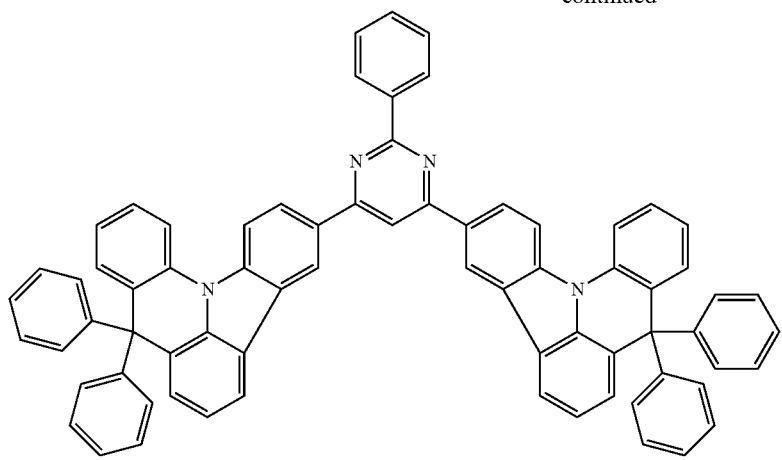
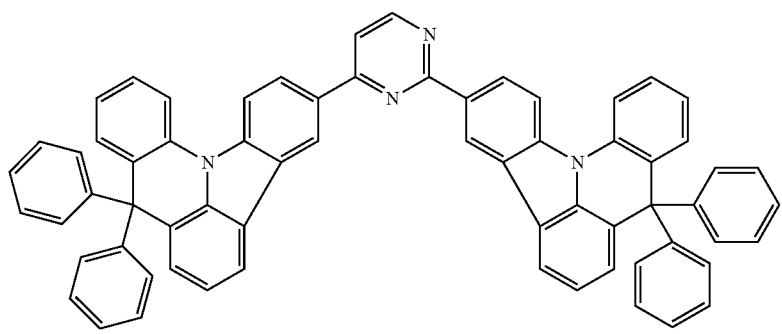
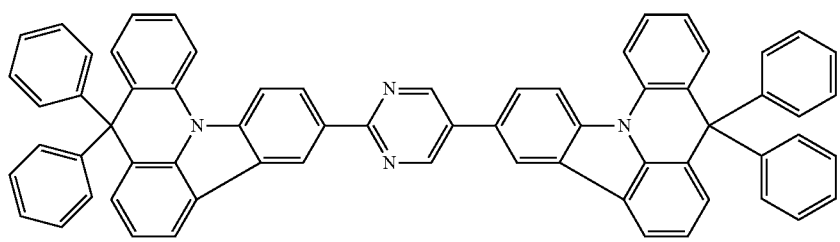
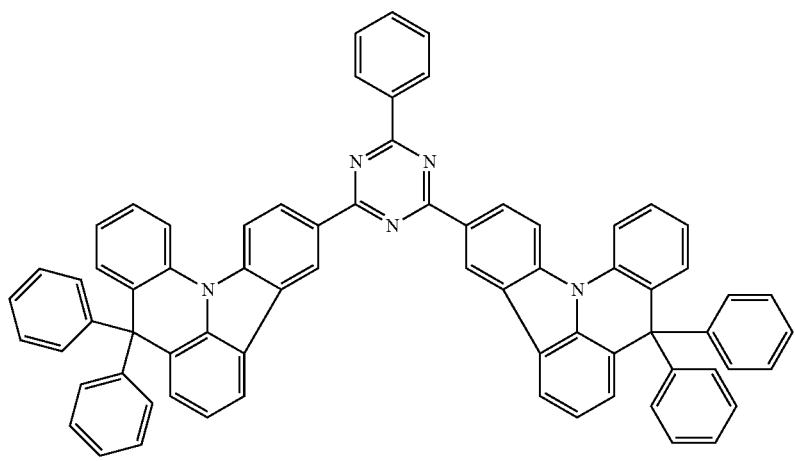

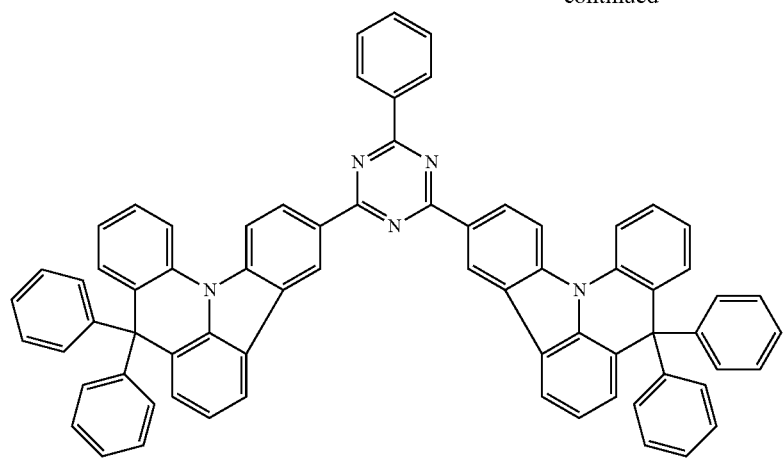
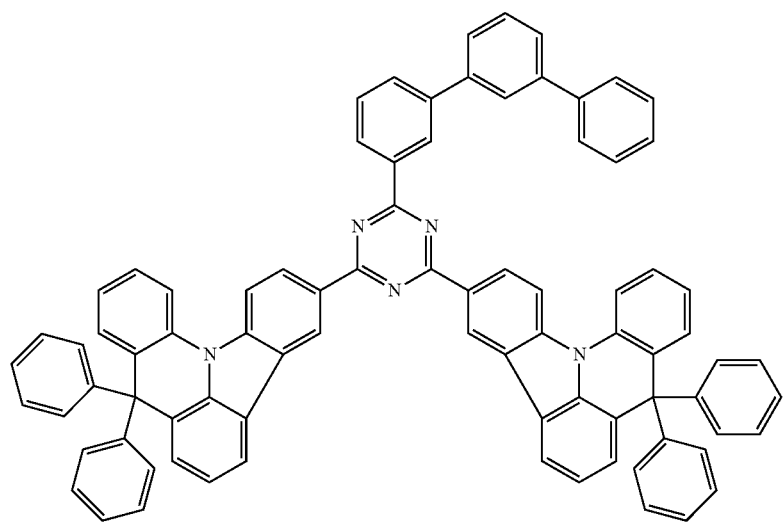
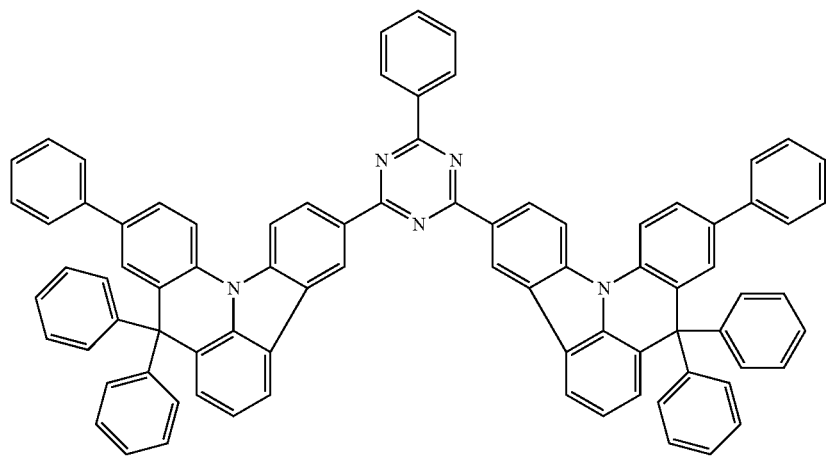

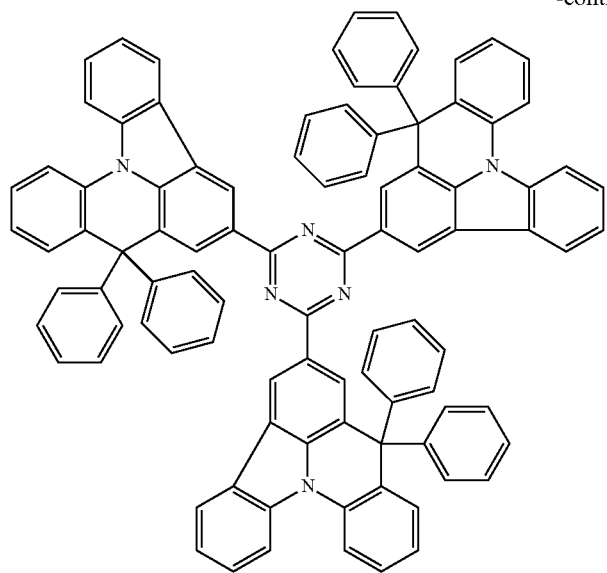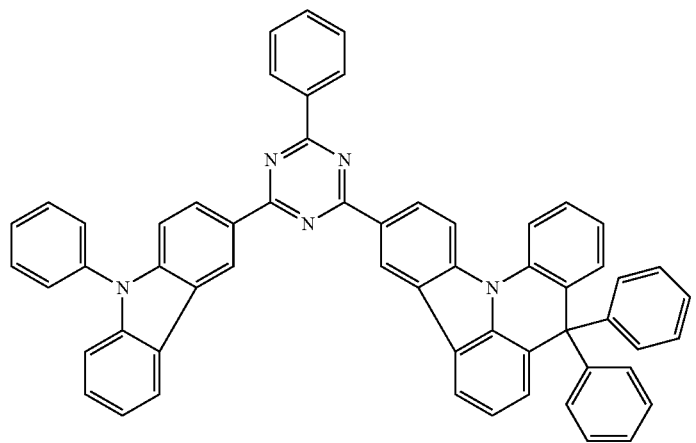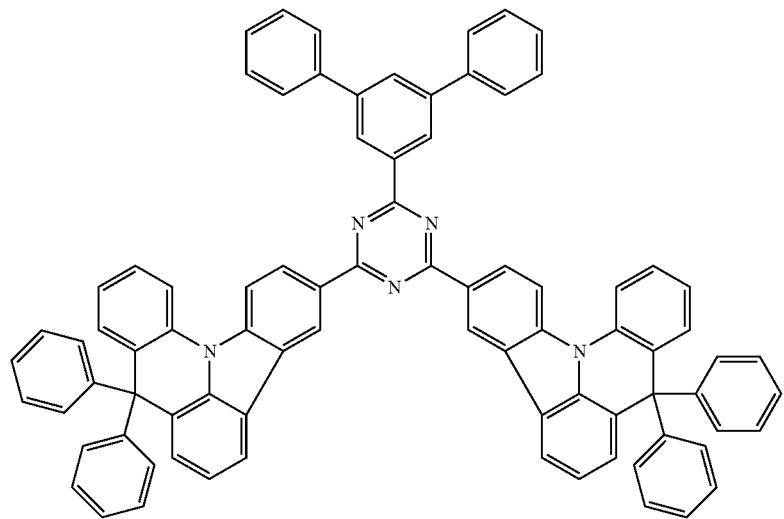

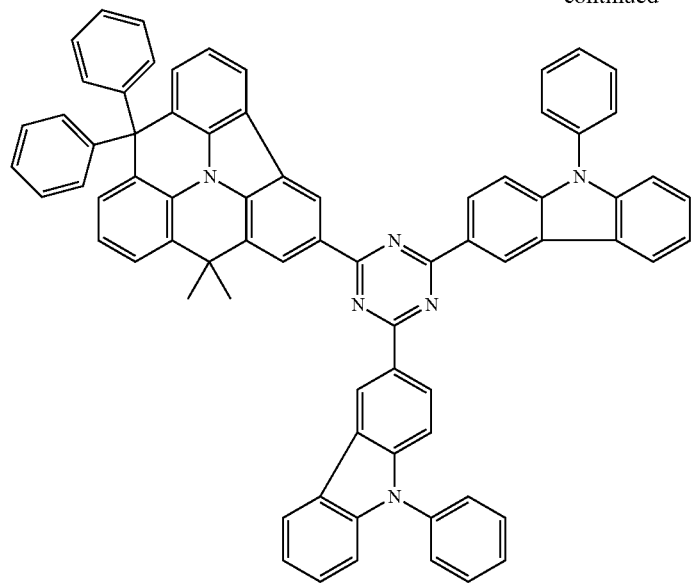

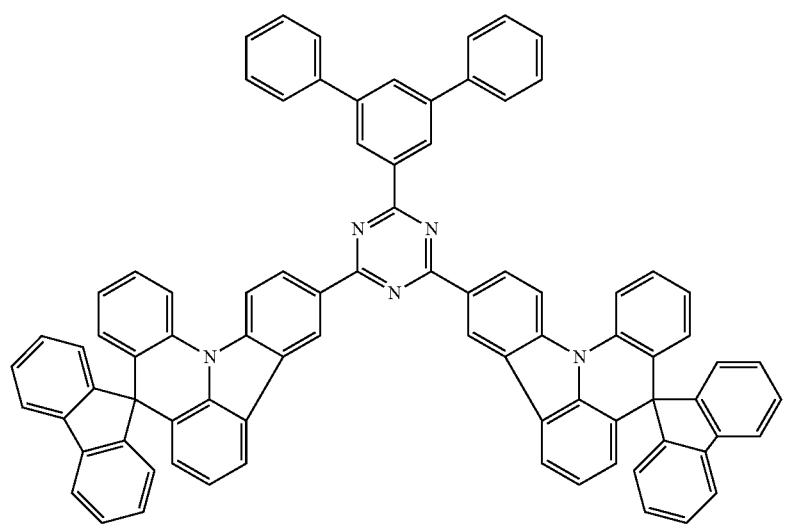

The basic structures of the compounds according to the invention can be prepared by synthetic steps known to the person skilled in the art, such as, for example, bromination, Ullmann arylation, Hartwig-Buchwald coupling, etc., as depicted in Schemes 1 to 4. These basic structures can be functionalised in a further step. Thus, the bromination of carbazole derivatives which have one or two bridges Y results in mono- or di-p-bromine-substituted bridged carbazole derivatives. Besides elemental bromine, the brominating agents used can also be, in particular, N-bromo compounds, such as N-bromosuccinimide (NBS). Functionalisation using other reactive groups, for example chlorine, iodine, boronic acid or boronic acid derivatives, in particular boronic acid esters, triflate or tosylate, is likewise suitable.

Depending on the desired bromine substitution, cyclisation via the intermediate of a tertiary alcohol can be carried out before (Scheme 1) or after (Scheme 2) bromination of the carbazole. The ring closure forms a divalent bridge between the aromatic substituent and the carbazole (see Schemes 1-4). Suitable here is, for example, a carboxylate group or an acetyl group, which can then be converted into a carbon bridge in the ring-closure reaction (Schemes 1 and 2). R in the schemes stands for a substituent as defined above.

Scheme 1

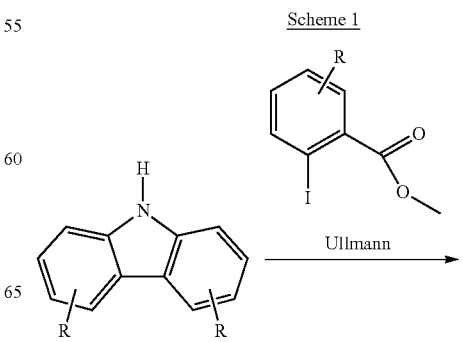

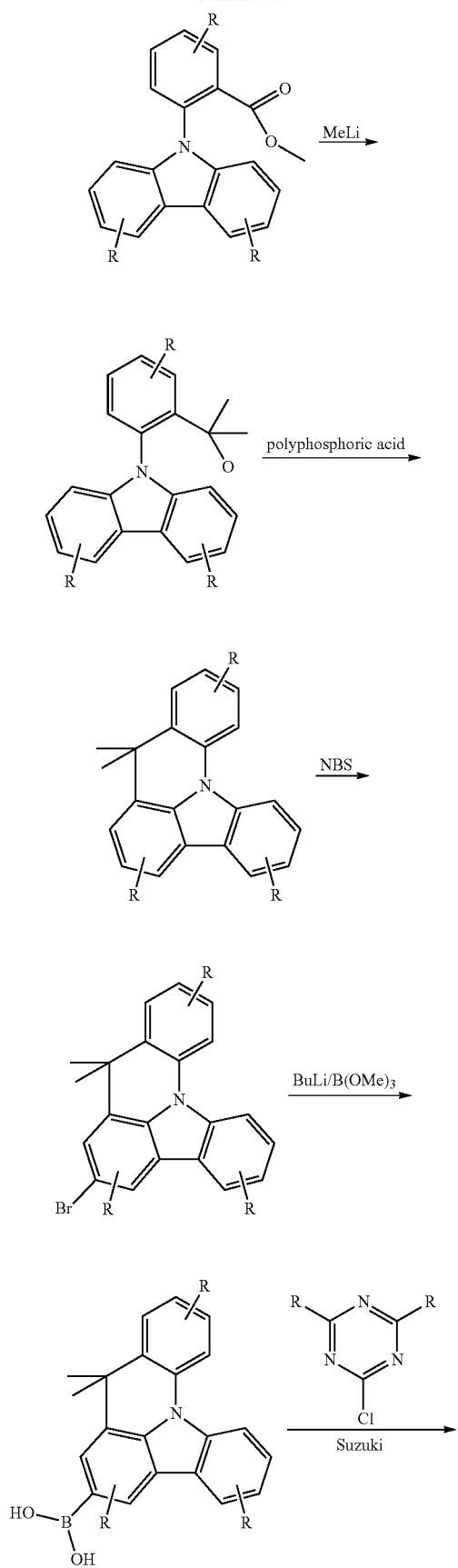
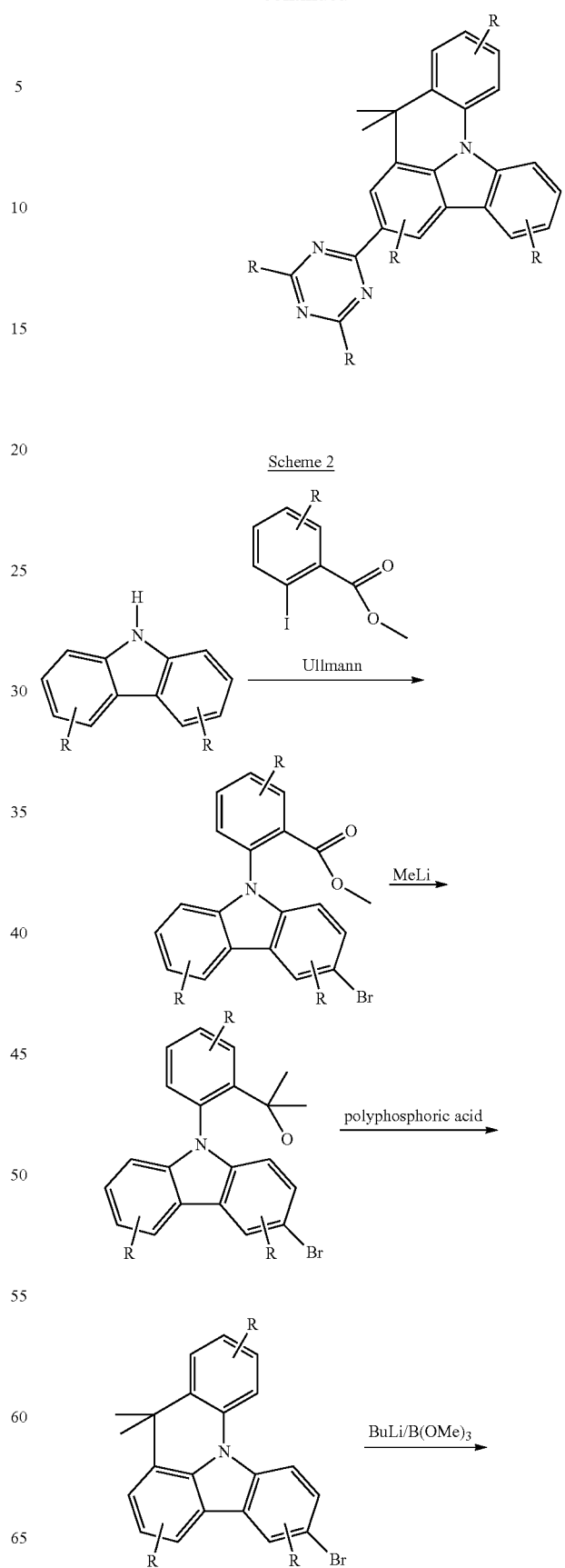
Scheme 2

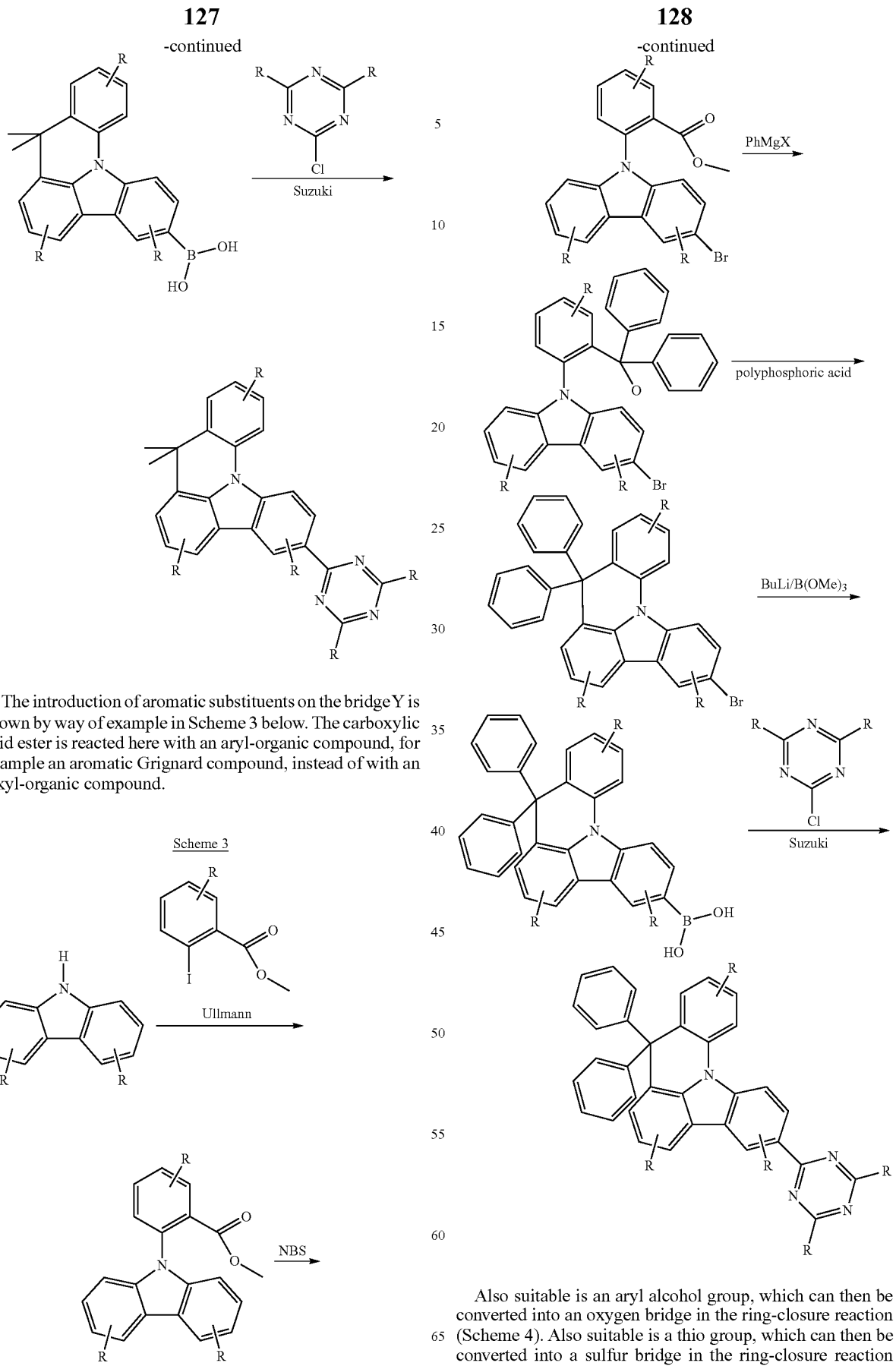

The introduction of aromatic substituents on the bridge Y is shown by way of example in Scheme 3 below. The carboxylic acid ester is reacted here with an aryl-organic compound, for example an aromatic Grignard compound, instead of with an alkyl-organic compound.

Also suitable is an aryl alcohol group, which can then be converted into an oxygen bridge in the ring-closure reaction (Scheme 4). Also suitable is a thio group, which can then be converted into a sulfur bridge in the ring-closure reaction (Scheme 4). Also suitable are a nitro group or amino group, which can then be converted into a nitrogen bridge in the ring-closure reaction (Scheme 5). The divalent bridge can subsequently be substituted by further radicals, for example by alkyl or aryl groups. The bridged carbazole compound prepared in this way can then be functionalised, for example halogenated, preferably brominated, in a further step.
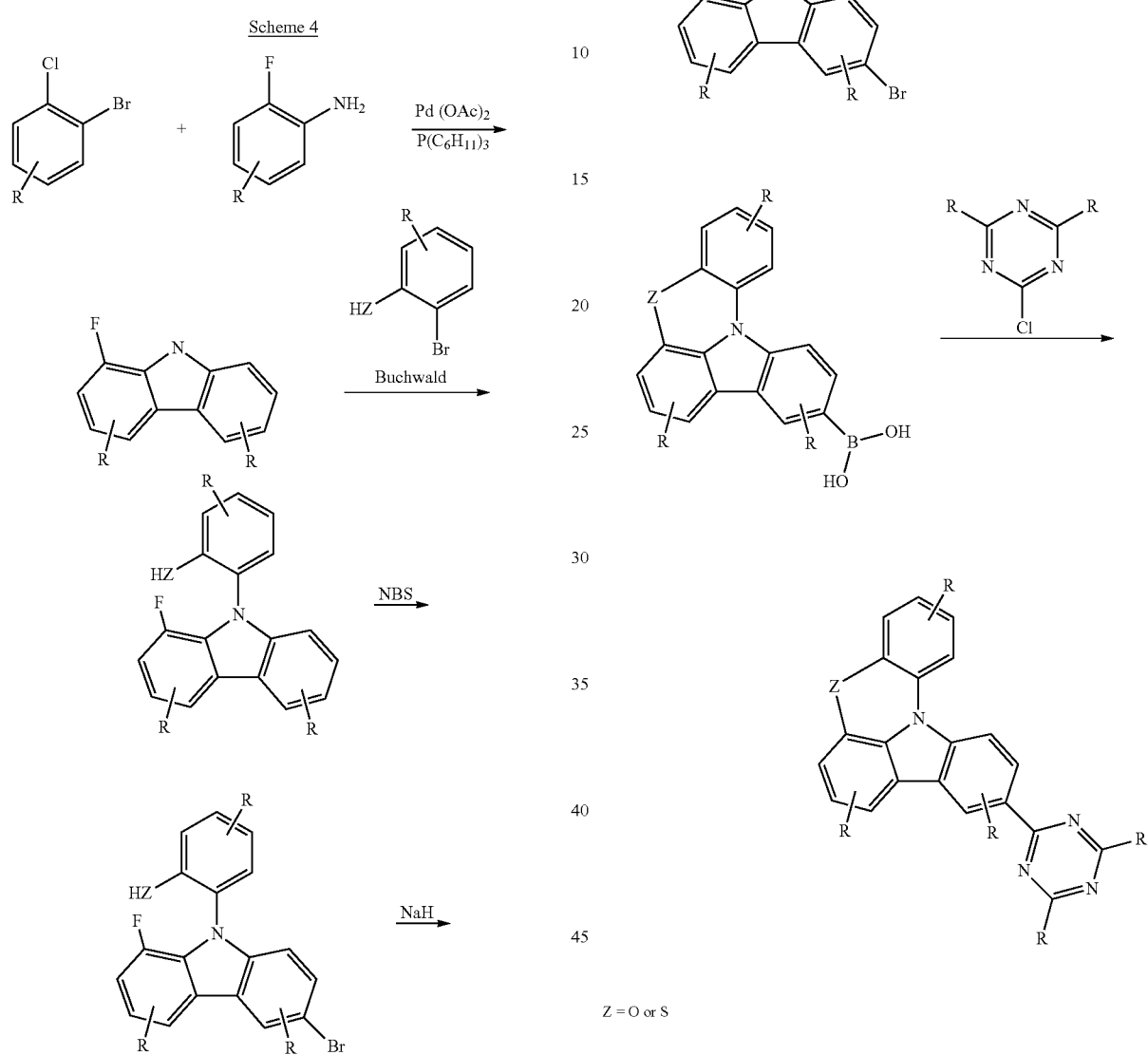
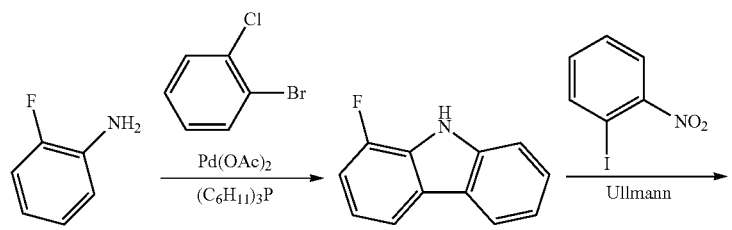

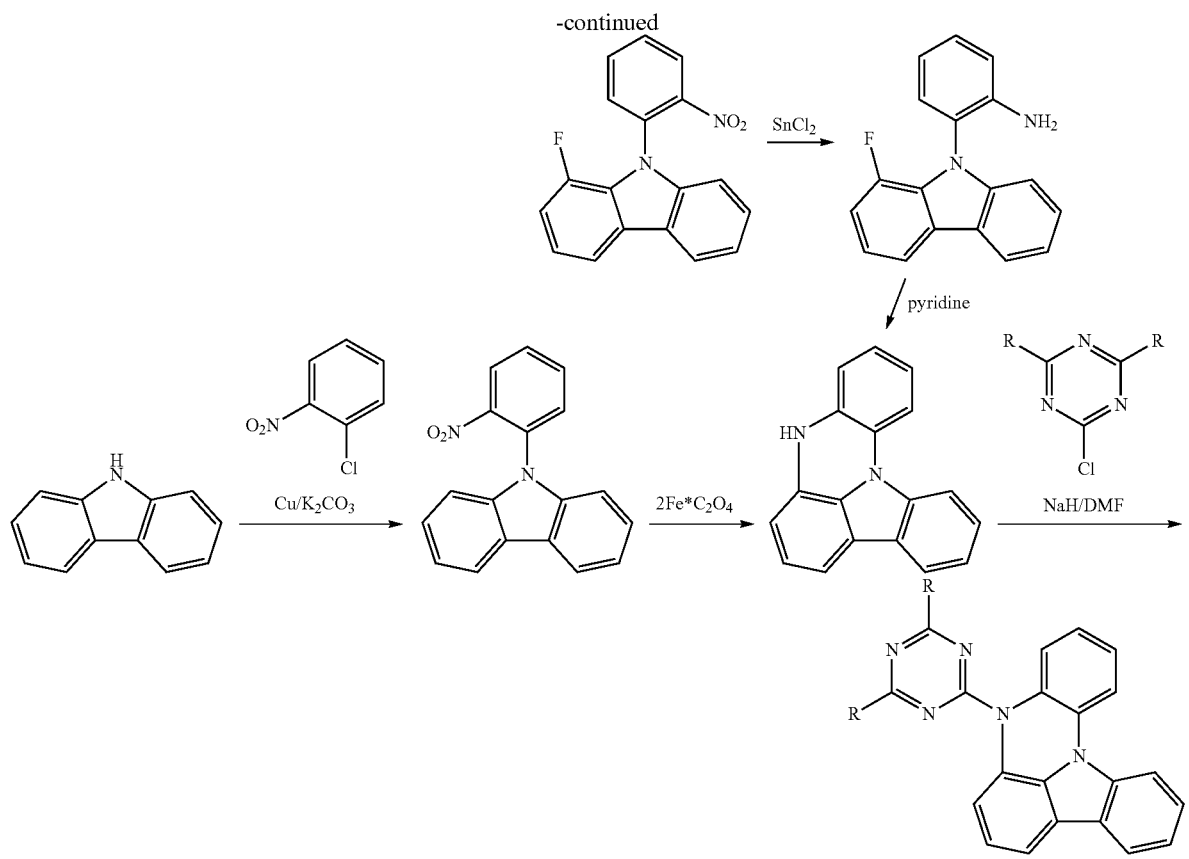

The functionalised, in particular brominated, compounds represent the central unit for further functionalisation, as depicted in Schemes 1 to 4. Thus, these functionalised, bridged compounds can easily be converted into corresponding boronic acids and converted into compounds of the formula (1) according to the invention, for example by Suzuki coupling to 2-chloro-4,6-diphenyl-1,3,5-triazine or other chlorotriazine derivatives.

Likewise, other coupling reactions (for example Stille coupling, Heck coupling, Sonogashira coupling, etc.) can be used. Coupling to diarylamines by the Hartwig-Buchwald method results in triarylamine derivatives. Correspondingly, aliphatic amines, carbazoles, etc., can be introduced as substituents. Formyl, alkylcarbonyl and arylcarbonyl groups or protected analogues thereof, for example in the form of the corresponding dioxolanes, are furthermore suitable as functionalisation. The brominated compounds can furthermore be lithiated and converted into ketones by reaction with electrophiles, such as benzonitrile, and subsequent acidic hydrolysis or into phosphine oxides by reaction with chlorodiphenylphosphines and subsequent oxidation.

The present invention therefore furthermore relates to a process for the preparation of a compound of the formula (1) or (2), comprising the reaction steps of:
a) synthesis of the basic structure which carries a reactive leaving group instead of the group R; and
b) introduction of the group R, preferably by a coupling reaction, for example Suzuki coupling or Hartwig-Buchwald coupling.

The reactive leaving group here is preferably selected from Cl, Br, I, boronic acid or boronic acid derivatives, triflate or tosylate, or Y stands for NH, i.e. the reactive leaving group is hydrogen if a bond is formed between N and R.

The compounds according to the invention described above, in particular compounds which are substituted by reactive leaving groups, such as bromine, iodine, chlorine, boronic acid or boronic acid ester, or by reactive, polymerisable groups, such as olefins or oxetanes, can be used as monomers for the preparation of corresponding oligomers, dendrimers or polymers. The oligomerisation or polymerisation here is preferably carried out via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers comprising one or more of the compounds according to the invention mentioned above, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to homopolymers or copolymers, where the units of the formulae (1), (2) and (16) to (82) are present in a proportion of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 00/22026), spirobifluorenes (for example in accordance with EP 707020, EP 894107 or WO 06/061181), para-phenylenes (for example in accordance with WO 92/18552), carbazoles (for example in accordance with WO 04/070772 or WO 04/113468), thiophenes (for example in accordance with EP 1028136), dihydrophenanthrenes (for example in accordance with WO 05/014689), cis- and trans-indenofluorenes (for example in accordance with WO 04/041901 or WO 04/113412), ketones (for example in accordance with WO 05/040302), phenanthrenes (for example in accordance with WO 05/104264 or WO 07/017066) or also a plurality of these units. The polymers, oligomers and dendrimers may also comprise further units, for example hole-transport units, in particular those based on triarylamines, and/or electron-transport units. In addition, the polymers can either comprise triplet emitters in copolymerised form or mixed in as a blend. Precisely the combination of units of the formulae (1), (2) and (16) to (82) with triplet emitters gives particularly good results.

Furthermore, the compounds of the formulae (1), (2) and (16) to (82) may also be functionalised further and thus converted into extended structures. An example which may be mentioned here is the reaction with arylboronic acids by the SUZUKI method or with primary or secondary amines by the HARTWIG-BUCHWALD method. Thus, the compounds of the formulae (1), (2) and (16) to (82) can also be bonded directly to phosphorescent metal complexes or also to other metal complexes.

The compounds according to the invention are suitable for use in an electronic device. An electronic device here is taken to mean a device which comprises at least one layer which comprises at least one organic compound. The component here may also comprise inorganic materials or also layers built up entirely from inorganic materials.

The present invention therefore furthermore relates to the use of the compounds according to the invention mentioned above in an electronic device, in particular in an organic electroluminescent device.

The present invention again furthermore relates to an electronic device comprising at least one of the compounds according to the invention mentioned above. The preferences stated above likewise apply to the electronic devices.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs), organic laser diodes (O-lasers) and "organic plasmon emitting devices" (D. M. Koller et al., Nature Photonics 2008, 1-4), but preferably organic electroluminescent devices (OLEDs), particularly preferably phosphorescent OLEDs.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 05/011013). It is likewise possible to dope a plurality of emitters into an emitting layer and thus to generate white emission from one layer.

The compound according to the invention in accordance with the embodiments indicated above can be employed in various layers, depending on the precise structure. Preference is given to an organic electroluminescent device comprising a compound of the formula (1), (2) or (16) to (82) as matrix material for fluorescent or phosphorescent emitters, in particular for phosphorescent emitters, and/or in a hole-blocking layer and/or in an electron-transport layer and/or in an electron-blocking or exciton-blocking layer and/or in a hole-transport layer, depending on the precise substitution. The preferred embodiments indicated above also apply to the use of the materials in organic electronic devices.

In a preferred embodiment of the invention, the compound of the formula (1), (2) or (16) to (82) is employed as matrix material for a fluorescent or phosphorescent compound, in particular for a phosphorescent compound, in an emitting layer. The organic electroluminescent device here may comprise one emitting layer or a plurality of emitting layers, where at least one emitting layer comprises at least one compound according to the invention as matrix material.

If the compound of the formula (1), (2) or (16) to (82) is employed as matrix material for an emitting compound in an emitting layer, it is preferably employed in combination with one or more phosphorescent materials (triplet emitters). Phosphorescence in the sense of this invention is taken to mean the luminescence from an excited state of relatively high spin multiplicity, i.e. a spin state >1, in particular from an excited triplet state. For the purposes of this application, all luminescent complexes containing transition metals, in particular all iridium, platinum and copper complexes, are to be regarded as phosphorescent compounds.

The mixture of the compound of the formula (1), (2) or (16) to (82) and the emitting compound comprises between 99.9 and 1% by vol., preferably between 99 and 10% by vol., particularly preferably between 97 and 60% by vol., in particular between 95 and 80% by vol., of the compound of the formula (1), (2) or (16) to (82), based on the entire mixture comprising emitter and matrix material. Correspondingly, the mixture comprises between 0.1 and 99% by vol., preferably between 1 and 90% by vol., particularly preferably between 3 and 40% by vol., in particular between 5 and 20% by vol., of the emitter, based on the entire mixture comprising emitter and matrix material.

A further preferred embodiment of the present invention is the use of the compound of the formula (1), (2) or (16) to (82) as matrix material for a phosphorescent emitter in combination with a further matrix material. Particularly suitable matrix materials which can be employed in combination with the compounds of the formulae (1), (2) and (16) to (82) are aromatic ketones, aromatic phosphine oxides or aromatic sulfoxides or sulfones, for example in accordance with WO 04/013080, WO 04/093207, WO 06/005627 or WO 10/006680, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086851, indolocarbazole derivatives, example in accordance with WO 07/063754 or WO 08/056746, indenocarbazole derivatives, for example in accordance with the unpublished applications DE 102009023155.2 or DE 102009031021.5, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with WO 10/015306, WO 07/063754 or WO 08/056746, zinc complexes, for example in accordance with EP 652273 or WO 09/062578, diazasilole or tetraazasilole derivatives, for example in accordance with WO 10/054729, or diazaphosphole derivatives, for example in accordance with WO 10/054,730. A further phosphorescent emitter which emits at shorter wavelength than the actual emitter may likewise be present in the mixture as co-host.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80, in particular a metal having this atomic number. The phosphorescence emitters used are preferably compounds which contain copper, molybdenum, tungsten, rhenium, ruthenium, osmium, rhodium, iridium, palladium, platinum, silver, gold or europium, in particular compounds which contain iridium or platinum.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescence are suitable, and the person skilled in the art will be able to use further phosphorescent complexes without inventive step.

Examples of suitable phosphorescent compounds are listed in the following table.

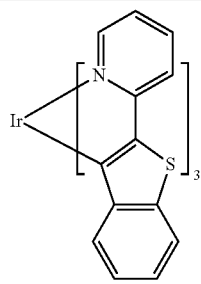

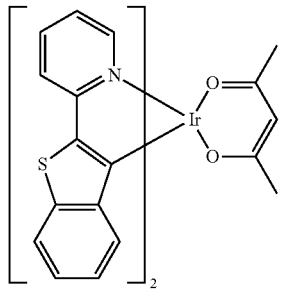

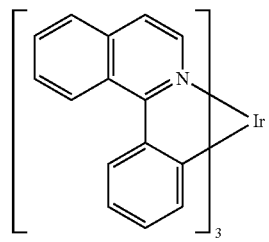

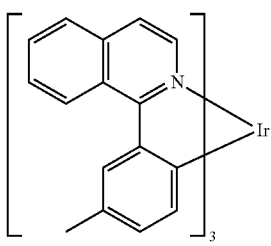

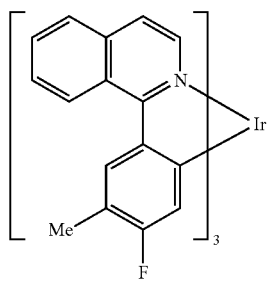

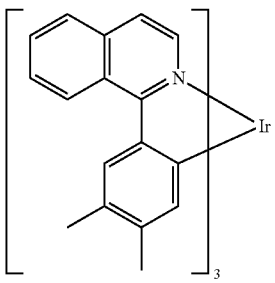

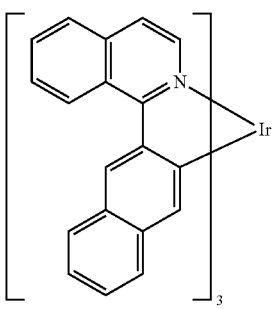

137
-continued
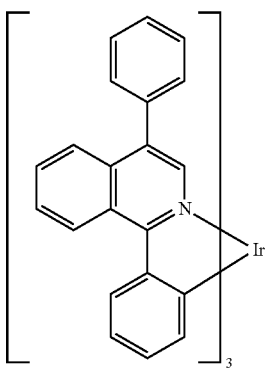
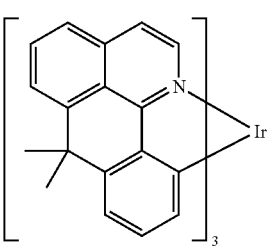
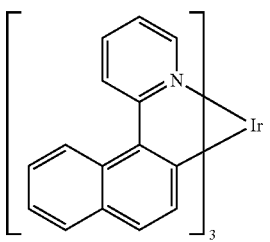
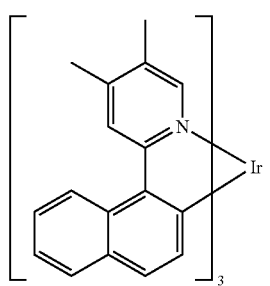
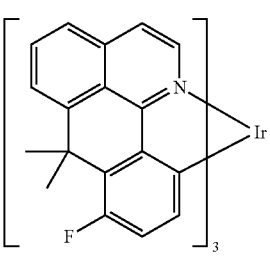
138
-continued
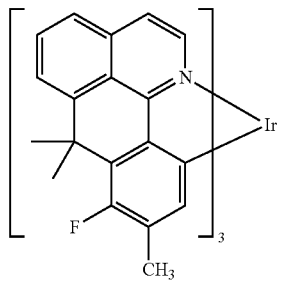
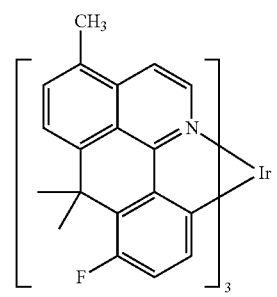
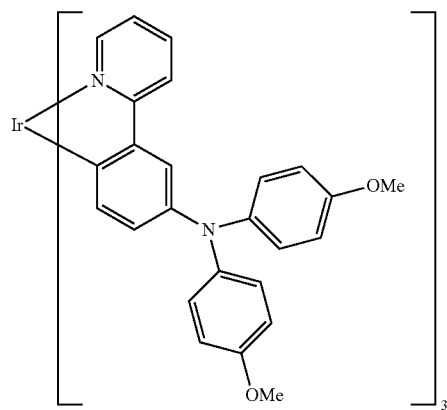
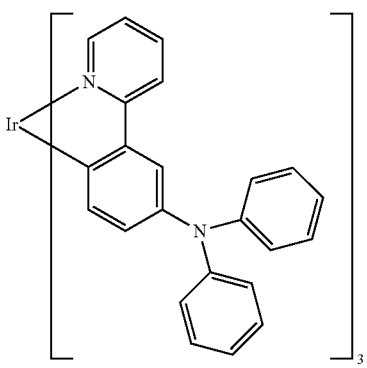

139
-continued
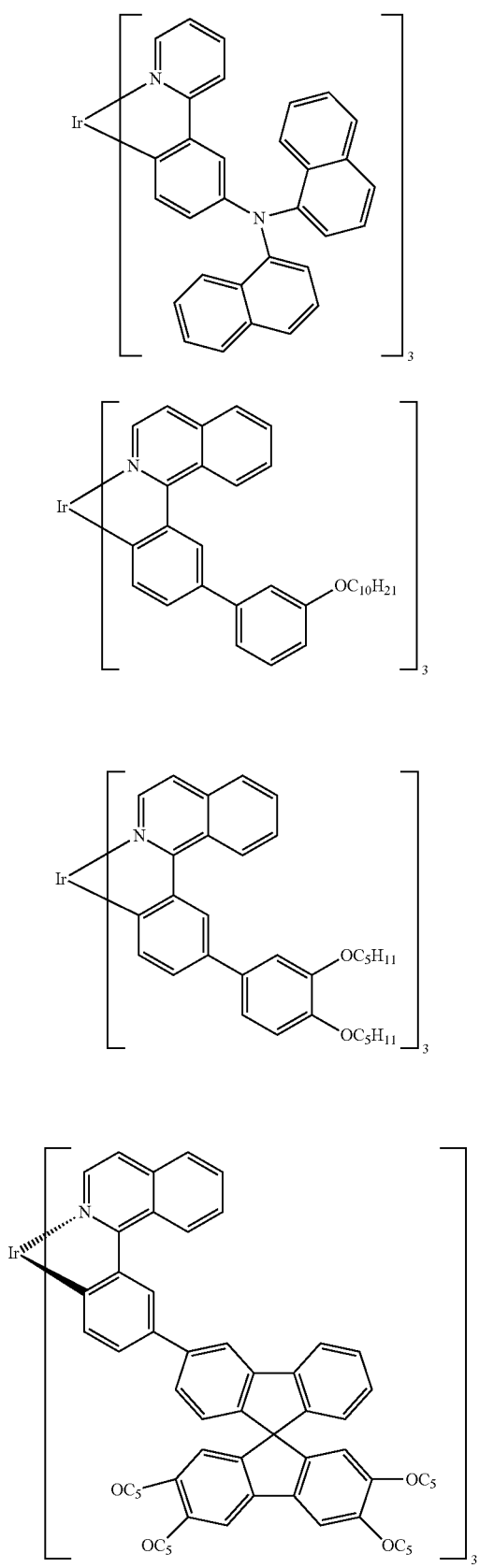
140
-continued
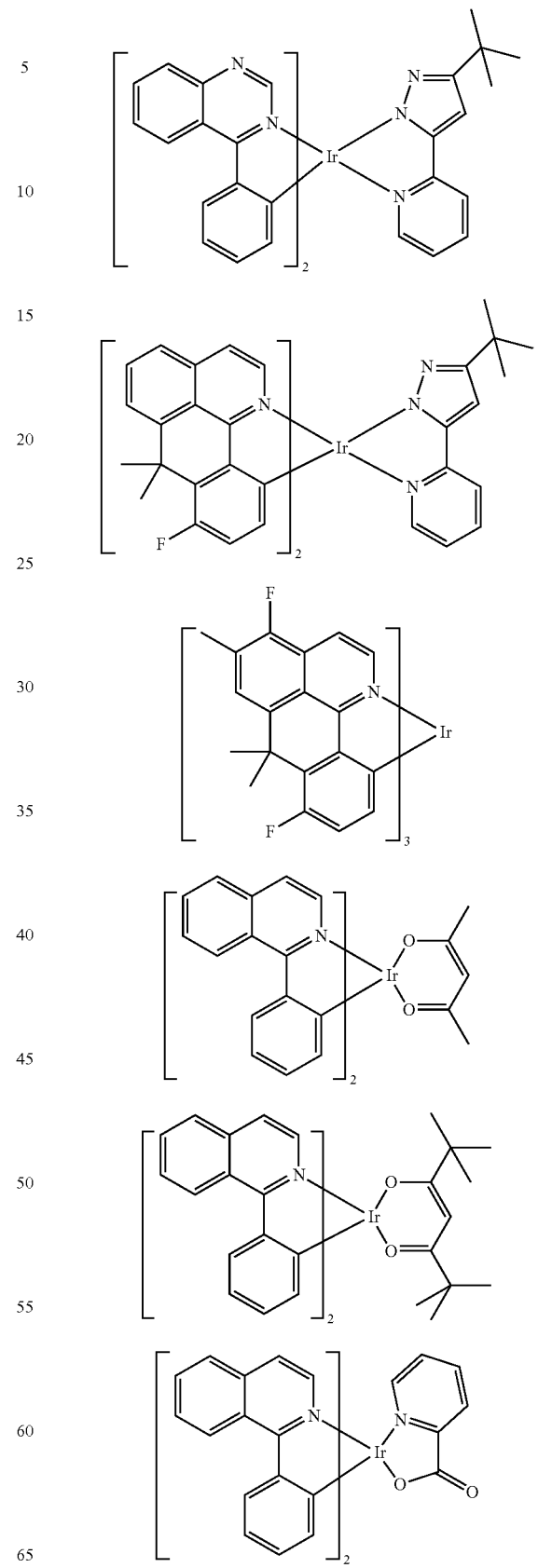

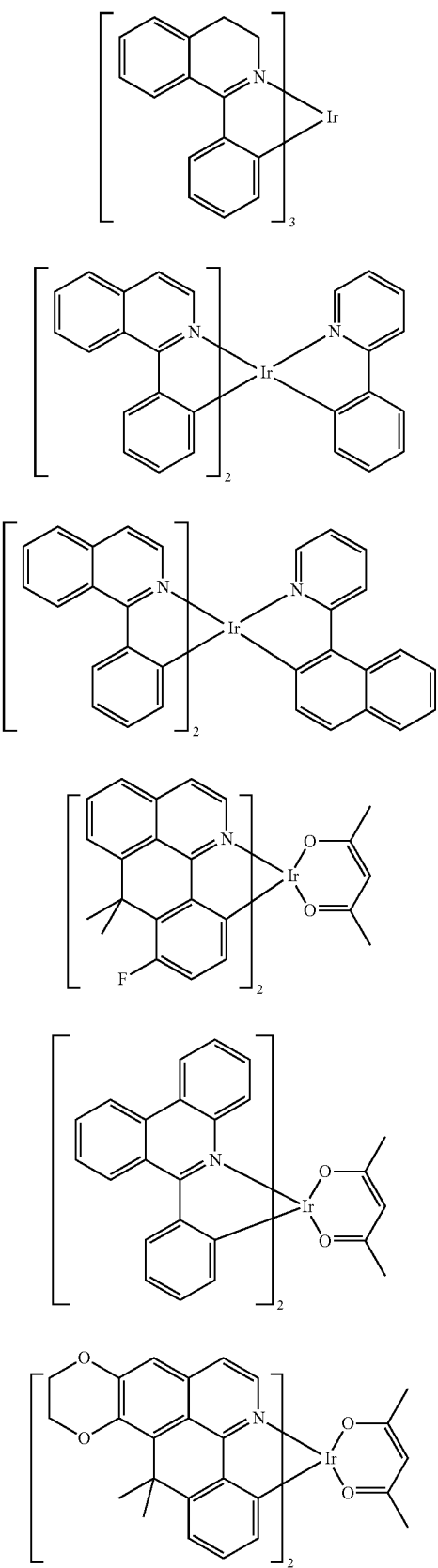
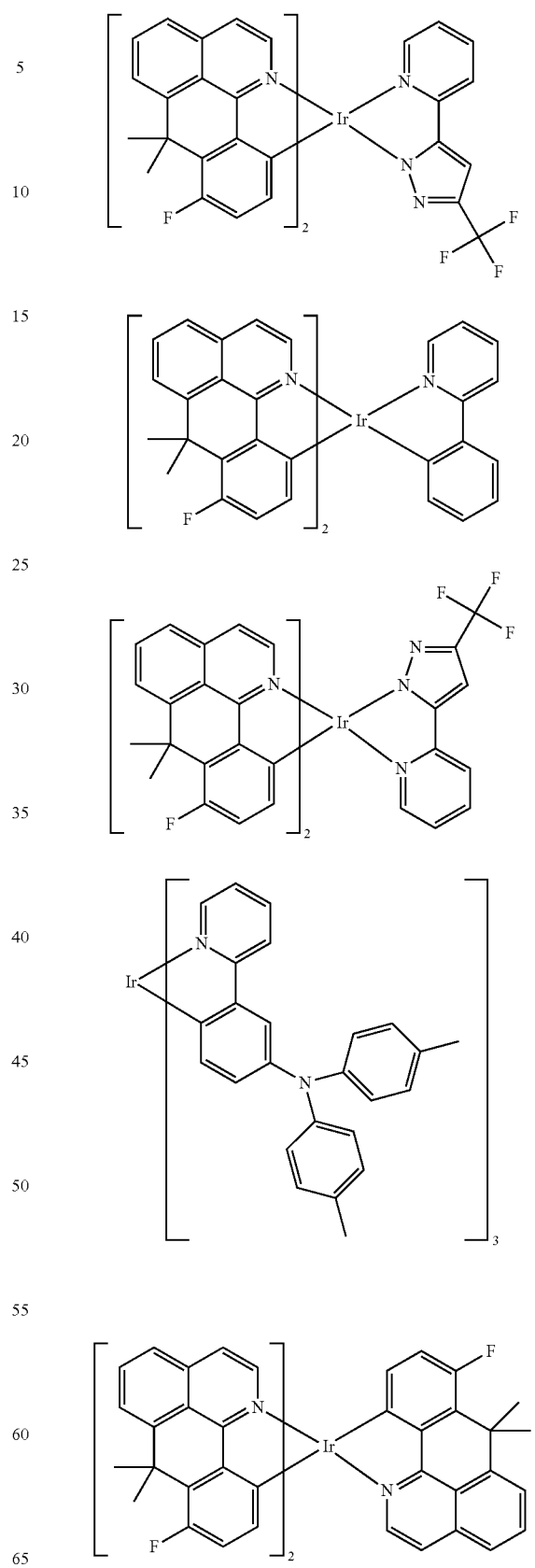

143
-continued
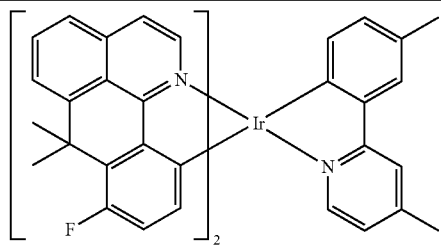
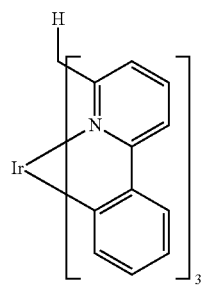
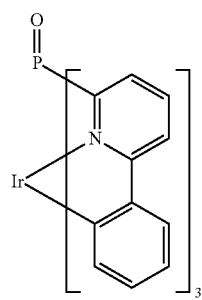
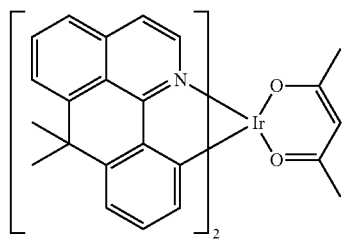
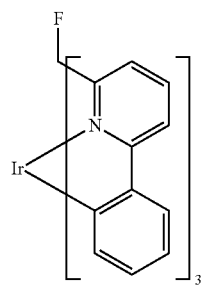
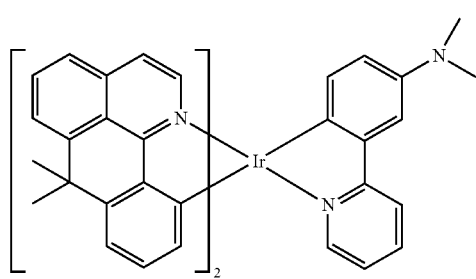
144
-continued
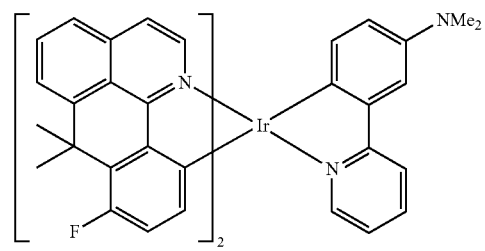
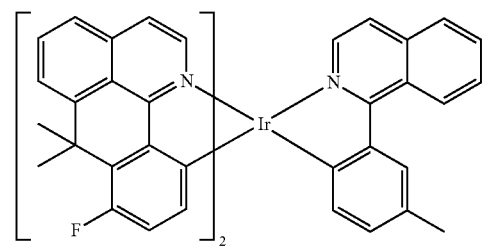
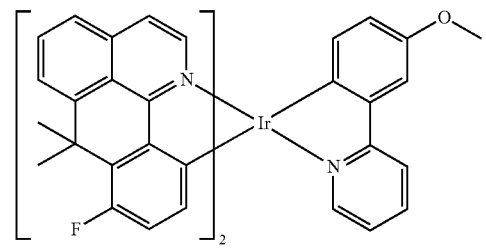
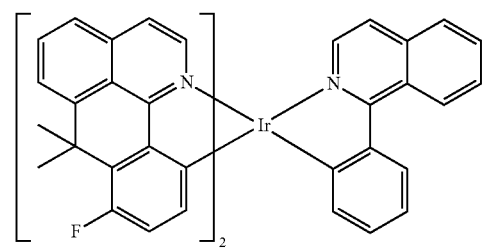
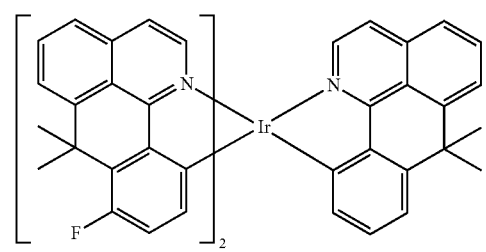
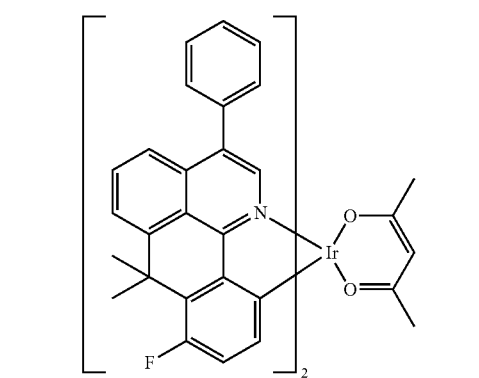

145
-continued
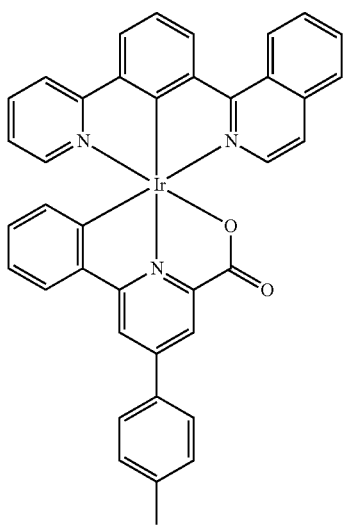
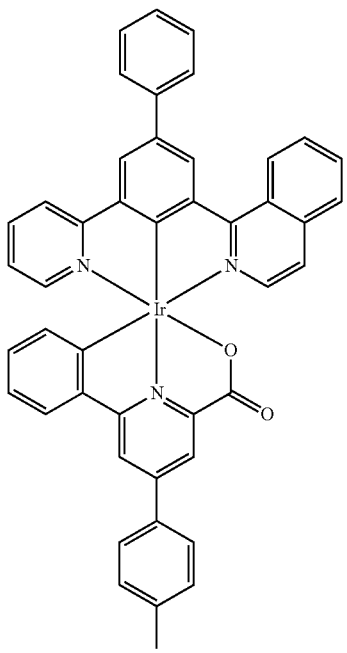
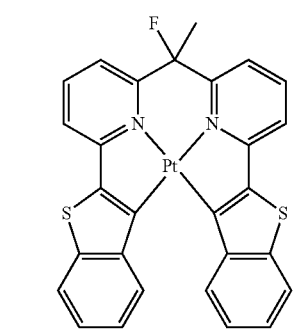
146
-continued
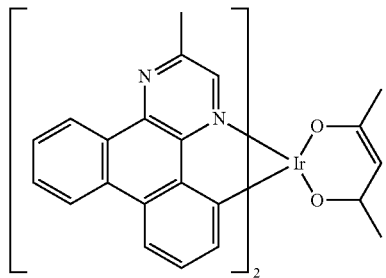
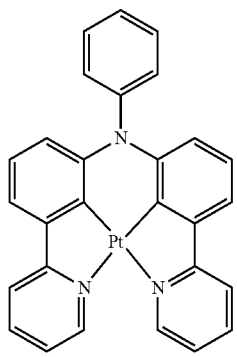
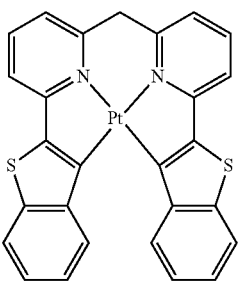
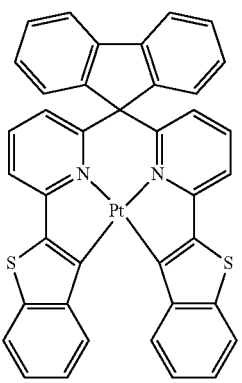
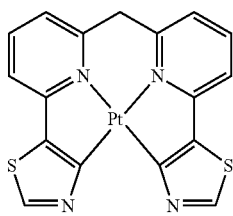

147
-continued
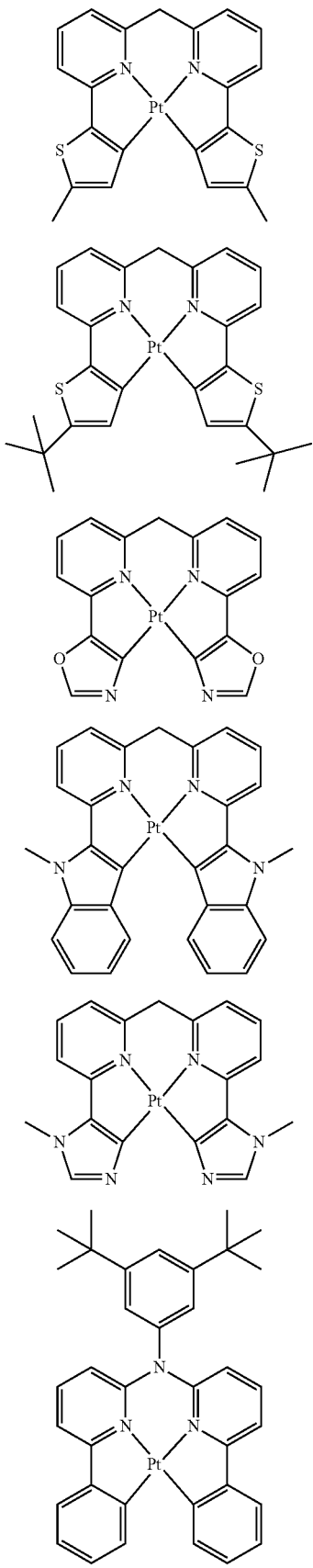
148
-continued
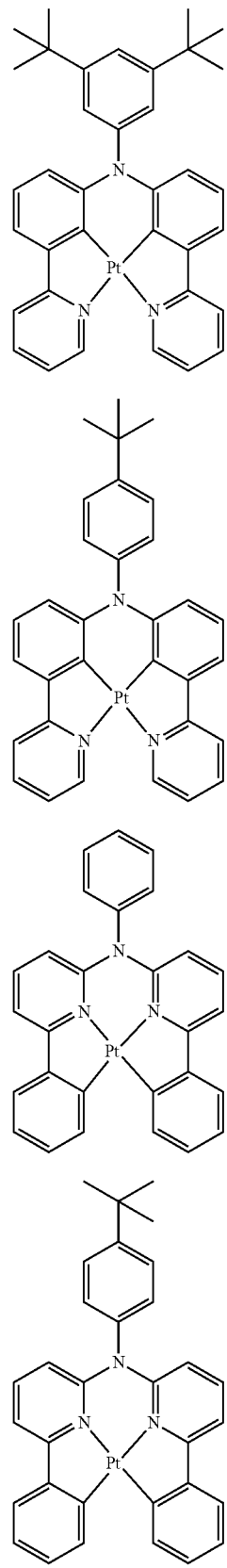

| 149 -continued | 150 -continued |
|---|---|
| 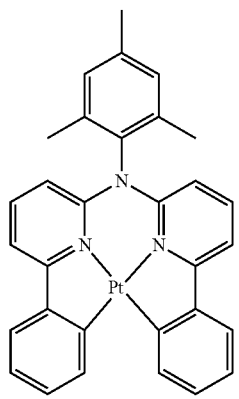 | 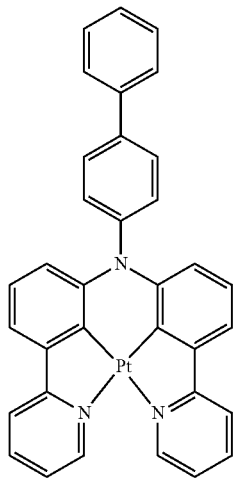 |
| 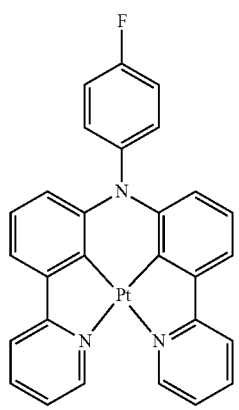 | 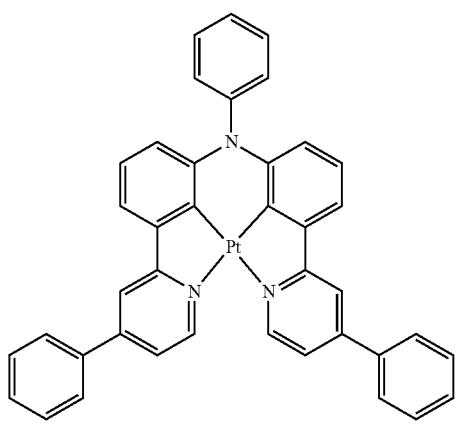 |
| 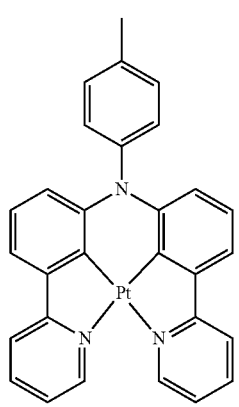 | 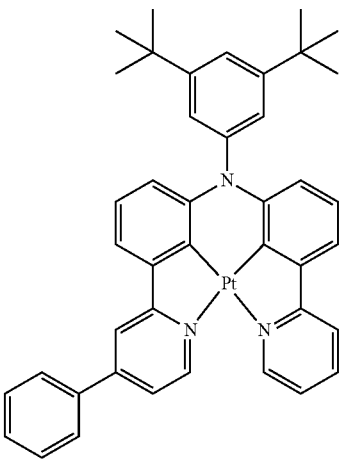 |

| 151 -continued | 152 -continued |
|---|---|
| 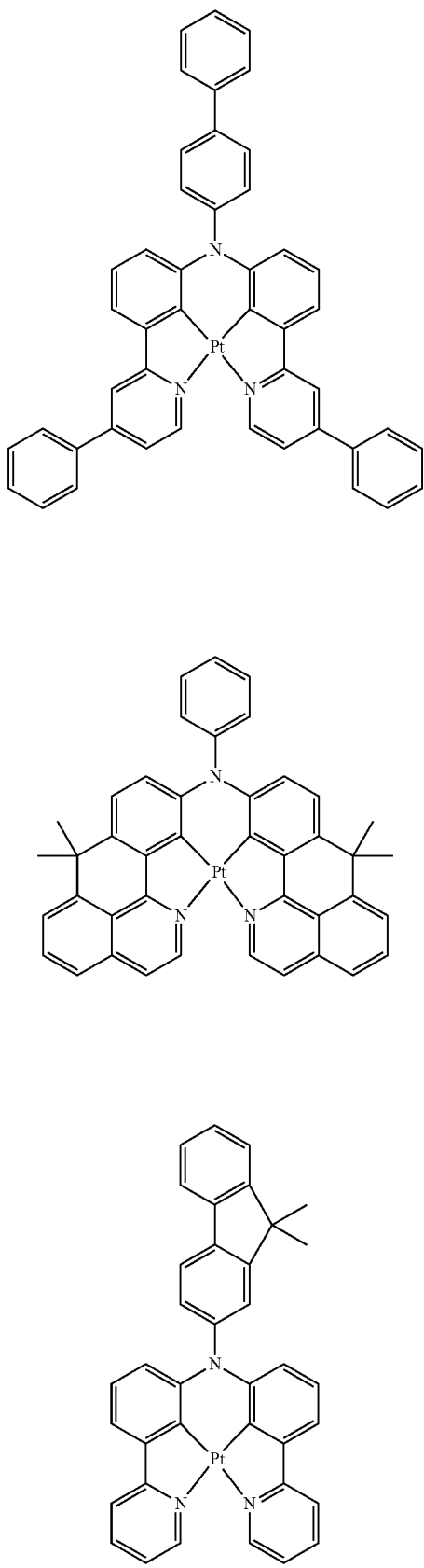 | 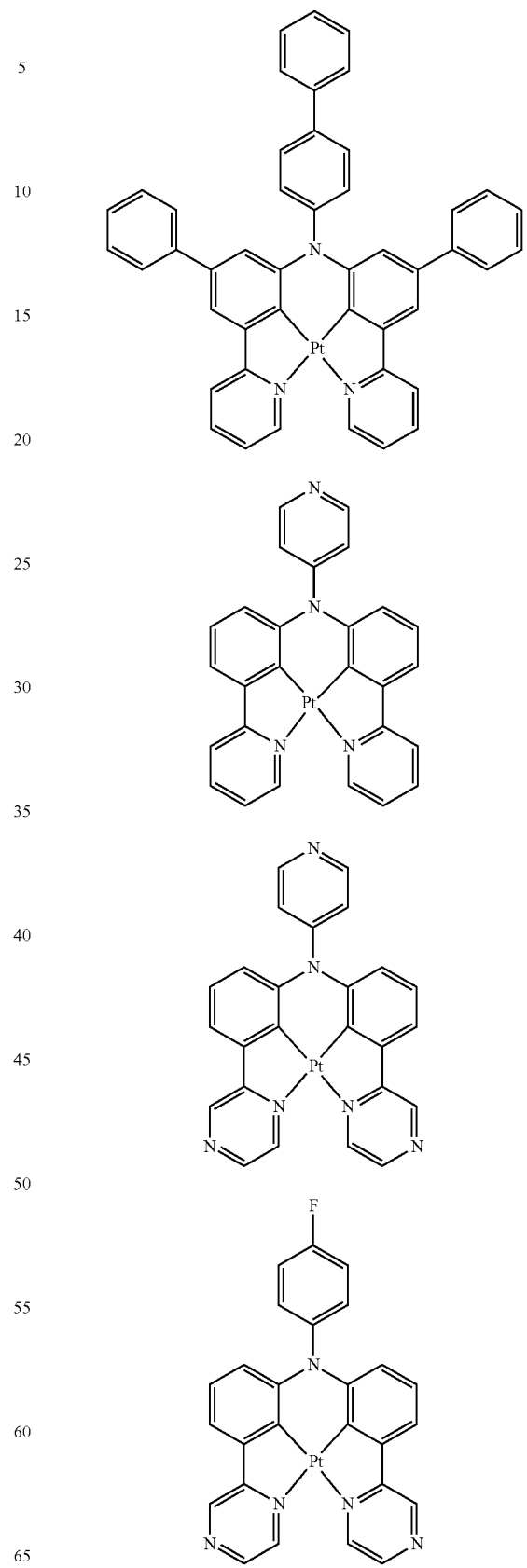 |

153
-continued
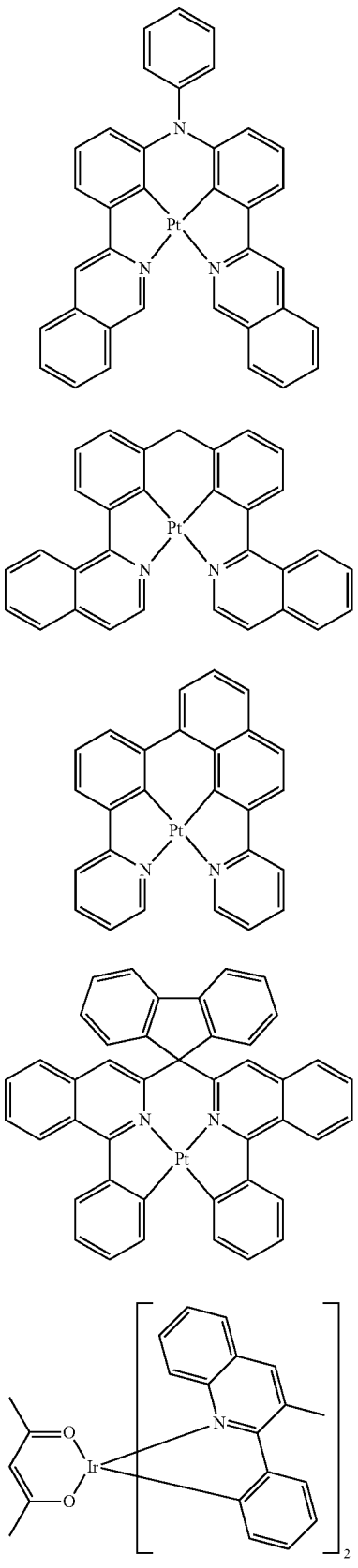
154
-continued
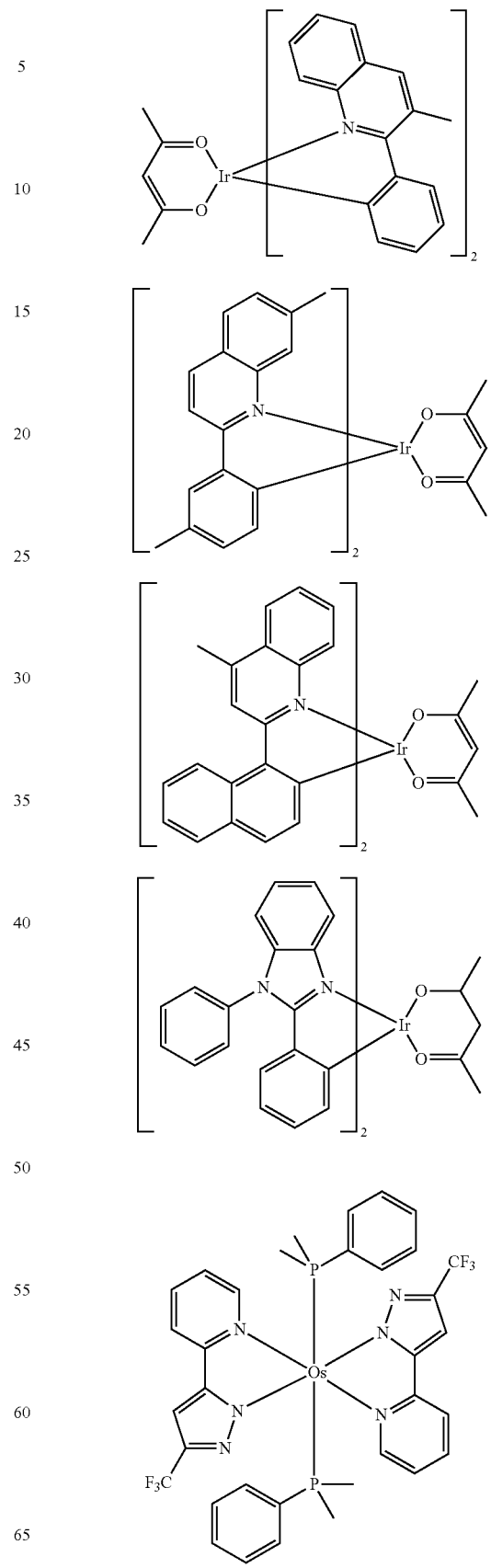

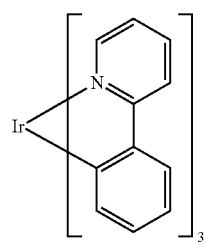
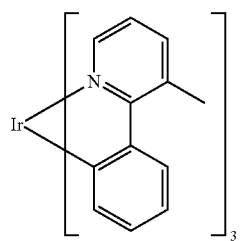
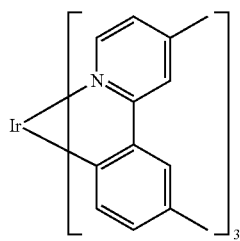
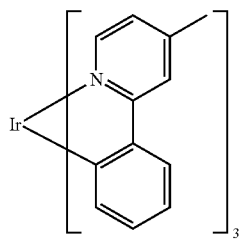
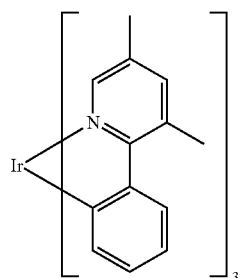
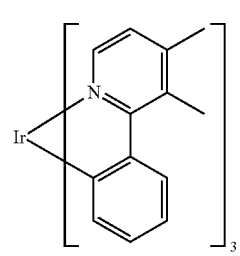
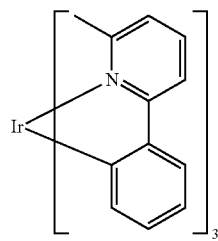
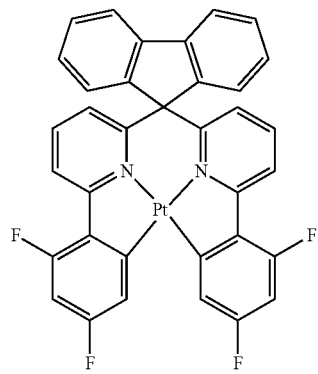
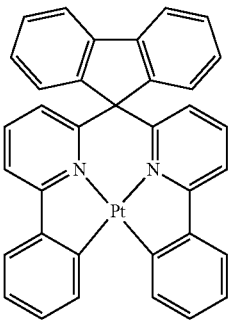
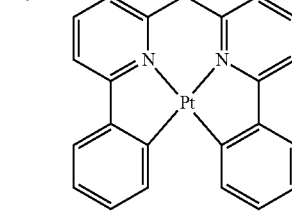
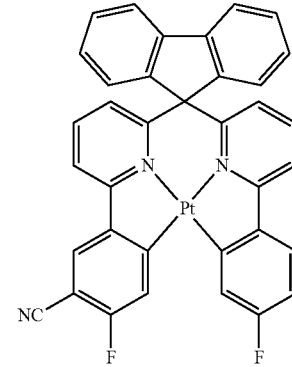

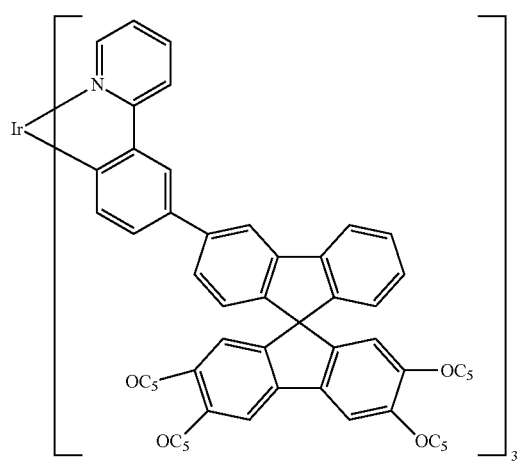
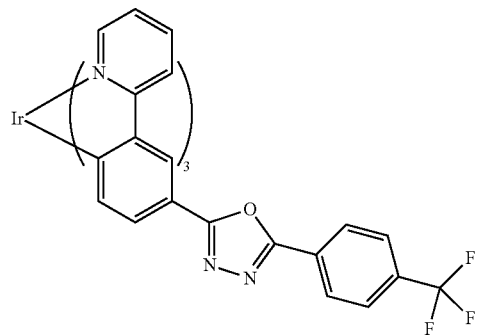
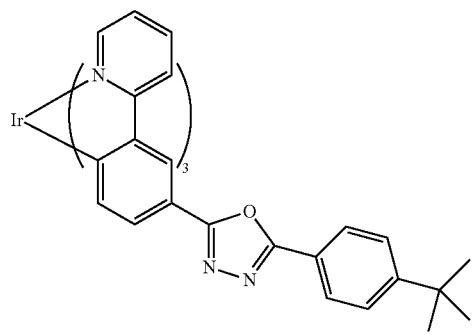
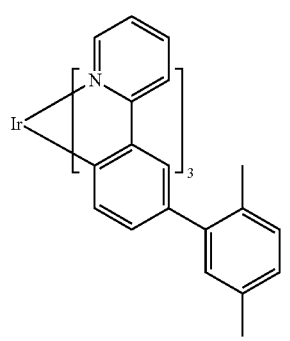
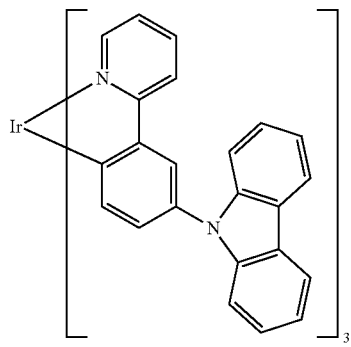
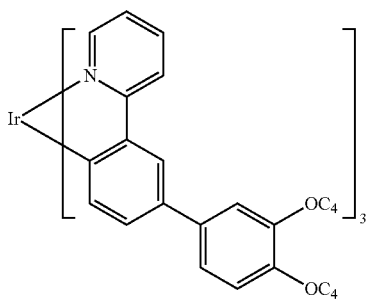
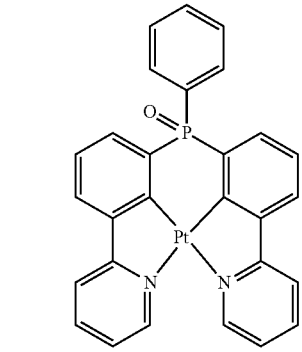
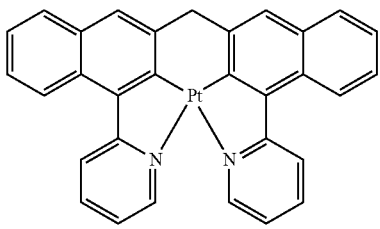
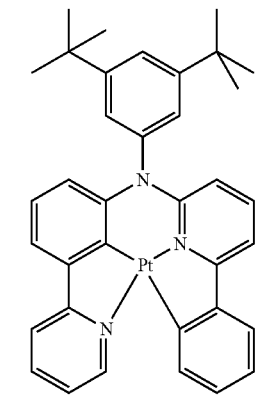

| 159 -continued | 160 -continued |
|---|---|
| 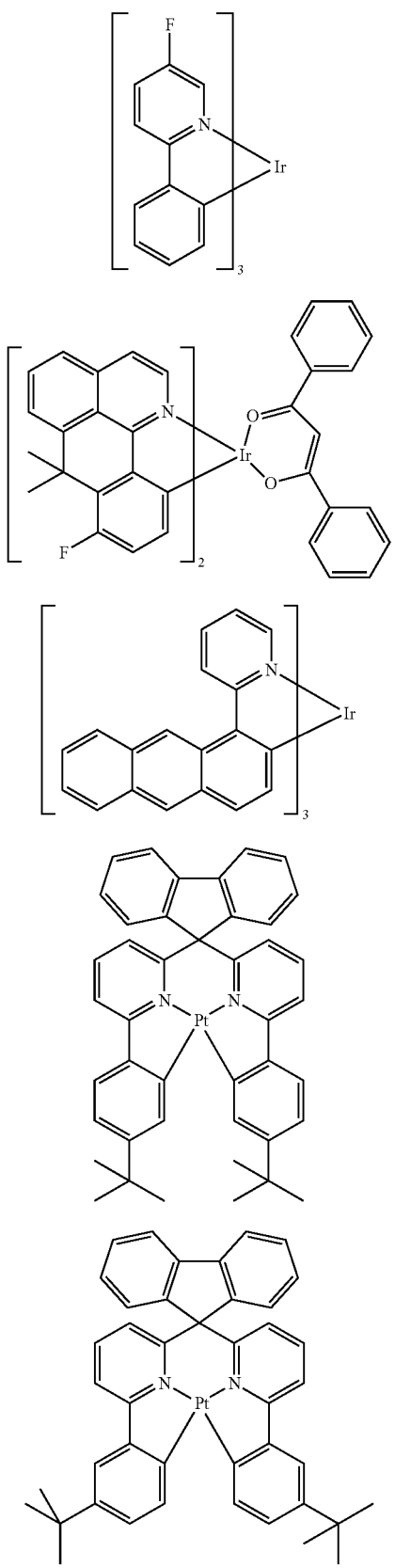 | 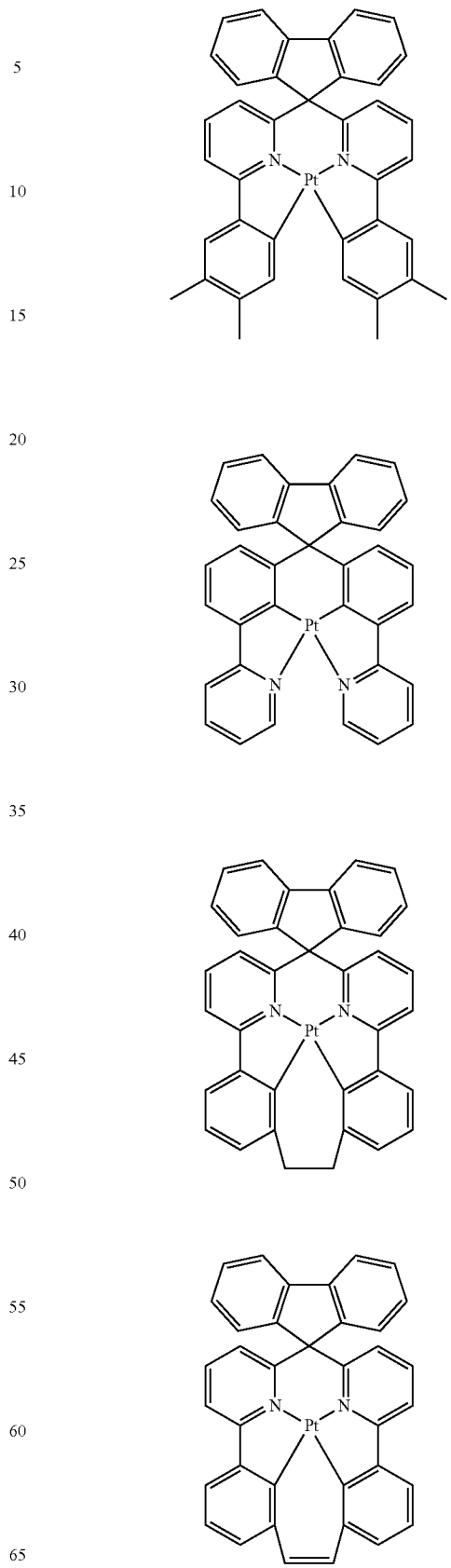 |

161
-continued
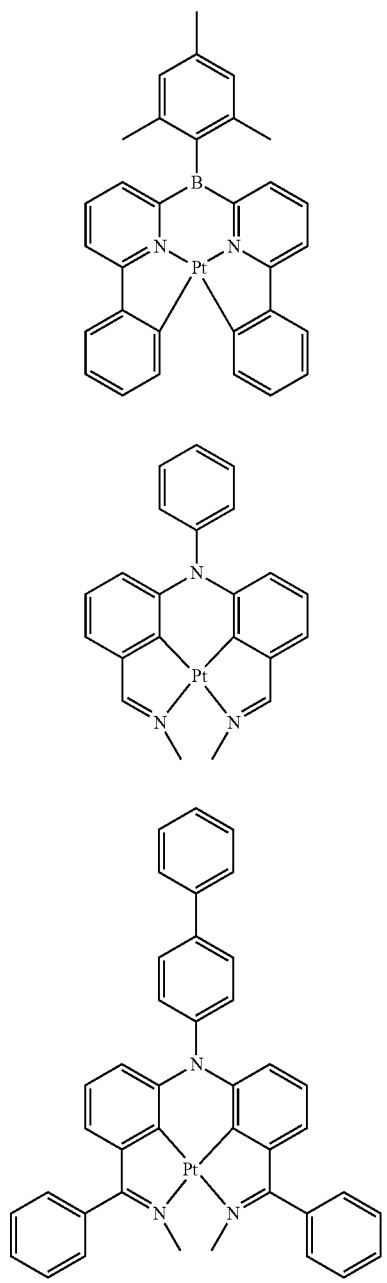
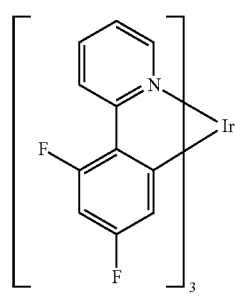
162
-continued
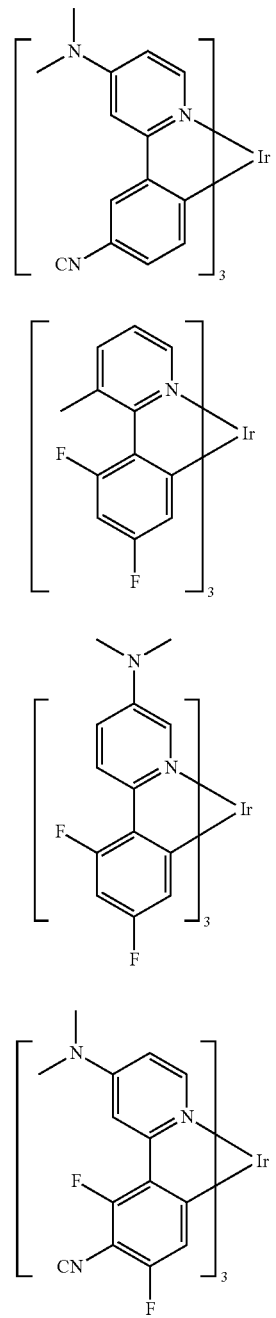
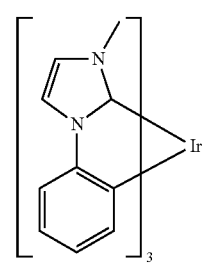

163
-continued
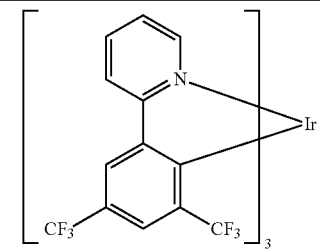
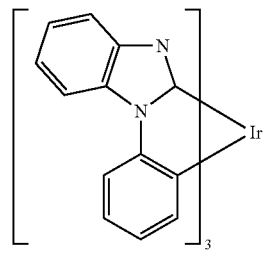
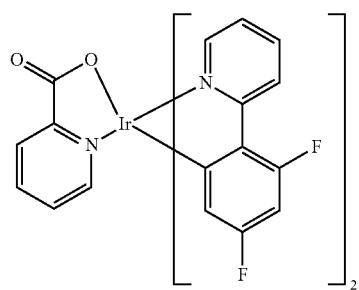
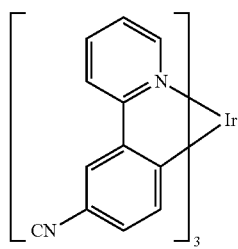
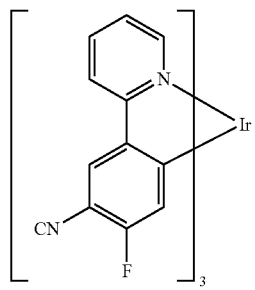
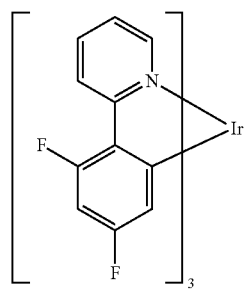
164
-continued
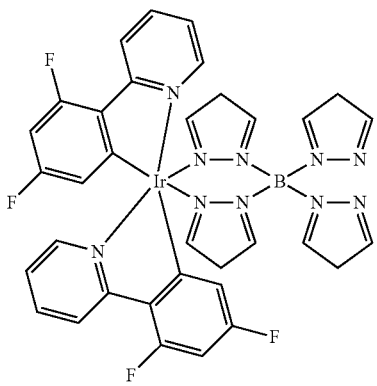
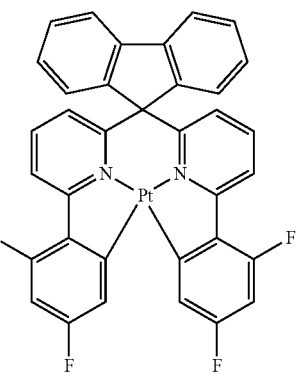
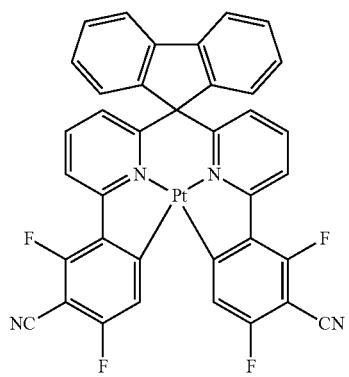
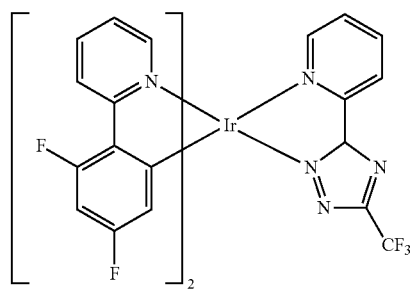

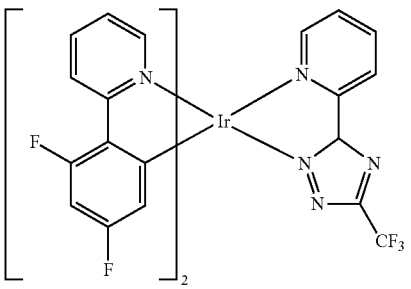

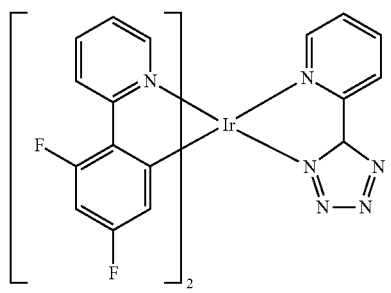

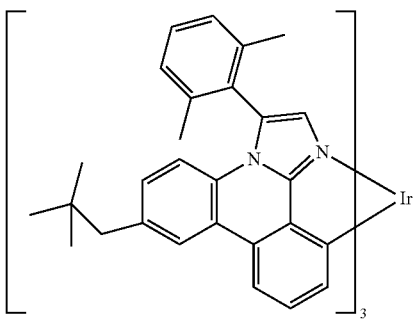

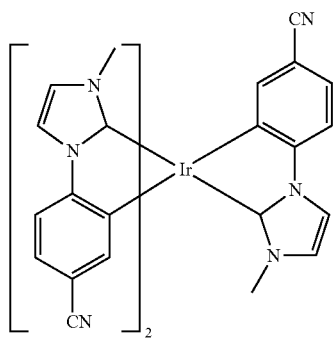

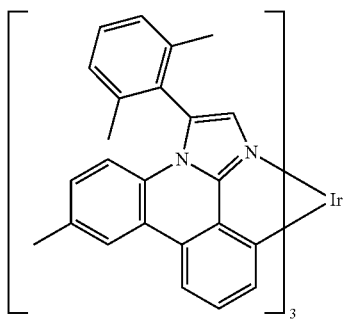

In a further embodiment of the invention, the organic electroluminescent device does not comprise a separate hole-injection layer and/or hole-transport layer and/or hole-blocking layer and/or electron-transport layer, i.e. the emitting layer is directly adjacent to the hole-injection layer or the anode, and/or the emitting layer is directly adjacent to the electron-transport layer or the electron-injection layer or the cathode, as described, for example, in WO 05/053051. It is furthermore possible to use a metal complex which is identical or similar to the metal complex in the emitting layer as hole-transport or hole-injection material directly adjacent to the emitting layer, as described, for example, in WO 09/030981.

In a further preferred embodiment of the invention, the compound of the formula (1), (2) or (16) to (82) is employed as electron-transport material in an electron-transport or electron-injection layer. The emitting layer here may be fluorescent or phosphorescent. If the compound is employed as electron-transport material, it may be preferred for it to be doped, for example with alkali-metal complexes, such as, for example, Liq (lithium hydroxyquinolinate).

In yet a further preferred embodiment of the invention, the compound of the formula (1), (2) or (16) to (82) is employed in a hole-blocking layer. A hole-blocking layer is taken to mean a layer which is directly adjacent to an emitting layer on the cathode side.

It is furthermore possible to use the compound of the formula (1), (2) or (16) to (82) both in a hole-blocking layer or electron-transport layer and as matrix in an emitting layer.

In yet a further embodiment of the invention, the compound of the formula (1), (2) or (16) to (82) is employed in a hole-transport layer or in an electron-blocking layer or exciton-blocking layer.

In the further layers of the organic electroluminescent device according to the invention, it is possible to use all materials as usually employed in accordance with the prior art. The person skilled in the art will therefore be able, without an inventive step, to employ all materials known for organic electroluminescent devices in combination with the compounds of the formulae (1), (2) and (16) to (82) according to the invention.

Preference is furthermore given to an organic electroluminescent device, characterised in that one or more layers are applied by means of a sublimation process, in which the materials are vapour-deposited in vacuum sublimation units at an initial pressure of less than $10^{-5}$ mbar, preferably less than $10^{-6}$ mbar. However, it is also possible for the initial pressure to be even lower, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure between $10^{-5}$ mbar and 1 bar. A special case of this process is the OVJP (organic vapour jet printing) process, in which the materials are applied directly through a nozzle and thus structured (for example M. S. Arnold et al., Appl. Phys. Lett. 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing, LITI (light induced thermal imaging, thermal transfer printing), inkjet printing or nozzle printing. Soluble compounds, which are obtained, for example, by suitable substitution, are necessary for this purpose. These processes are also particularly suitable for oligomers, dendrimers and polymers.

Also possible are hybrid processes, in which, for example, one or more layers are applied from solution and one or more further layers are applied by vapour deposition.

These processes are generally known to the person skilled in the art and can be applied by him without inventive step to organic electroluminescent devices comprising the compounds according to the invention.

The compounds according to the invention and the organic electroluminescent devices according to the invention are distinguished by the following surprising advantages over the prior art:

1. The compounds according to the invention or compounds of the formulae (1), (2) and (16) to (82), employed as matrix material for fluorescent or phosphorescent emitters, result in very high efficiencies and long lifetimes. This applies, in particular, if the compounds are employed as matrix material for a phosphorescent emitter.
2. The compounds according to the invention or compounds of the formulae (1), (2) and (16) to (82) are suitable not only as matrix for red-phosphorescent compounds, but, in particular, also for green-phosphorescent compounds.
3. In contrast to many compounds in accordance with the prior art, which undergo partial or complete pyrolytic decomposition on sublimation, the compounds according to the invention have high thermal stability.
4. The compounds according to the invention, employed in organic electroluminescent devices, result in high efficiencies and in steep current/voltage curves with low use voltages.
5. The compounds according to the invention also result in very good properties with respect to the efficiency, lifetime and operating voltage of organic electroluminescent devices on use as electron-transport material.

These above-mentioned advantages are not accompanied by an impairment in the other electronic properties.

The invention is explained in greater detail by the following examples, without wishing to restrict it thereby. The person skilled in the art will be able to use the descriptions to carry out the invention throughout the range disclosed and to prepare further compounds according to the invention without inventive step and use them in electronic devices or use the process according to the invention.

EXAMPLES

The following syntheses are carried out under a protective-gas atmosphere, unless indicated otherwise. The starting materials can be purchased from ALDRICH or ABCR (palladium (II) acetate, tri-o-tolylphosphine, inorganics, solvents). The synthesis of 8,8-dimethylindolo[3,2,1-de]acridine and 7,7,11,11-tetramethyl-7H,11H-benz[1,8]indolo[2,3,4,5,6-de]acridine can be carried out in accordance with the literature (Chemische Berichte 1980, 113, 1, 358-84). The synthesis of 8H-indolo[3,2,1-de]phenazine (Journal of the Chemical Society 1958, 4492-4) and B[4-(1-phenyl-1H-benzimidazol-2-yl)phenyl]boronic acid (Advanced Functional Materials 2008, 18, 4, 584-590) is likewise known from the literature.

Example 1

6-Bromo-8,8-dimethyl-8H-indolo[3,2,1-de]acridine

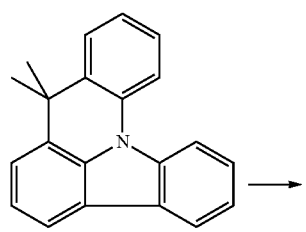

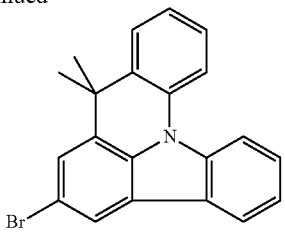

6.3 g (22.2 mmol) of 8,8-dimethylindolo[3,2,1-de]acridine are initially introduced in 150 ml of $CH_2Cl_2$. A solution of 8 g (45.1 mmol) of NBS in 100 ml of acetonitrile is subsequently added dropwise at −15° C. with exclusion of light, and the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction. Yield: 4.5 g (12 mmol), 57% of theory, purity according to $^1$H-NMR about 97%.

Example 2

2,5-Dibromo-7,7,11,11-tetramethyl-7H,11H-benz[1,8]-indolo[2,3,4,5,6-de]acridine

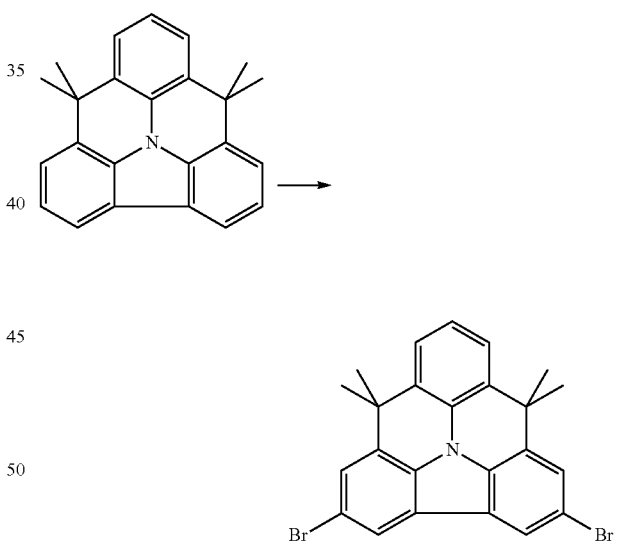

7.18 g (22.2 mmol) of 7,7,11,11-tetramethyl-7H,11H-benz[1,8]indolo-[2,3,4,5,6-de]acridine are initially introduced in 150 ml of $CH_2Cl_2$. A solution of 8 g (45.1 mmol) of NBS in 100 ml of $CH_2Cl_2$ is subsequently added drop-wise at 0° C. with exclusion of light, and the mixture is allowed to come to room temperature and is stirred at this temperature for a further 4 h. 150 ml of water are subsequently added to the mixture, which is then extracted with $CH_2Cl_2$. The organic phase is dried over $MgSO_4$, and the solvents are removed in vacuo. The product is washed by stirring with hot hexane and filtered off with suction.

Yield: 8.1 g (16 mmol), 70% of theory, purity according to $^1$H-NMR about 98%.

Example 3

8,8-Dimethyl-8H-indolo[3,2,1-de]acridine-6-boronic acid

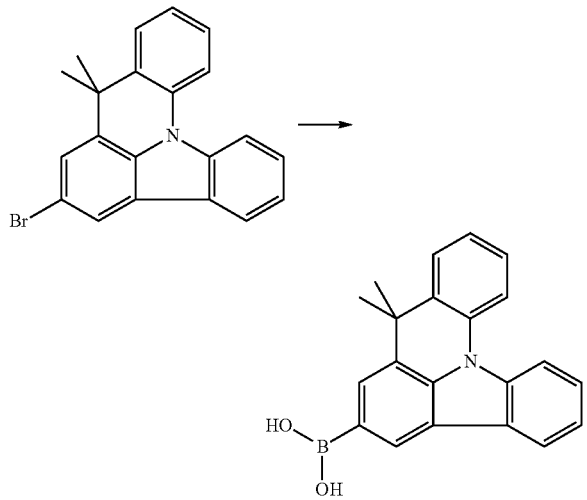

93.9 g (259 mmol) of 6-bromo-8,8-dimethyl-8H-indolo[3,2,1-de]acridine are dissolved in 1500 ml of dry THF, 135 ml (337 mmol) of a 2.5 M solution of n-butyllithium in cyclohexane are added dropwise at −70° C., after 1 h 37 ml of trimethyl borate (336 mmol) are added dropwise, the mixture is allowed to come to room temperature over the course of 1 h, the solvent is removed, and the residue, which is uniform according to ¹H-NMR, is employed in the subsequent reaction without further purification. The yield is 77 g (235 mmol), corresponding to 91% of theory.

Example 4

7,7,11,11-Tetramethyl-7H,11H-benz[1,8]indolo[2,3,4,5,6-de]acridine-2,5-bisboronic acid

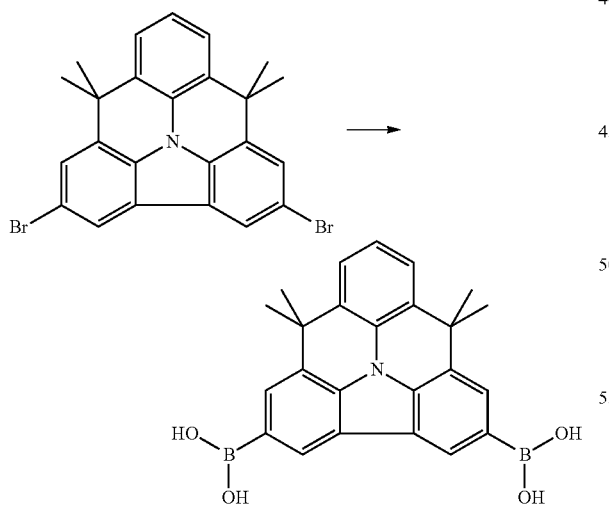

56.2 g (154 mmol) of 2,5-dibromo-7,7,11,11-tetramethyl-7H,11H-benz[1,8]-indolo[2,3,4,5,6-de]acridine are dissolved in 1400 ml of dry THF, 162 ml (404 mmol) of a 2.5 M solution of n-butyllithium in cyclohexane are added dropwise at −70° C., after 1 h 44.4 ml of trimethyl borate (403 mmol) are added dropwise, the mixture is allowed to come to RT over the course of 1 h, the solvent is removed, and the residue, which is uniform according to ¹H-NMR, is employed in the subsequent reaction without further purification. The yield is 33 g (80 mmol), corresponding to 69% of theory.

Example 5

6-(4,6-Diphenyl-1,3,5-triazin-2-yl)-8,8-dimethyl-8H-indolo[3,2,1-de]acridine

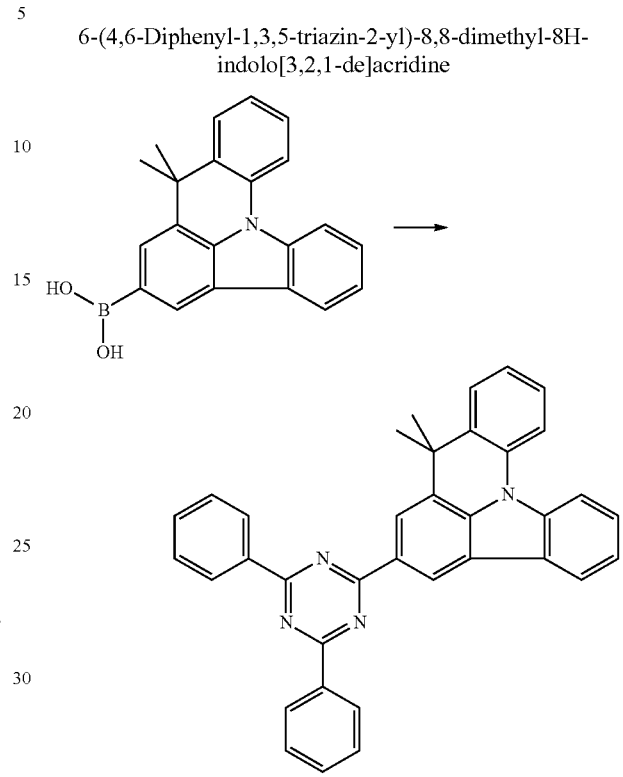

36 g (110.0 mmol) of 8,8-dimethyl-8H-indolo[3,2,1-de]acridine-6-boronic acid, 29.5 g (110.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium (II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum, the purity is 99.9%. The yield is 46 g (89 mmol), corresponding to 83% of theory.

Example 6

2,5-Bis(4,6-diphenyl-1,3,5-triazin-2-yl)-7,7,11,11-tetramethyl-7H,11H-benz[1,8]indolo[2,3,4,5,6-de]acridine

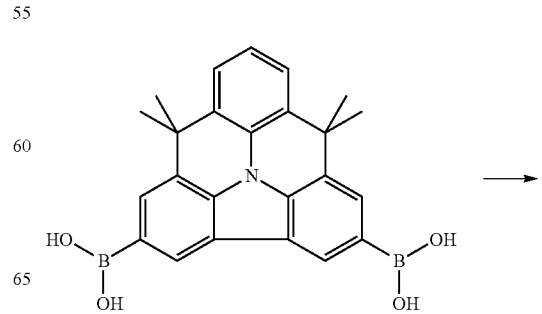

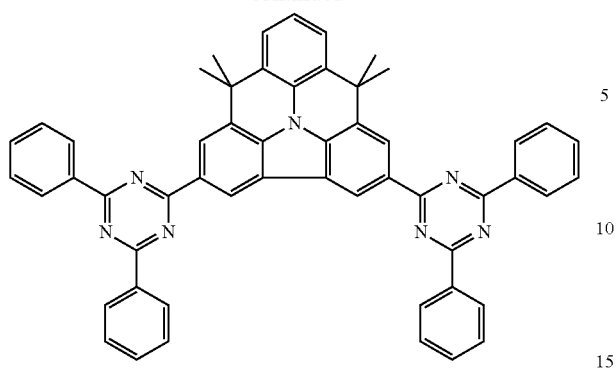

22.6 g (55 mmol) of 7,7,11,11-tetramethyl-7H,11H-benz[1,8]indolo-[2,3,4,5,6-de]acridine-2,5-bisboronic acid, 29.5 g (110.0 mmol) of 2-chloro-4,6-diphenyl-1,3,5-triazine and 44.6 g (210.0 mmol) of tripotassium phosphate are suspended in 500 ml of toluene, 500 ml of dioxane and 500 ml of water. 913 mg (3.0 mmol) of tri-o-tolylphosphine and then 112 mg (0.5 mmol) of palladium (II) acetate are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum, the purity is 99.9%. The yield is 30 g (38 mmol), corresponding to 72% of theory.

Example 7

[6-(1-Phenyl-1H-benzimidazol-2-yl)phenyl]-8,8-dimethyl-8H-indolo[3,2,1-de]acridine

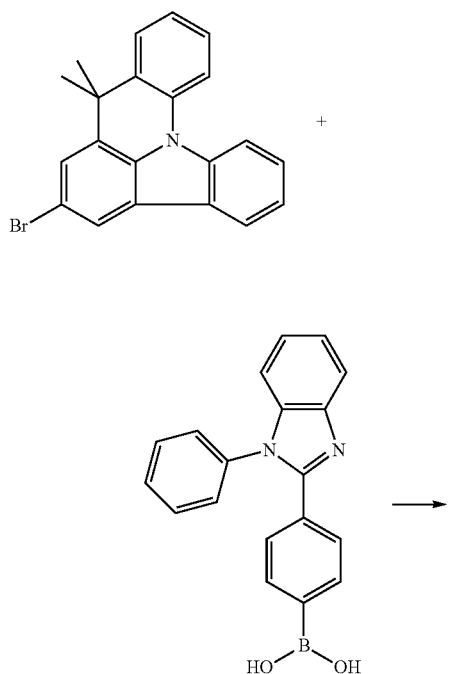

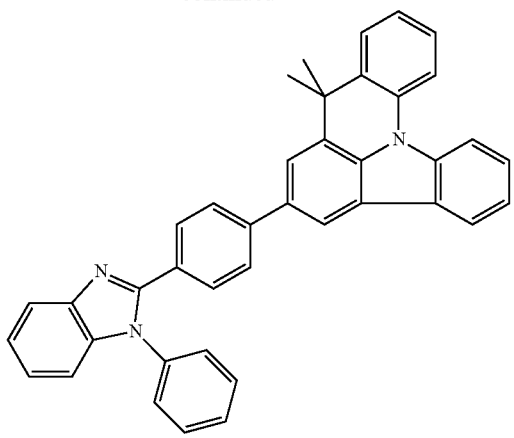

0.27 g (0.9 mmol) of tri-o-tolylphosphine and then 33.5 mg (0.15 mmol) of palladium (II) acetate are added with vigorous stirring to a degassed suspension of 10.1 g (28 mmol) of 6-bromo-8,8-dimethyl-8H-indolo[3,2,1-de]-acridine and 9.42 g (30 mmol) of benzimidazoleboronic acid and 7.8 g (31.5 mmol) of potassium phosphate hydrate in a mixture of 7.5 ml of dioxane, 15 ml of toluene and 18 ml of water. After heating under reflux for 5 h, the mixture is allowed to cool. The precipitate is filtered off with suction, washed three times with 10 ml of ethanol/water (1:1, v:v) and three times with 5 ml of ethanol, subsequently dried in vacuo and recrystallised from dioxane. Yield: 12.46 g (22.5 mmol), 81% of theory, purity according to $^1$H-NMR about 99.9%.

Example 8

3-Bromo-8,8-diphenyl-8H-indolo[3,2,1-de]acridine

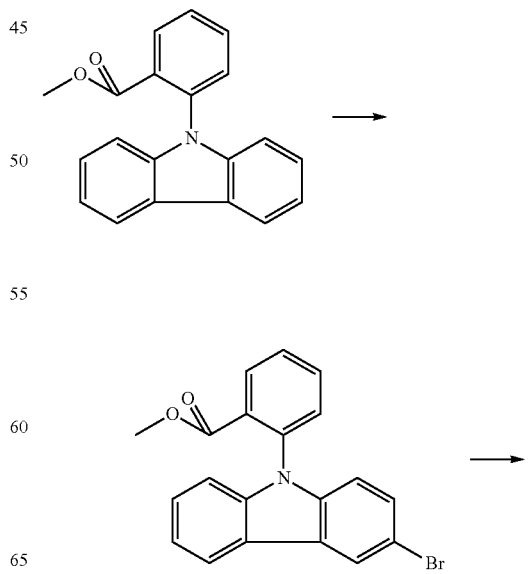

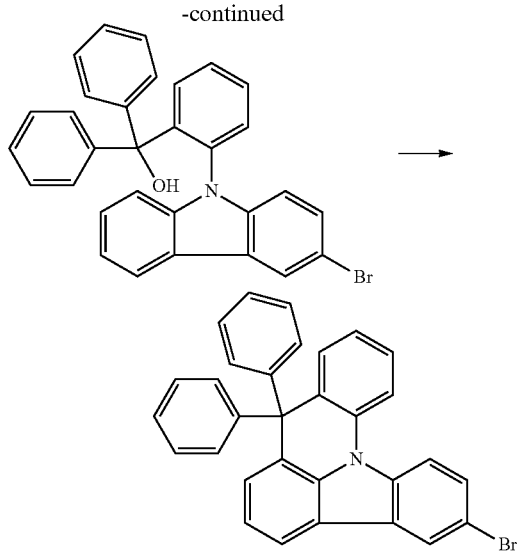

a) Methyl 2-(3-bromo-9H-carbazole)benzoate 62 g (207 mmol) of methyl 2-(9H-carbazole)benzoate are cooled to −10° C. in 2000 ml of DMF, 37.3 g (207 mmol) of NBS are added in portions, and the mixture is stirred at room temperature for 6 h. 500 ml of water are subsequently added to the mixture, which is then extracted with $CH_2Cl_2$. The organic phase is dried over $MgSO_4$, and the solvent is removed in vacuo. The product is washed by stirring with hot toluene and filtered off with suction. Yield: 72 g (190 mmol), 92% of theory, purity according to $^1$H-NMR about 98%.

b)

[2-(3-Bromocarbazol-9-yl)phenyl]diphenylmethanol 21.3 g (86.7 mmol) of cerium (III) chloride are initially introduced in 250 ml of THF. 30 g (78.9 mmol) of methyl 2-(3-bromo-9H-carbazole)benzoate, dissolved in 600 ml of dried THF, are added dropwise to this solution at room temperature, and the mixture is stirred for 2.5 h. The mixture is cooled to 0° C., 118.3 ml (236 mmol) of 2 M phenylmagnesium bromide in THF are added, and the mixture is stirred overnight. When the reaction is complete, it is carefully quenched with methanol at −30° C. The reaction solution is concentrated to a third, 1 l of $CH_2Cl_2$ is added, the mixture is washed, and the organic phase is dried over $MgSO_4$ and evaporated. Yield: 38.7 g (76.7 mmol), 97% of theory, purity according to $^1$H-NMR about 94%.

c)

3-Bromo-8,8-diphenyl-8H-indolo[3,2,1-de]acridine 38.7 g (76.7 mmol) of 2-[2-(3-bromocarbazol-9-yl)phenyl]diphenylmethanol are dissolved in 750 ml of degassed dichloromethane, a suspension of 49.6 g of polyphosphoric acid and 33 ml of methanesulfonic acid is added, and the mixture is heated at 60° C. for 1 h. The batch is cooled, and water is added. A solid precipitates out, which is dissolved in $CH_2Cl_2$/THF (1:1). The solution is carefully rendered alkaline using 20% NaOH, and the phases are separated and dried over $MgSO_4$. The solid obtained is washed by stirring with heptane. Yield: 22 g (45 mmol), 59% of theory, purity according to $^1$H-NMR about 95%.

The following compounds are obtained analogously:

| Ex. | Starting material | Product | Yield |
|---|---|---|---|
| 9 | | | 63% |
| 10 | | | 71% |
| 11 | | | 59% |

| Ex. | Starting material | Product | Yield |
|---|---|---|---|
| 12 | | | 56% |

Example 13

8,8-Diphenyl-8H-indolo[3,2,1-de]acridine-6-boronic acid

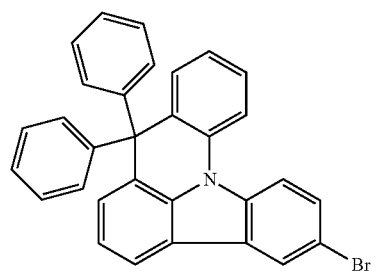
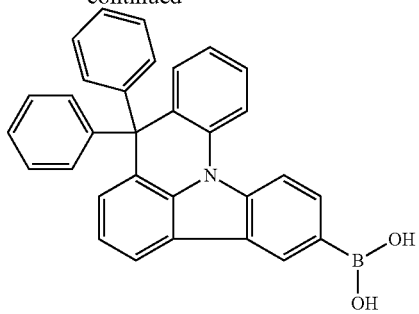

125.9 g (259 mmol) of bromo-8,8-diphenyl-8H-indolo[3,2,1-de]acridine are dissolved in 1500 ml of dry THF, 135 ml (337 mmol) of a 2.5 M solution of n-butyllithium in cyclohexane are added dropwise at −70° C., after 1 h 37 ml of trimethyl borate (336 mmol) are added dropwise, the mixture is warmed to room temperature over the course of 1 h, the solvent is removed, and the residue, which is uniform according to ¹H-NMR, is employed in the subsequent reaction without further purification.

Yield: 87.6 g (194 mmol), 75% of theory, purity according to ¹H-NMR about 96%.

The following compounds are obtained analogously:

| Ex. | Starting material | Product | Yield |
|---|---|---|---|
| 14 | (J. Mater. Chem. 2009, 19, 7661-7665) | | 61% |

| Ex. | Starting material | Product | Yield |
|---|---|---|---|
| 15 | | | 55% |

Example 16

6-(4,6-Diphenyl-1,3,5-triazin-2-yl)-8,8-diphenyl-8H-indolo[3,2,1-de]acridine

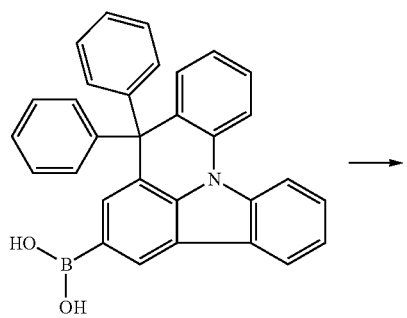

→

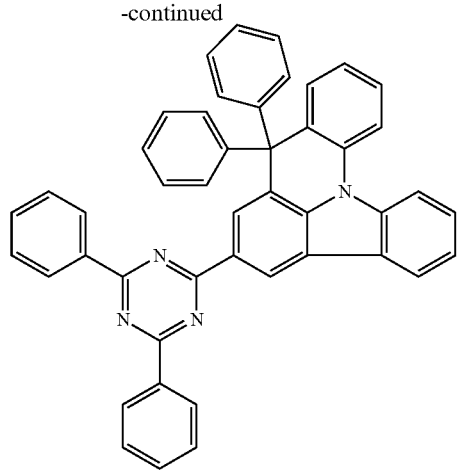

20 g (44 mmol) of 8,8-diphenyl-8H-indolo[3,2,1-de]acridine-6-boronic acid, 11.7 g (44 mmol) of 2-chloro-4,6-diphenyl-1,3,5-triazine and 2.9 g (27.4 mmol) of sodium carbonate are suspended in 70 ml of toluene, 70 ml of dioxane and 50 ml of water. 1.44 mg (1.24 mmol) of Pd(PPh$_3$)$_4$ are added to this suspension, and the reaction mixture is heated under reflux for 16 h. After cooling, the organic phase is separated off, filtered through silica gel, washed three times with 200 ml of water and subsequently evaporated to dryness. The residue is recrystallised from toluene and from dichloromethane/isopropanol and finally sublimed in a high vacuum, the purity is 99.9%. The yield is 22.4 g (35 mmol), corresponding to 80% of theory.

The following compounds are obtained analogously:

| Ex. | Starting material 1 | Starting material 2 | Product | Yield |
|---|---|---|---|---|
| 17 | | | | 67% |

-continued
| Ex. | Starting material 1 | Starting material 2 | Product | Yield |
|---|---|---|---|---|
| 18 | | | | 72% |
| 19 | | | | 61% |
| 20 | | | | 66% |
Example 21
8,8-Diphenyl-6-[4-(1-phenyl-1H-benzoimidazol-2-yl)-phenyl]-8H-indolo[3,2,1-de]acridine
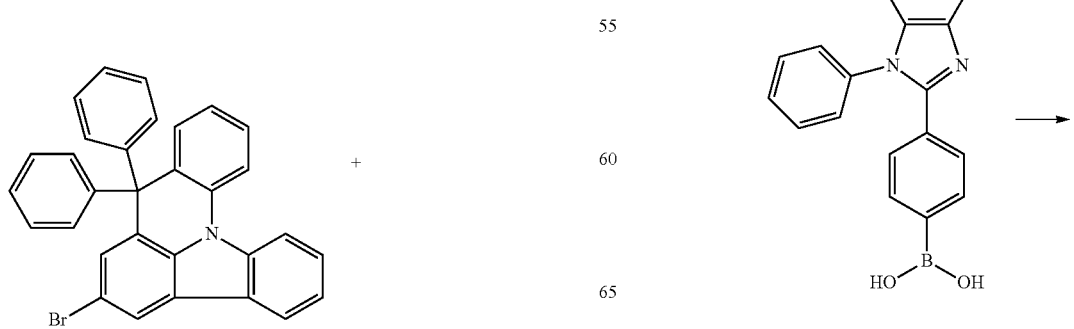
-continued -continued

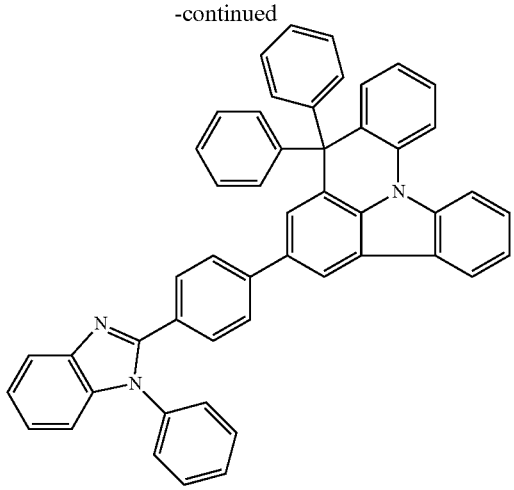

0.27 g (0.9 mmol) of tri-o-tolylphosphine and then 33.5 mg (0.15 mmol) of palladium (II) acetate are added with vigorous stirring to a degassed suspension of 13.6 g (28 mmol) of 3-bromo-8,8-diphenyl-8H-indolo[3,2,1-de]-acridine, 9.42 g (30 mmol) of benzimidazoleboronic acid and 7.8 g (31.5 mmol) of potassium phosphate hydrate in a mixture of 7.5 ml of dioxane, 15 ml of toluene and 18 ml of water. After heating under reflux for 5 h, the mixture is allowed to cool. The precipitate is filtered off with suction, washed three times with 10 ml of ethanol/water (1:1, v:v) and three times with 5 ml of ethanol, subsequently dried in vacuo and recrystallised from dioxane. Yield: 16 g (23 mmol), 85% of theory, purity according to $^1$H-NMR about 99.9%.

The following compounds are obtained analogously:

| Ex. | Starting material | Product | Yield |
|---|---|---|---|
| 22 | J. Mater. Chem. 2009, 19, 7661-7665 | | 73% |
| 23 | | | 65% |

Example 24

(8,8-Diphenyl-8H-indolo[3,2,1-de]acridin-3-yl)phenyl-methanone

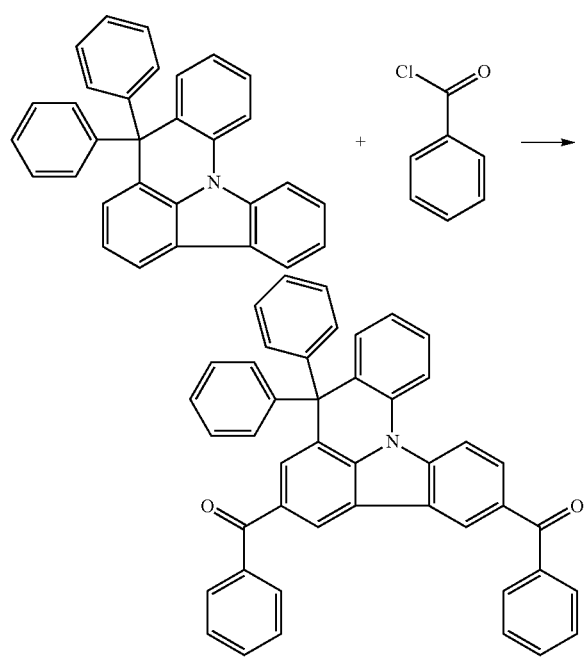

A degassed solution of 6.1 g (18 mmol) of 8,8-diphenyl-8H-indolo-[3,2,1-de]acridine in 40 ml of chloroform is cooled to 0° C., and 5 g (37 mmol) of AlCl$_3$ are added. 3.9 g of benzoyl chloride are then added dropwise at this temperature, and the mixture is stirred for 8 h. 50 ml of water are added to the mixture, and the organic phase is separated off, filtered through silica gel and evaporated to dryness. The residue is recrystallised from toluene and from dichloromethane/isopropanol and finally sublimed in a high vacuum, the purity is 99.9%. The yield is 13.7 g (27 mmol), corresponding to 90% of theory.

The following compounds are obtained analogously:

Example 27

Bis-(8,8-dimethyl-8H-indolo[3,2,1-d,e]acridin-3-yl)-methanone

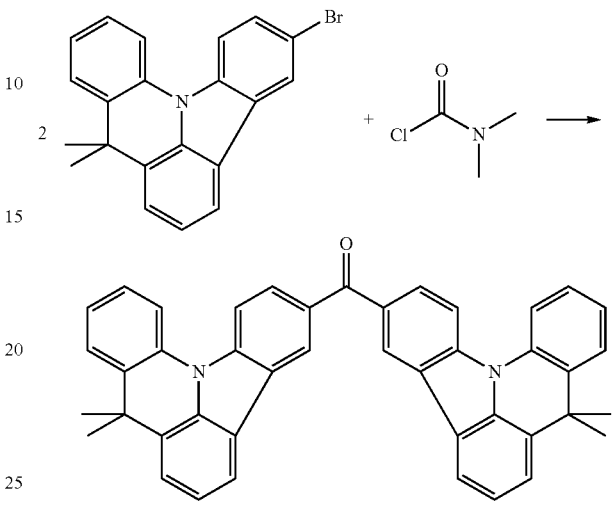

n-Butyllithium (26.6 ml of a 2.0 N solution in hexane) is added at −78° C. to a solution of 3-bromo-8,8-dimethyl-8H-indolo[3,2,1-de]acridine (15.4 g, 43 mmol) in THF (250 ml), the mixture is stirred at this temperature for 1 h, and a solution of dimethylcarbamoyl chloride (2.0 ml, 21 mmol) in THF (2 ml) is added. After stirring at −78° C. for a further 2 h, the reaction mixture is slowly warmed to room temperature and added to ice-water. The resultant precipitate is separated off by filtration and purified by repeated recrystallisation from dioxane. Final sublimation in a high vacuum (T=350° C., p=7×10$^{-5}$ mbar) gives the product in a purity of 99.9% (5.2 g, 20%).

Example 28

Production of OLEDs

OLEDs according to the invention and OLEDs in accordance with the prior art are produced by a general process in

| Ex. | Starting material 1 | Starting material 2 | Product | Yield |
|---|---|---|---|---|
| 25 | | | | 72% |
| 26 | | | | 83% | accordance with WO 04/058911, which is adapted to the circumstances described here (layer-thickness variation, materials used).

The results for various OLEDs are presented in the following Examples 29 to 55 (see Tables 1 to 3). Glass plates coated with structured ITO (indium tin oxide) in a thickness of 150 nm are coated with 20 nm of PEDOT (poly-(3,4-ethylenedioxy-2,5-thiophene), spin-coated from water; purchased from H. C. Starck, Goslar, Germany) for improved processing. These coated glass plates form the substrates to which the OLEDs are applied. The OLEDs have in principle the following layer structure: substrate/hole-transport layer (HTL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials used for the production of the OLEDs are shown in Table 2.

All materials are applied by thermal vapour deposition in a vacuum chamber. The emission layer here always consists of at least one matrix material (host material) and an emitting dopant (emitter), which is admixed with the matrix material or materials in a certain proportion by volume by co-evaporation. Information such as H3:CBP:TER1 (55%:35%:10%) here means that material H3 is present in the layer in a proportion by volume of 55%, CBP is present in a proportion of 35% and TER1 is present in a proportion of 10%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminance characteristic lines (IUL characteristic lines), and the lifetime are determined. The lifetime is defined as the time after which the luminous density has dropped from a certain initial luminous density to a certain proportion. LD80 means that the said lifetime is the time by which the luminous density has dropped to 80% of the initial luminous density, i.e. from, for example, 4000 cd/m$^2$ to 3200 cd/m$^2$.

Some of the examples are explained in greater detail below in order to illustrate the advantages of the compounds according to the invention. However, it should be pointed out that this only represents a selection of the data shown in Table 3. As is evident from the table, improvements over the prior art are also achieved on use of the compounds according to the invention which are not mentioned in greater detail, in some cases in all parameters, in some cases only an improvement in the efficiency or voltage or lifetime is observed. However, the improvement in just one of the said parameters represents a significant advance since different applications require optimisation with respect to different parameters.

Use of Compounds According to the Invention as Matrix Materials in Phosphorescent OLEDs The compounds according to the invention can be employed, inter alia, as matrix materials (host materials) for phosphorescent dopants. Compounds H2 and H3 are used here. Compounds H1 and H4 are used as comparison in accordance with the prior art. OLEDs comprising the green-emitting dopant TEG1 and the red-emitting dopant TER1 are shown. The results for the OLEDs are shown in Table 3. Ex. 29 to 32A show OLEDs comprising materials in accordance with the prior art and serve as comparative examples.

The advantages on use of compounds according to the invention as matrix materials for red- and green-emitting OLEDs are an increase in the lifetime at the same time as a reduction in the operating voltage and a consequent significant increase in the power efficiency (see Ex. 33-38). Thus, a 55% longer lifetime compared with the prior art H1 is obtained on use of H3, with the power efficiency likewise improving very significantly, namely by about 40% (cf. Ex. 38 and 32). On use of H2 in green-emitting OLEDs, the improvement in these parameters is likewise very significant, but is somewhat less than in the case of H3. Compared with the prior art H4, the compounds according to the invention exhibit even greater improvements with respect to efficiency, voltage and lifetime.

In the case of red emission, H2 exhibits somewhat better characteristic data than H3, with the power efficiency here increasing by up to 30%, and the lifetime being improved by about 35% compared with the prior art (cf. Ex. 35 and 30).

In particular, compounds which are substituted by phenyl rings on the bridge Y also exhibit good performance data. Thus, for example, H5 exhibits a better lifetime compared with H3 with virtually identical power efficiency (Examples 41 and 47). The same applies to the comparison of H2 with H9 (Examples 35 and 36).

Use of Compounds According to the Invention as Electron-Transport Materials

The compounds according to the invention can furthermore be employed as electron-transport materials. Compound ETM2 is used here. Compound Alq$_3$ and ETM1 are used as comparison in accordance with the prior art. Ex. 29 to 32A show OLEDs comprising materials in accordance with the prior art and serve as comparative examples. Compared with the prior art, the compounds according to the invention are distinguished by improved efficiency and a lower operating voltage on use as electron-transport materials.

If an electron-injection layer consisting of LiF is used, a current efficiency which is improved by about 10%, but in particular a power efficiency which is improved by about 30% owing to the lower operating voltage (cf. Ex. 29 and 39), is obtained on use of ETM2 compared with Alq$_3$. If a mixture of ETM2 and LiQ is employed as electron-transport layer (Ex. 40), the current efficiency can be increased from 54 cd/A to 61 cd/A. Together with the somewhat lower operating voltage, a significant increase in the power efficiency by about 20% is thus obtained through the use of compound ETM2 according to the invention (cf. Ex. 40 with Ex. 32). In both cases (Ex. 39 and 40), the lifetime of the components is slightly longer on use of ETM2 than on use of the electron-transport materials in accordance with the prior art. If compound H11 containing phenyl rings on the bridge is used as ETM and compared with compound ETM2 containing methyl groups on the bridge, it can be seen that the lifetime can be slightly improved, while the other performance data remain approximately the same (Examples 55 and 40).

TABLE 1

| | | | Structure of the OLEDs | | | |
|---|---|---|---|---|---|---|
| Ex. | HTL thickness | EBL thickness | EML thickness | HBL thickness | ETL thickness | EIL thickness |
| 29 (comp.) | HTM1 20 nm | NPB 20 nm | H1:TER1 (85%:15%) 30 nm | — | Alq$_3$ 20 nm | LiF 1 nm |

TABLE 1-continued

| | | | Structure of the OLEDs | | | |
|---|---|---|---|---|---|---|
| Ex. | HTL thickness | EBL thickness | EML thickness | HBL thickness | ETL thickness | EIL thickness |
| 30 (comp.) | HTM1 20 nm | NPB 20 nm | H1:CBP:TER1 (45%:45%:10%) 30 nm | H1 10 nm | Alq$_3$ 20 nm | LiF 1 nm |
| 31 (comp.) | HTM1 160 nm | EBM1 20 nm | H1:TEG1 (90%:10%) 30 nm | H1 10 nm | ETM1:LiQ (50%:50%) 40 nm | — |
| 32 (comp.) | HTM1 160 nm | EBM1 20 nm | H1:TEG1 (90%:10%) 30 nm | — | ETM1:LiQ (50%:50%) 40 nm | — |
| 32A (comp.) | HTM1 160 nm | EBM1 20 nm | H4:TEG1 (90%:10%) 30 nm | — | ETM1:LiQ (50%:50%) 40 nm | — |
| 33 | HTM1 20 nm | NPB 20 nm | H2:TER1 (85%:15%) 30 nm | — | Alq$_3$ 20 nm | LiF 1 nm |
| 34 | HTM1 20 nm | NPB 20 nm | H3:TER1 (85%:15%) 30 nm | — | Alq$_3$ 20 nm | LiF 1 nm |
| 35 | HTM1 20 nm | NPB 20 nm | H2:CBP:TER1 (45%:45%:10%) 30 nm | H1 10 nm | Alq$_3$ 20 nm | LiF 1 nm |
| 36 | HTM1 160 nm | EBM1 20 nm | H2:TEG1 (90%:10%) 30 nm | H1 10 nm | ETM1:LiQ (50%:50%) 40 nm | — |
| 37 | HTM1 160 nm | EBM1 20 nm | H3:TEG1 (90%:10%) 30 nm | H1 10 nm | ETM1:LiQ (50%:50%) 40 nm | — |
| 38 | HTM1 160 nm | EBM1 20 nm | H3:TEG1 (90%:10%) 30 nm | — | ETM1:LiQ (50%:50%) 40 nm | — |
| 39 | HTM1 20 nm | NPB 20 nm | H1:TER1 (85%:15%) 30 nm | — | ETM2 20 nm | LiF 1 nm |
| 40 | HTM1 160 nm | EBM1 20 nm | H1:TEG1 (90%:10%) 30 nm | — | ETM2:LiQ (50%:50%) 40 nm | — |
| 41 | HTM1 160 nm | EBM1 20 nm | H5:TEG1 (90%:10%) 30 nm | H1 10 nm | ETM1:LiQ (50%:50%) 40 nm | — |
| 42 | HTM1 160 nm | EBM1 20 nm | H6:TEG1 (90%:10%) 30 nm | H1 10 nm | ETM1:LiQ (50%:50%) 40 nm | — |
| 43 | HTM1 20 nm | NPB 20 nm | H7:TER1 (85%:15%) 30 nm | — | Alq$_3$ 20 nm | LiF 1 nm |
| 44 | HTM1 20 nm | NPB 20 nm | H8:TER1 (85%:15%) 30 nm | — | Alq$_3$ 20 nm | LiF 1 nm |
| 45 | HTM1 160 nm | EBM1 20 nm | H9:TEG1 (90%:10%) 30 nm | H1 10 nm | ETM1:LiQ (50%:50%) 40 nm | — |
| 46 | HTM1 160 nm | EBM1 20 nm | H10:TEG1 (90%:10%) 30 nm | H1 10 nm | ETM1:LiQ (50%:50%) 40 nm | — |
| 47 | HTM1 160 nm | EBM1 20 nm | H11:TEG1 (90%:10%) 30 nm | H1 10 nm | ETM1:LiQ (50%:50%) 40 nm | — |
| 48 | HTM1 160 nm | EBM1 20 nm | H12:TEG1 (90%:10%) 30 nm | H1 10 nm | ETM1:LiQ (50%:50%) 40 nm | — |
| 49 | HTM1 160 nm | EBM1 20 nm | H13:TEG1 (90%:10%) 30 nm | H1 10 nm | ETM1:LiQ (50%:50%) 40 nm | — |
| 50 | HTM1 160 nm | EBM1 20 nm | H14:TEG1 (90%:10%) 30 nm | H1 10 nm | ETM1:LiQ (50%:50%) 40 nm | — |
| 51 | HTM1 20 nm | NPB 20 nm | H15:TER1 (85%:15%) 30 nm | — | Alq$_3$ 20 nm | LiF 1 nm |
| 52 | HTM1 160 nm | EBM1 20 nm | H16:TEG1 (90%:10%) 30 nm | H1 10 nm | ETM1:LiQ (50%:50%) 40 nm | — |
| 53 | HTM1 160 nm | EBM1 20 nm | H14:IC1:TEG1 (30%:60%:10%) 30 nm | H1 10 nm | ETM1:LiQ (50%:50%) 40 nm | — |

TABLE 1-continued
Structure of the OLEDs
| Ex. | HTL thickness | EBL thickness | EML thickness | HBL thickness | ETL thickness | EIL thickness |
|---|---|---|---|---|---|---|
| 54 | HTM1 160 nm | EBM1 20 nm | H16:IC1:TEG1 (30%:60%:10%) 30 nm | H1 10 nm | ETM1:LiQ (50%:50%) 40 nm | — |
| 55 | HTM1 160 nm | EBM1 20 nm | H1:TEG1 (90%:10%) 30 nm | — | H11:LiQ (50%:50%) 30 nm | — |
TABLE 2
Structural formulae of the materials used
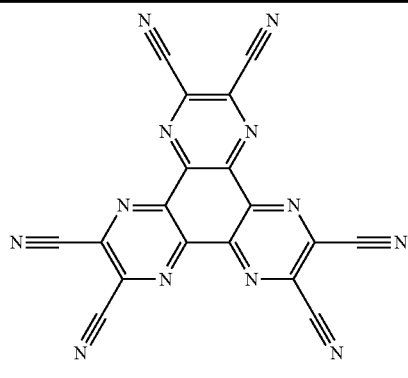
HIL1
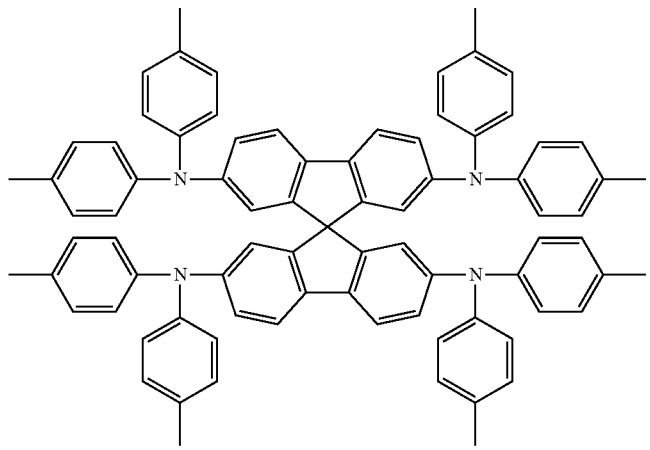
HTM1
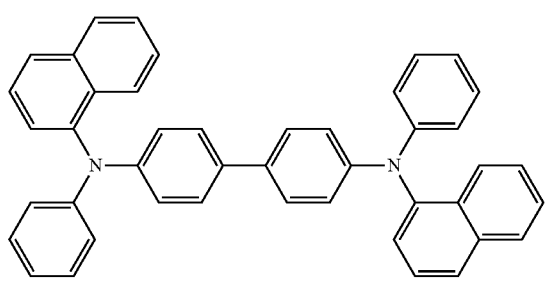
NPB TABLE 2-continued
Structural formulae of the materials used
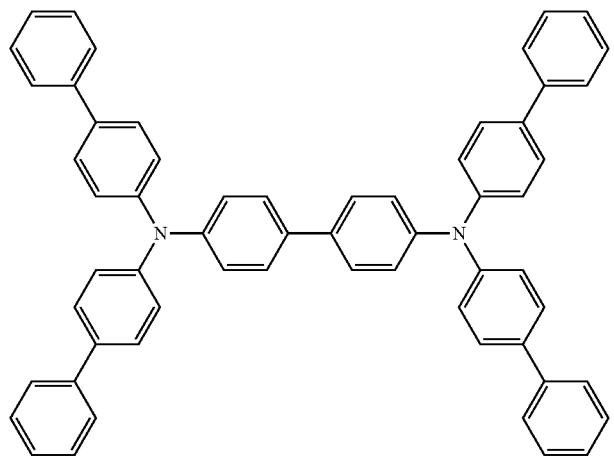
EBM1
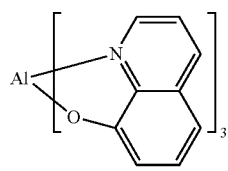
Alq₃
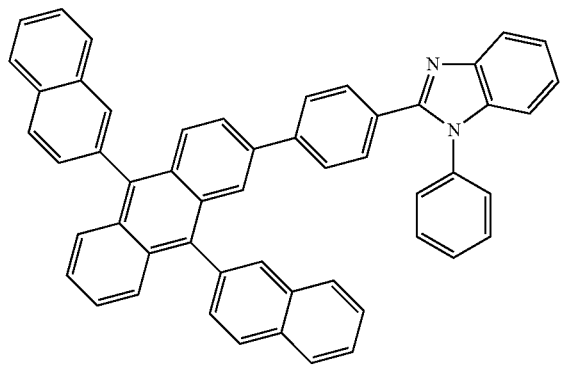
ETM1
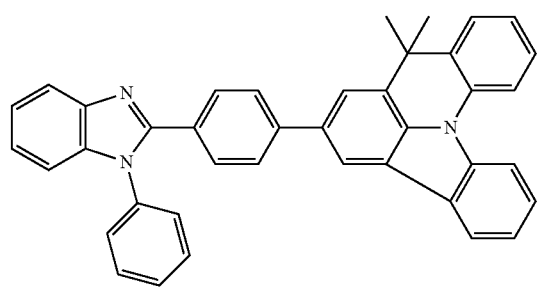
ETM2

TABLE 2-continued
Structural formulae of the materials used
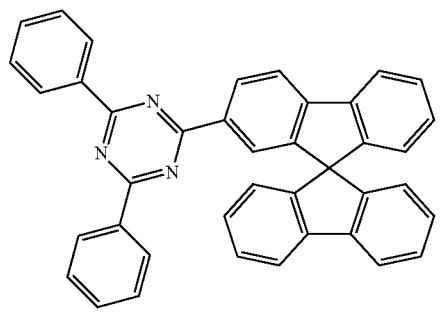
H1
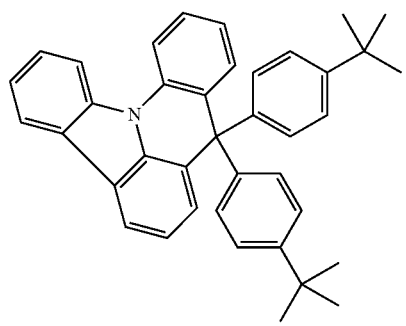
H4
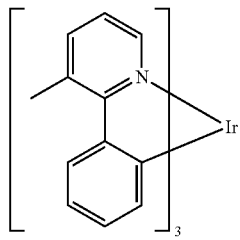
TEG1
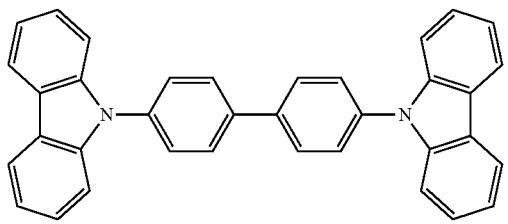
CBP
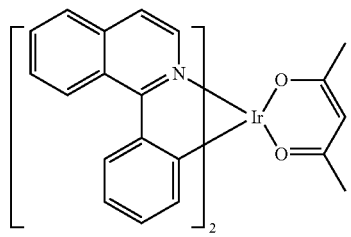
TER1

TABLE 2-continued
Structural formulae of the materials used
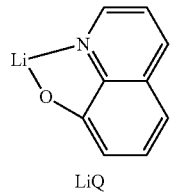
LiQ
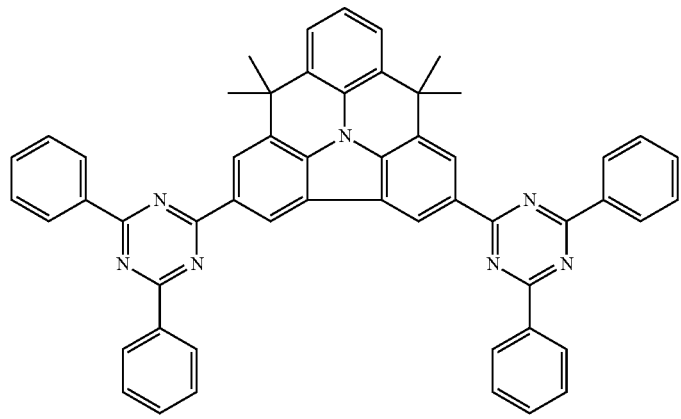
H2
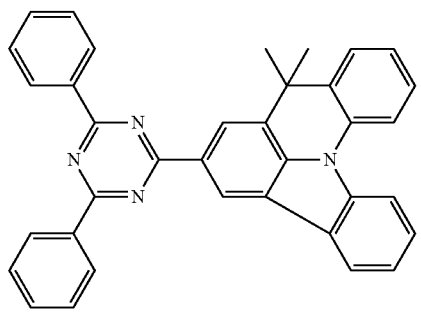
H3
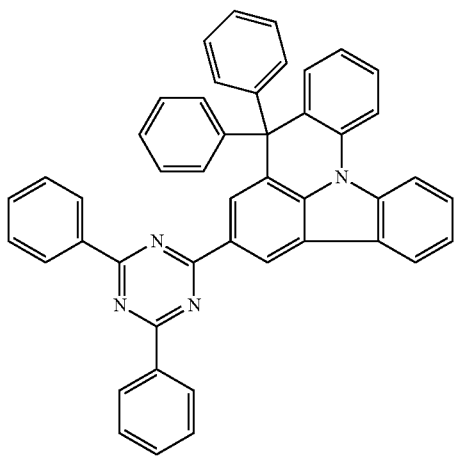
H5

TABLE 2-continued
Structural formulae of the materials used
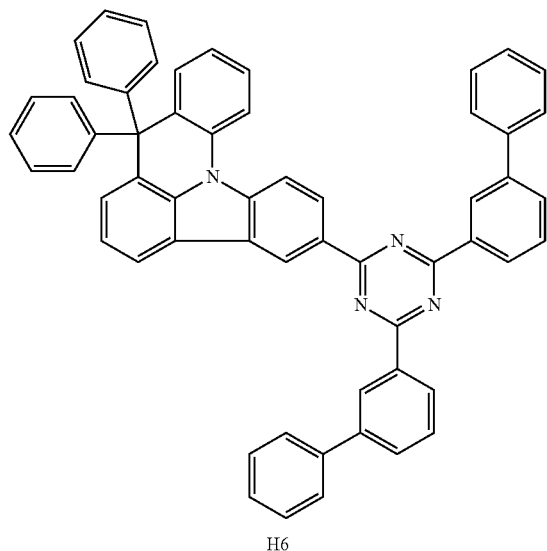
H6
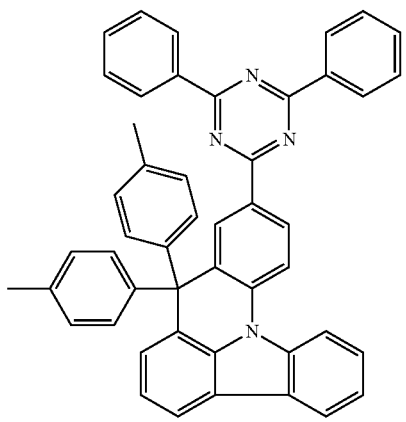
H7
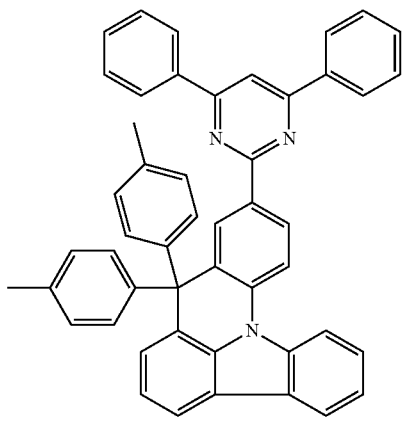 [SMILES: Cc1ccc(C2(c3ccc(C)cc3)c3cc(-c4nc(-c5ccccc5)cc(-c5ccccc5)n4)ccc3-n3c4ccccc4c4cccc2c43)cc1]
H8

TABLE 2-continued
Structural formulae of the materials used
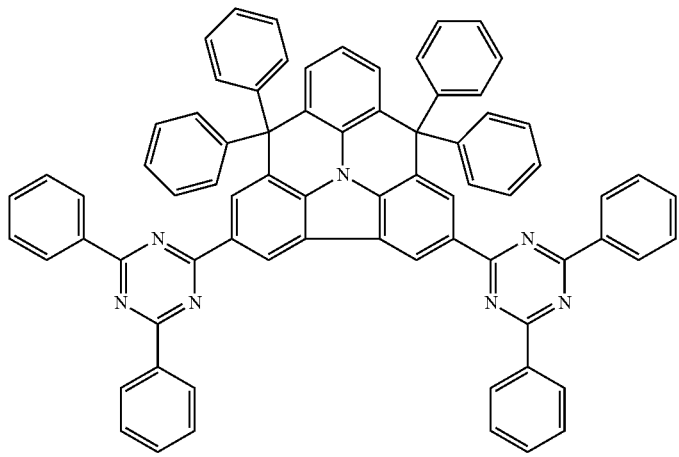 [SMILES: c1ccc(-c2nc(-c3ccccc3)nc(-c3cc4c5c(c3)c3cc(-c6nc(-c7ccccc7)nc(-c7ccccc7)n6)cc6c3n5-c3c(cccc3C6(c3ccccc3)c3ccccc3)C4(c3ccccc3)c3ccccc3)n2)cc1]
H9
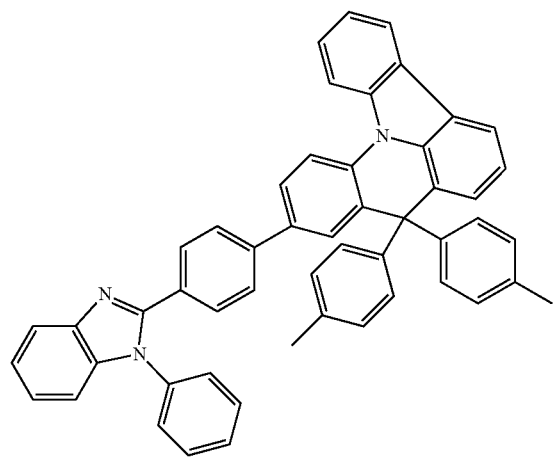
H10
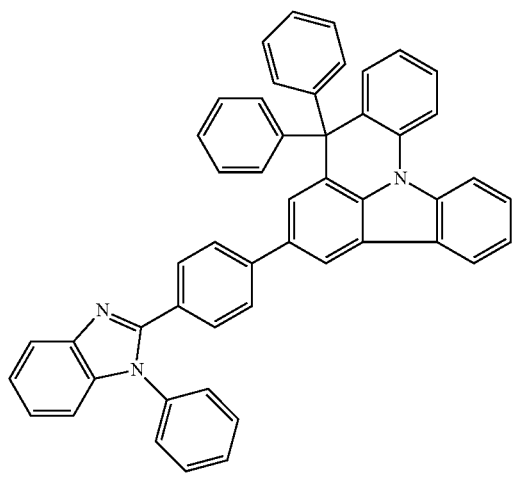
H11

TABLE 2-continued
Structural formulae of the materials used
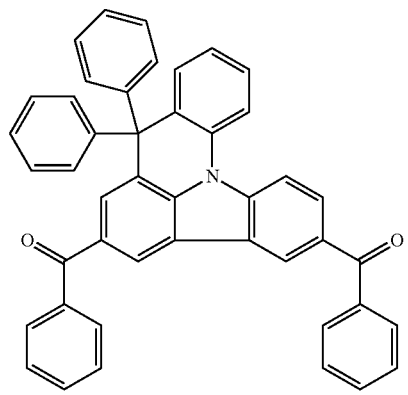
H12
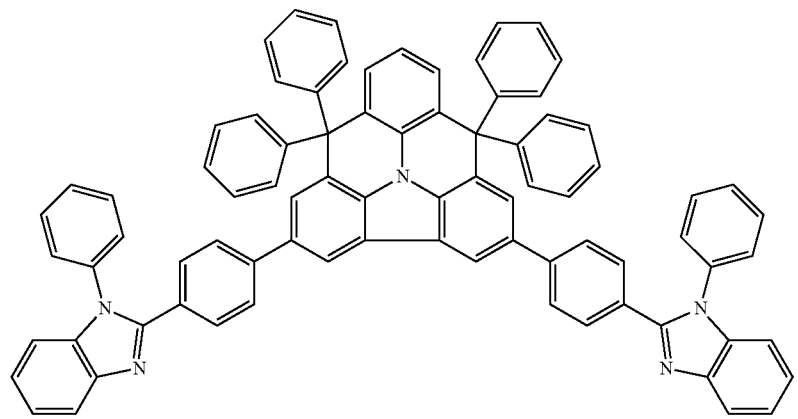 [SMILES: c1ccc(-n2c(-c3ccc(-c4cc5c6c(c4)c4cc(-c7ccc(-c8nc9ccccc9n8-c8ccccc8)cc7)cc7c4n6-c4c(cccc4C7(c4ccccc4)c4ccccc4)C5(c4ccccc4)c4ccccc4)cc3)nc3ccccc32)cc1]
H13
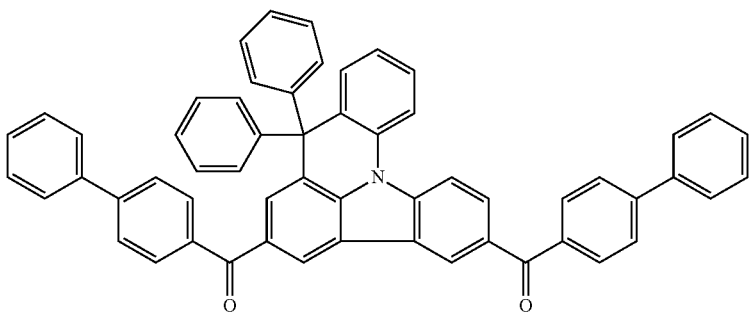
H14
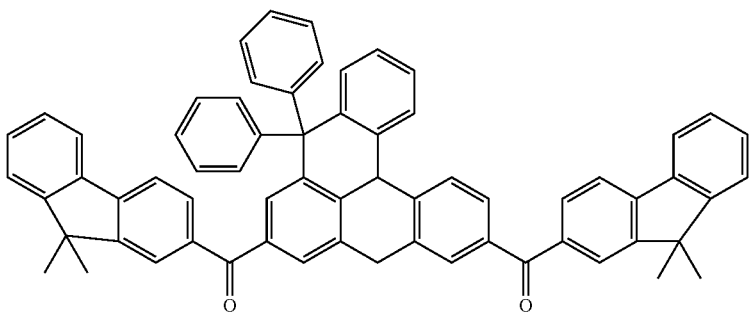
H15

TABLE 2-continued

Structural formulae of the materials used

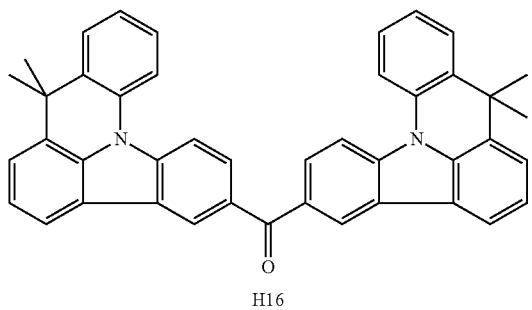

H16

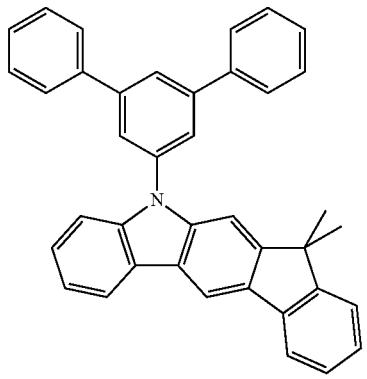

IC1

TABLE 3

Use of compounds according to the invention as matrix materials and ETM in phosphorescent OLEDs

| Ex. | Voltage for 1000 cd/m² | Efficiency at 1000 cd/m² | Efficiency at 1000 cd/m² | CIE x/y at 1000 cd/m² | LD80 from 4000 cd/m² |
|---|---|---|---|---|---|
| 29 (comp.) | 5.0 V | 7.2 cd/A | 4.5 lm/W | 0.69/0.31 | 230 h |
| 30 (comp.) | 5.2 V | 8.1 cd/A | 4.9 lm/W | 0.68/0.32 | 250 h |
| 31 (comp.) | 4.7 V | 55 cd/A | 37 lm/W | 0.36/0.61 | 440 h |
| 32 (comp.) | 4.6 V | 54 cd/A | 37 lm/W | 0.37/0.60 | 400 h |
| 32A (comp.) | 4.9 V | 46 cd/A | 30 lm/W | 0.37/0.60 | 270 h |
| 33 | 4.6 V | 8.4 cd/A | 5.7 lm/W | 0.69/0.31 | 310 h |
| 34 | 4.6 V | 8.2 cd/A | 5.6 lm/W | 0.68/0.31 | 330 h |
| 35 | 4.8 V | 9.8 cd/A | 6.4 lm/W | 0.69/0.32 | 340 h |
| 36 | 3.7 V | 59 cd/A | 50 lm/W | 0.36/0.60 | 590 h |
| 37 | 3.6 V | 58 cd/A | 51 lm/W | 0.36/0.61 | 670 h |
| 38 | 3.4 V | 55 cd/A | 51 lm/W | 0.36/0.61 | 620 h |
| 39 | 4.3 V | 7.9 cd/A | 5.8 lm/W | 0.69/0.32 | 250 h |
| 40 | 4.3 V | 61 cd/A | 45 lm/W | 0.37/0.61 | 410 h |
| 41 | 3.5 V | 56 cd/A | 50 lm/W | 0.36/0.61 | 740 h |
| 42 | 3.8 V | 52 cd/A | 44 lm/W | 0.36/0.60 | 710 h |
| 43 | 4.7 V | 8.5 cd/A | 5.7 lm/W | 0.69/0.31 | 290 h |
| 44 | 4.4 V | 7.8 cd/A | 5.5 lm/W | 0.69/0.31 | 360 h |
| 45 | 3.7 V | 58 cd/A | 49 lm/W | 0.36/0.61 | 660 h |
| 46 | 4.4 V | 52 cd/A | 37 lm/W | 0.36/0.61 | 510 h |
| 47 | 4.5 V | 49 cd/A | 34 lm/W | 0.36/0.60 | 480 h |
| 48 | 4.0 V | 57 cd/A | 44 lm/W | 0.36/0.60 | 530 h |
| 49 | 4.6 V | 47 cd/A | 32 lm/W | 0.36/0.60 | 420 h |
| 50 | 3.9 V | 55 cd/A | 44 lm/W | 0.36/0.61 | 620 h |
| 51 | 4.8 V | 7.9 cd/A | 5.2 lm/W | 0.69/0.31 | 380 h |
| 52 | 3.4 V | 57 cd/A | 53 lm/W | 0.36/0.60 | 640 h |
| 53 | 4.1 V | 53 cd/A | 41 lm/W | 0.36/0.61 | 700 h |
| 54 | 3.5 V | 53 cd/A | 47 lm/W | 0.36/0.61 | 730 h |
| 55 | 4.3 V | 63 cd/A | 45 lm/W | 0.36/0.61 | 450 h |

The invention claimed is:

1. A compound of the formula (1) or formula (2):

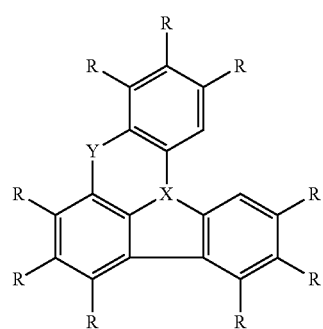

formula (1)

-continued

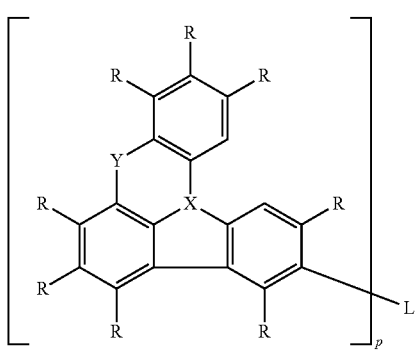

formula (2)

where the following applies to the symbols and indices used:

X is, on each occurrence, N;

Y is, on each occurrence, identically or differently, $C(R)_2$, $C=O$, $C=S$, $C=NR$ or $C=C(R)_2$;

R is on each occurrence, identically or differently, H, D, F, Cl, Br, I, CN, $NO_2$, $N(Ar)_2$, $N(R^1)_2$, $C(=O)Ar$, $C(=O)R^1$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^1$, where one or more non-adjacent $CH_2$ groups is optionally replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more H atoms is optionally replaced by D, F, Cl, Br, I, CN or $NO_2$, an aromatic or heteroaromatic ring system having 5 to 80 aromatic ring atoms, which optionally in each case is substituted by one or more radicals $R^1$, an aryloxy or heteroaryloxy group having 5 to 60 aromatic ring atoms, which is optionally substituted by one or more radicals $R^1$, or a combination of these systems, where two or more adjacent substituents R may optionally form a monocyclic or polycyclic, aliphatic, aromatic or heteroaromatic ring system, which is optionally substituted by one or more radicals $R^1$;

$R^1$ is on each occurrence, identically or differently, a H, D, F, Cl, Br, I, CN, $NO_2$, $N(Ar)_2$, $N(R^2)_2$, $C(=O)Ar$, $C(=O)R^2$, $P(=O)(Ar)_2$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals $R^2$, where one or more non-adjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more H atoms is optionally replaced by D, F, Cl, Br, I, CN or $NO_2$, an aromatic or heteroaromatic ring system having 5 to 80 aromatic ring atoms, which may in each case be substituted by one or more radicals $R^2$, an aryloxy or heteroaryloxy group having 5 to 60 aromatic ring atoms, which is optionally substituted by one or more radicals $R^2$, or a combination of these systems, where two or more adjacent substituents R may optionally form a monocyclic or polycyclic, aliphatic, aromatic or heteroaromatic ring system, which is optionally substituted by one or more radicals $R^2$;

$R^2$ is a H, D, F, CN, an aliphatic hydrocarbon radical having 1 to 20 C atoms, an aromatic or heteroaromatic ring system having 5 to 30 aromatic ring atoms, in which one or more H atoms is optionally replaced by D, F, Cl, Br, I or CN, where two or more adjacent substituents $R^2$ may form a mono- or polycyclic, aliphatic, aromatic or heteroaromatic ring system with one another;

Ar is on each occurrence, identically or differently, an aromatic or heteroaromatic ring system having 5-30 aromatic ring atoms, which is optionally substituted by one or more non-aromatic radicals $R^2$; two radicals Ar which are bonded to the same N atom or P atom here may also be bridged to one another by a single bond or a bridge selected from $N(R^2)$, $C(R^2)_2$ or O;

L is a divalent or polyvalent straight-chain alkylene, alkylidene, alkyleneoxy or thioalkyleneoxy group having 1 to 40 C atoms or a branched or cyclic alkylene, alkylidene, alkyleneoxy or thioalkyleneoxy group having 3 to 40 C atoms or an alkenylene or alkynylene group having 2 to 40 C atoms, which is optionally substituted by in each case one or more radicals $R^1$, where one or more non-adjacent $CH_2$ groups is optionally replaced by $-R^1C=CR^1-$, $-C\equiv C-$, $Si(R^1)_2$, $Ge(R^1)_2$, $Sn(R^1)_2$, $C=O$, $C=S$, $C=Se$, $C=NR^1$, $P(=O)R^1$, $S=O$, $SO_2$, $-O-$, $-S-$ or $-CONR^1-$ and where one or more H atoms is optionally replaced by D, F, Cl, Br, I, CN or $NO_2$, or an at least divalent aromatic or heteroaromatic ring system having 5 to 80 aromatic ring atoms, which is optionally substituted by one or more radicals $R^1$, or $P(R^1)_{3-p}$, $P(=O)(R^1)_{3-p}$, $C(R^1)_{4-p}$, $Si(R^1)_{4-p}$, $N(Ar)_{3-p}$ or a combination of two, three, four or five of these systems; or L is a chemical bond;

p is 2, 3, 4, 5 or 6, with the proviso that p is not greater than the maximum valence of L;

wherein at least one radical R stands for one of the groups of the following formula (3), formula (4), formula (5), or formula (6):

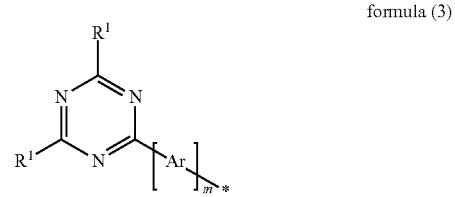

formula (3)

formula (4)

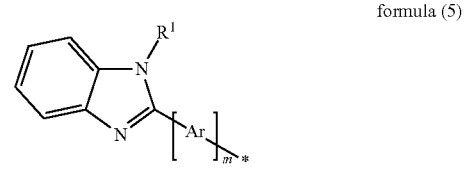

formula (5)

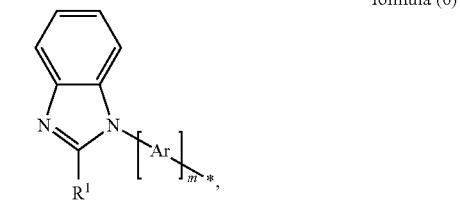

formula (6)

and/or wherein at least one group L stands for a group of the following formula (10), formula (11), formula (12), formula (13), formula (14), or formula (15):

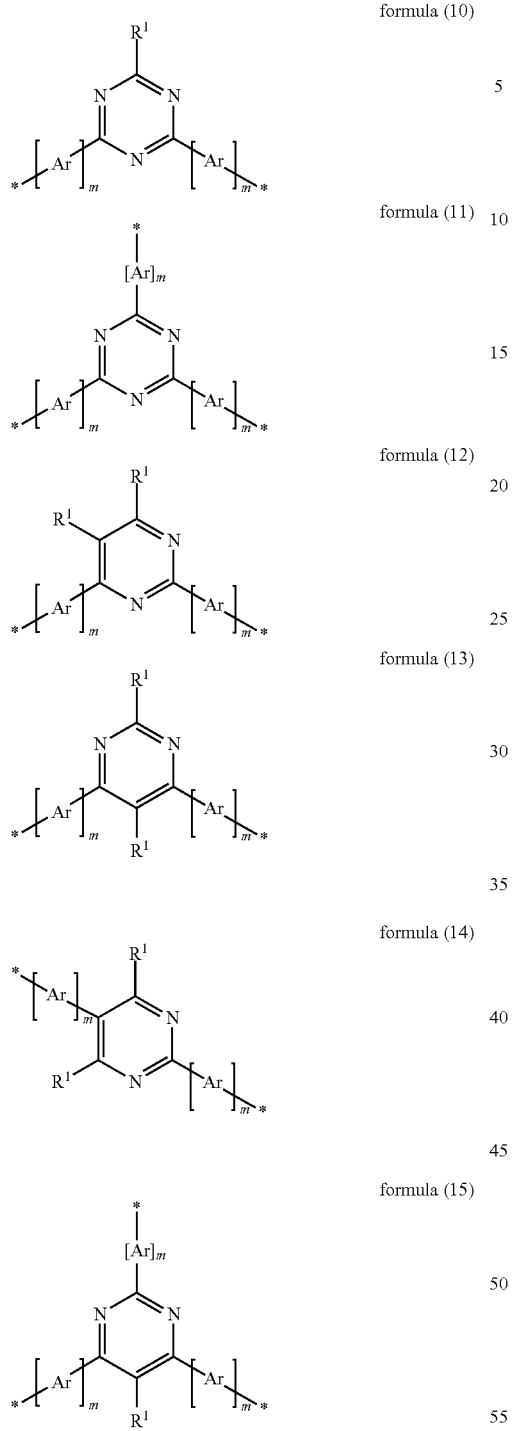

formula (10)

formula (11)

formula (12)

formula (13)

formula (14)

formula (15)

where the symbols used have the meanings given above, and the index m stands for 0 or 1; and * indicates the position of the bonding of the group of the formula (3), formula (4), formula (5), formula (6), formula (7), formula (8), formula (9), formula (10), formula (11), formula (12), formula (13), formula (14), or formula (15).

2. The compound according to claim 1 of the formula (25), formula (26), formula (27), formula (32), formula (33), formula (34), formula (35), formula (36), formula (37) formula (44), formula (45), or formula (48):

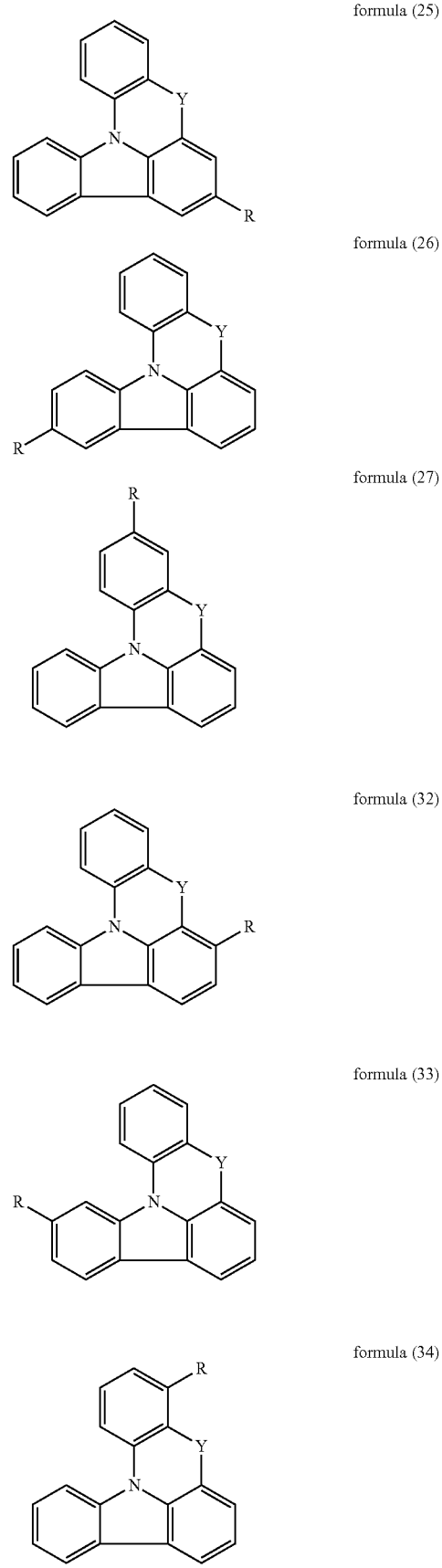

formula (25)

formula (26)

formula (27)

formula (32)

formula (33)

formula (34)

formula (35)

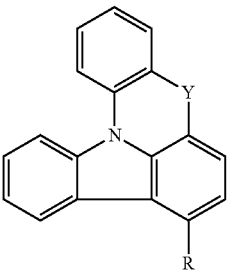

formula (36)

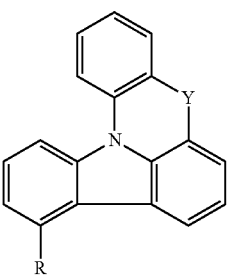

formula (37)

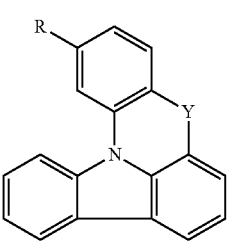

formula (44)

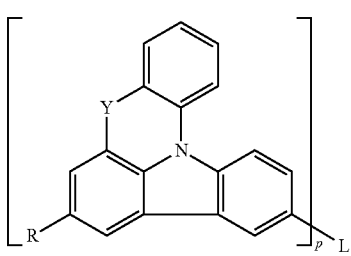

formula (45)

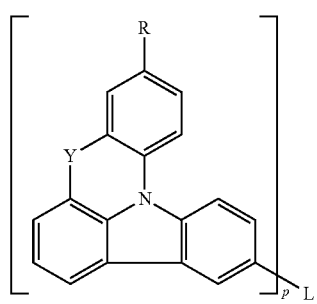

formula (48)

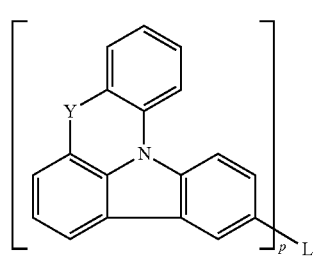

where R represents a group of one of the formula (3), formula (4), formula (5), or formula (6), and where L in formula (48) represents a group of one of the formula (10), formula (11), formula (12), formula (13), formula (14), or formula (15), Y stands, identically or differently, on each occurrence, for $C(R)_2$, where R which is bonded in the $C(R)_2$ group stands, identically or differently on each occurrence, for an alkyl group having 1 to 10 C atoms or an aromatic or heteroaromatic ring system having 5 to 18 aromatic ring atoms; furthermore, the C atoms drawn as unsubstituted may also be substituted by D instead of H.

3. The compound according to claim 2, wherein R represents a group of one of the formula (3), formula (4), formula (5), or formula (6), and where L in formula 48 represents a group of one of the formula (10), formula (11), formula (12), formula (13), formula (14), or formula (15), Y stands, identically on each occurrence, for $C(R)_2$, where R which is bonded in the $C(R)_2$ group stands, identically or differently on each occurrence, for an alkyl group having 1 to 10 C atoms or an aromatic or heteroaromatic ring system having 5 to 18 aromatic ring atoms, and at least one of the radicals R in these groups represents an aromatic or heteroaromatic ring system having 5 to 18 aromatic ring atoms, which optionally in each case be substituted by one or more radicals $R^1$; furthermore, the C atoms drawn as unsubstituted may also be substituted by D instead of H.

4. The compound according to claim 2, wherein the structures of the formula (25), formula (26), formula (27), formula (32), formula (33), formula (34), formula (35), formula (36), formula (37), formula (44), formula (45), formula (48), each contain a radical R in the position para to the central atom N, where the substituents R in the position para to the central atom N which do not stand for a group of the formula (3), formula (4), formula (5), or formula (6) stand for an alkyl group having 1 to 10 C atoms, or for an aromatic or heteroaromatic ring system having 5 to 24 aromatic ring atoms, which is optionally substituted by one or more radicals $R^1$.

5. The compound according to claim 2, wherein the structures of the formula (25), formula (26), formula (27), formula (32), formula (33), formula (34), formula (35), formula (36), formula (37), formula (44), formula (45), formula (48), each contain a radical R in the position para to the central atom N, where the substituents R in the position para to the central atom N which do not stand for a group of the formula (3), formula (4), formula (5), or formula (6) stand for an alkyl group having 1 to 4 C atoms, or for a phenyl group, which is optionally substituted by one or more radicals $R^1$.

6. The compound according to claim 1, wherein Y is $C(R)_2$.

7. The compound according to claim 1, wherein L is a divalent or polyvalent straight-chain alkylene group having 1 to 10 C atoms or a branched or cyclic alkylene group having 3 to 10 C atoms, which is optionally substituted by in each case one or more radicals $R^1$, where one or more H atoms is optionally replaced by D or F, or an at least divalent aromatic or heteroaromatic ring system having 5 to 24 aromatic ring atoms, which is optionally substituted by one or more radicals $R^1$; or L is a chemical bond; or L is a group of one of the formula (10), formula (11), formula (12), formula (13), formula (14), or formula (15).

8. The compound according to claim 1, wherein R is selected, identically or differently on each occurrence, from the group consisting of H, D, F, Cl, Br, CN, $N(Ar)_2$, $C(=O)$ Ar, a straight-chain alkyl or alkoxy group having 1 to 10 C atoms or a branched or cyclic alkyl or alkoxy group having 3 to 10 C atoms or an alkenyl or alkynyl group having 2 to 10 C atoms, each of which is optionally substituted by one or more radicals $R^1$, where one or more non-adjacent $CH_2$ groups is optionally replaced by O and where one or more H atoms is optionally replaced by D or F, an aromatic or heteroaromatic ring system having 5 to 30 aromatic ring atoms, which may in each case be substituted by one or more radicals $R^1$, an aryloxy or heteroaryloxy group having 5 to 30 aromatic ring atoms, which is optionally substituted by one or more radicals $R^1$, or a combination of these systems, where at least one radical R represents a group of the formula (3), formula (4), formula (5), formula (6), formula (7), formula (8), or formula (9).

9. The compound according to claim 1, wherein the groups R which are bonded in Y are selected, identically or differently on each occurrence, from aromatic or heteroaromatic ring systems having 5 to 20 aromatic ring atoms, which may in each case be substituted by one or more radicals $R^1$, or in that one radical R, if Y stands for $C(R)_2$, represents an alkyl group having 1 to 10 C atoms and the other radical R bonded to this carbon atom represents an aromatic or heteroaromatic ring system having 5 to 20 aromatic ring atoms, which is optionally substituted by one or more radicals $R^1$.

10. The compound according to claim 1, wherein, in the structures of the formula (3), formula (4), formula (5), formula (6), formula (7), formula (8), formula (9), formula (10), formula (11), formula (12), formula (13), formula (14), or formula (15), the symbol $R^1$ stands for an aromatic or heteroaromatic ring system having 5 to 20 aromatic ring atoms, which contains no condensed aromatic ring systems having more than 10 aromatic ring atoms and which may in each case be substituted by one or more radicals $R^2$.

11. The compound according to claim 1, wherein, in the structures of the formula (3), formula (4), formula (5), formula (6), formula (7), formula (8), formula (9), formula (10), formula (11), formula (12), formula (13), formula (14), or formula (15), the symbol $R^1$ stands for phenyl, ortho-, meta- or para-biphenyl, ortho-, meta- or para-terphenyl, quaterphenyl or 1- or 2-naphthyl, each of which is optionally substituted by one or more radicals $R^2$.

12. The compound according to claim 1, wherein the group Ar in the formula (3), formula (4), formula (5), formula (6), formula (7), formula (8), formula (9), formula (10), formula (11), formula (12), formula (13), formula (14), or formula (15), stands for an aromatic or heteroaromatic ring system having 5 to 20 aromatic ring atoms, which contains no condensed aromatic ring systems having more than 10 aromatic ring atoms and which is optionally substituted by one or more non-aromatic radicals $R^1$.

* * * * *